(12) United States Patent
Kawabori

(10) Patent No.: US 12,315,148 B2
(45) Date of Patent: May 27, 2025

(54) INTEGRATED SYSTEM FOR SAFE INTRACRANIAL ADMINISTRATION OF CELLS

(71) Applicant: RAINBOW INC., Hokkaido (JP)

(72) Inventor: Masahito Kawabori, Hokkaido (JP)

(73) Assignee: RAINBOW INC., Hokkaido (JP)

( * ) Notice: Subject to any disclaimer, the term of this patent is extended or adjusted under 35 U.S.C. 154(b) by 255 days.

(21) Appl. No.: 17/781,159

(22) PCT Filed: Dec. 25, 2020

(86) PCT No.: PCT/JP2020/048838
§ 371 (c)(1),
(2) Date: May 31, 2022

(87) PCT Pub. No.: WO2021/132600
PCT Pub. Date: Jul. 1, 2021

(65) Prior Publication Data
US 2023/0082155 A1  Mar. 16, 2023

(30) Foreign Application Priority Data

Dec. 27, 2019 (JP) ................................. 2019-239560

(51) Int. Cl.
*G06T 7/00* (2017.01)
(52) U.S. Cl.
CPC .. *G06T 7/0012* (2013.01); *G06T 2207/10088* (2013.01); *G06T 2207/20081* (2013.01);
(Continued)
(58) Field of Classification Search
CPC ......... G06T 7/0012; G06T 2207/10088; G06T 2207/20081; G06T 2207/30016;
(Continued)

(56) References Cited

U.S. PATENT DOCUMENTS

| | | |
|---|---|---|
| 2007/0014447 A1 | 1/2007 | Hubschmann |
| 2007/0167700 A1 | 7/2007 | Rahn et al. |
| | (Continued) | |

FOREIGN PATENT DOCUMENTS

| | | |
|---|---|---|
| CN | 104 207 776 A | 12/2014 |
| EP | 1 814 979 B1 | 4/2015 |
| | (Continued) | |

OTHER PUBLICATIONS

English Machine Translation of CN-105770909-A (Dodge et al., Published Jul. 20, 2016) (Year: 2016).*

(Continued)

*Primary Examiner* — Juan M Guillermety
(74) *Attorney, Agent, or Firm* — Renner, Otto, Boisselle & Sklar, LLP

(57) ABSTRACT

The present disclosure provides a method for identifying sites for administering cells in cell therapy for central nervous system damage in a subject, comprising the steps of: A) acquiring image data on at least part of the subject's brain, with an imaging device; B) obtaining information on the subject's brain, with a computer device in communication with the imaging device; C) using the image data and data pertaining to the subject's brain acquired by the computer device to depict motor fibers; D) identifying damaged locations where motor fibers have suffered damage, with the computer device, identifying a portion where motor fiber run-data is lower than another portion and identifying the lower portion as being motor fibers that have suffered damage; E) using the computer device to select, as sites of administration, safe regions near the damaged locations; and F) outputting, as graphic display, the selected sites of administration.

6 Claims, 21 Drawing Sheets

(52) U.S. Cl.
CPC ............... *G06T 2207/30016* (2013.01); *G06T 2207/30101* (2013.01)

(58) Field of Classification Search
CPC . G06T 2207/30101; G06T 2207/10081; G06T 2207/10092; G06T 2207/10132; G06T 2207/20104; G01R 33/5608; G06N 20/00; A61B 6/466; A61B 6/5217; A61B 8/0808; A61B 8/5223; A61B 6/501; A61B 6/032; A61B 6/469; G06V 10/25; H04N 19/167; H04N 21/4728; A61M 2210/0693; A61K 2239/47
See application file for complete search history.

(56) References Cited

U.S. PATENT DOCUMENTS

| | | |
|---|---|---|
| 2009/0269311 A1 | 10/2009 | Lee et al. |
| 2014/0303662 A1 | 10/2014 | Aoyagi |
| 2015/0148660 A1 | 5/2015 | Weiss et al. |
| 2016/0237404 A1 | 8/2016 | Izrael et al. |
| 2017/0200270 A1* | 7/2017 | Reicher ................. A61B 5/742 |
| 2019/0105105 A1 | 4/2019 | Zagorchev et al. |
| 2019/0108638 A1* | 4/2019 | Zagorchev ......... G01R 33/5608 |
| 2021/0008227 A1* | 1/2021 | Dodge .................... A61P 25/02 |
| 2021/0012858 A1 | 1/2021 | Yamashita et al. |

FOREIGN PATENT DOCUMENTS

| | | |
|---|---|---|
| JP | 2007185503 A | 7/2007 |
| JP | 2009500069 A | 1/2009 |
| JP | 2014111083 A | 6/2014 |
| JP | 2015521883 A | 8/2015 |
| JP | 2016517288 A | 6/2016 |
| WO | 2013/124815 A2 | 8/2013 |
| WO | 2014138916 A1 | 9/2014 |
| WO | 2019/177152 A1 | 9/2019 |

OTHER PUBLICATIONS

International Search Report for related International Application No. PCT/JP2020/048838 mailed Mar. 23, 2021 and its English Translation.

Extended search report issued on May 18, 2024, for corresponding European Application No. 20 90 7785.8.

Notice of Reasons for Refusal for corresponding Application No. 2002-005015, issued Jan. 9, 2025, with English translation.

* cited by examiner

[Figure 1A]

[Figure 1B]
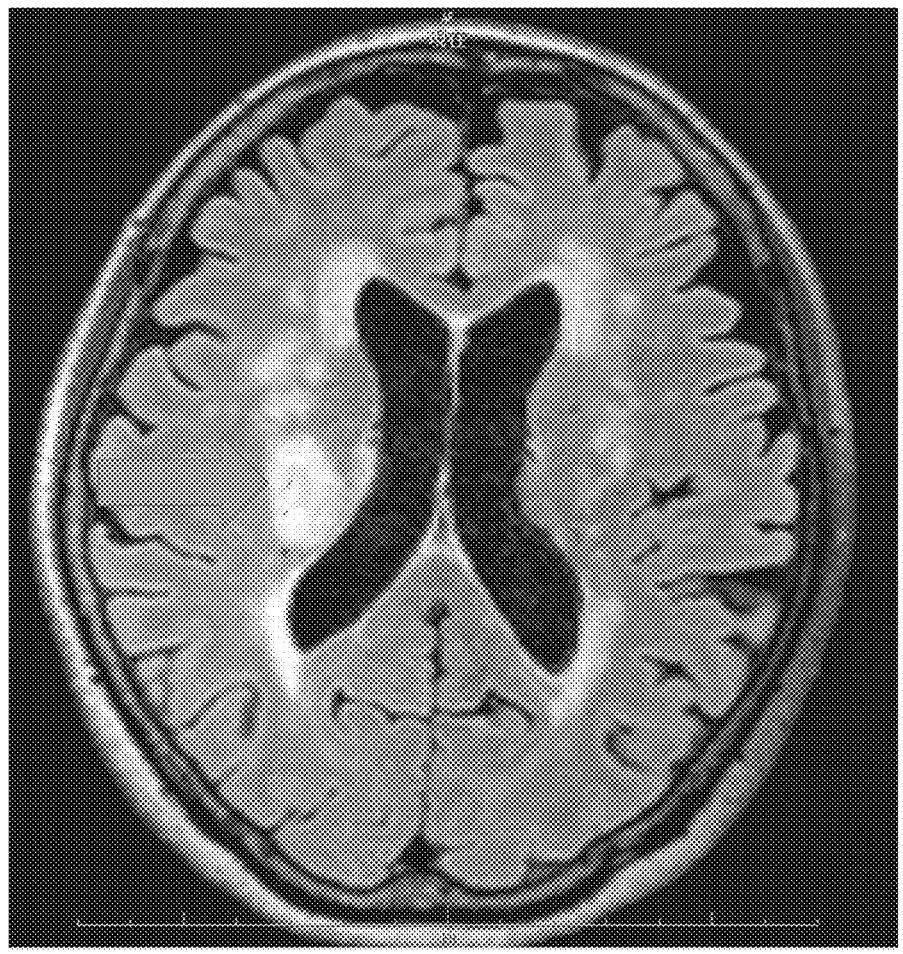

[Figure 1C]
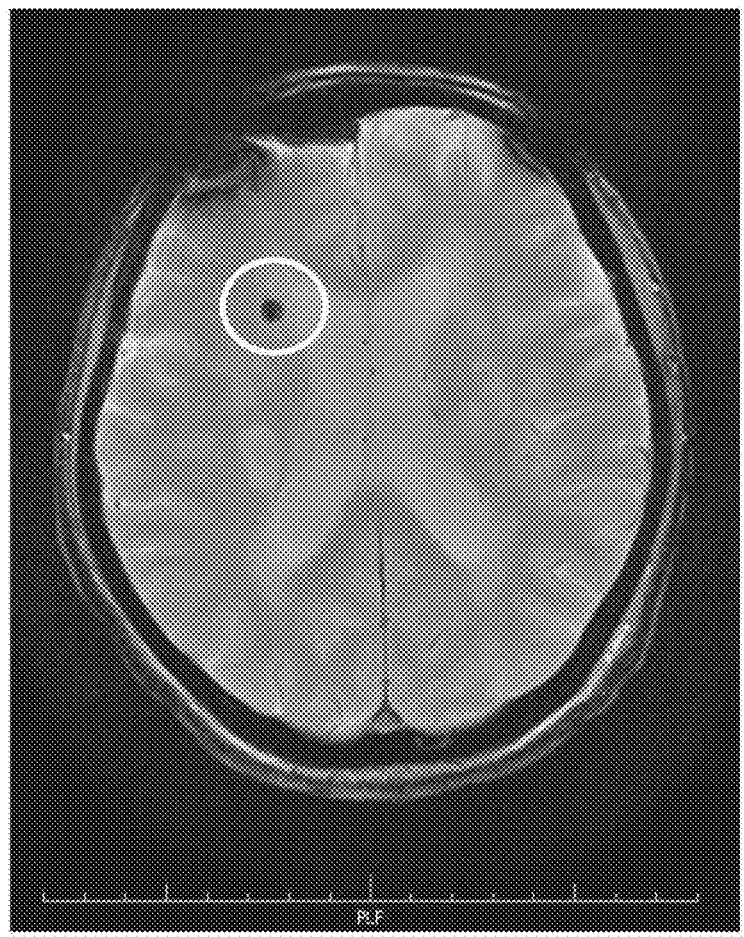

[Figure 2A]
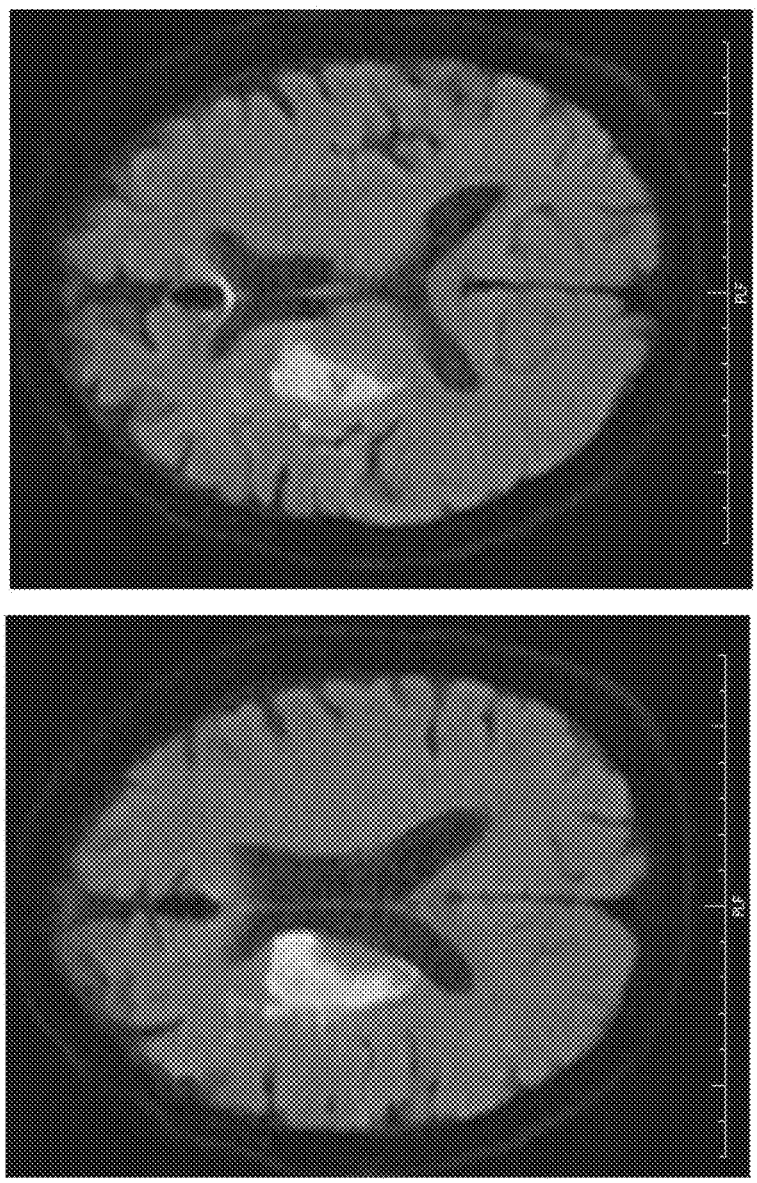

[Figure 2B]
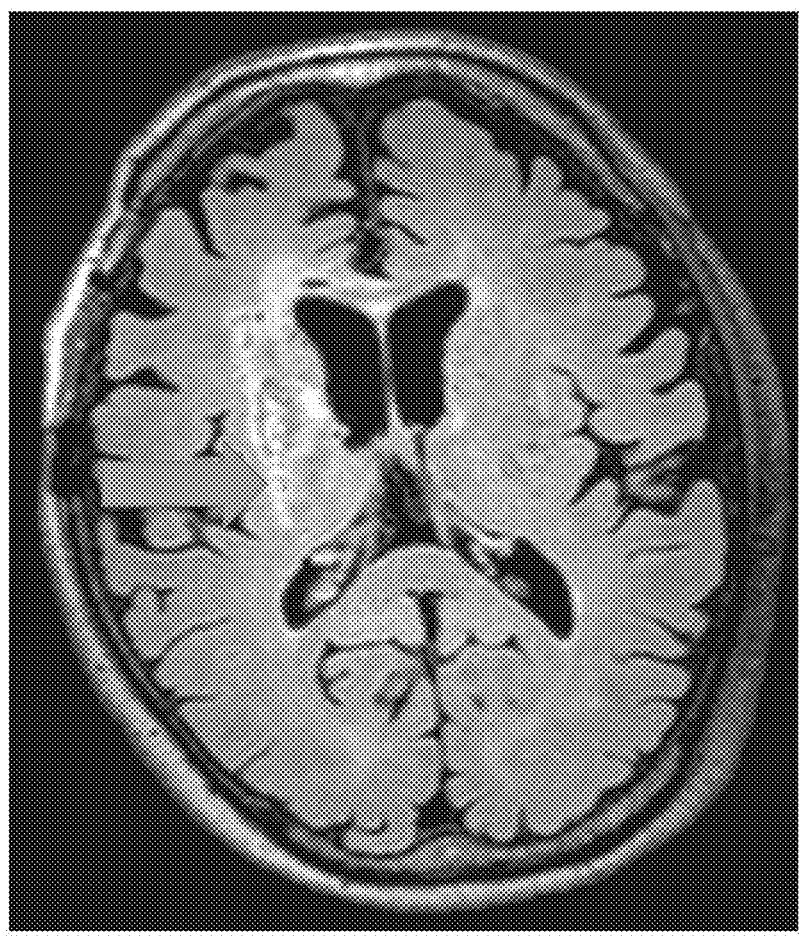

[Figure 2C]
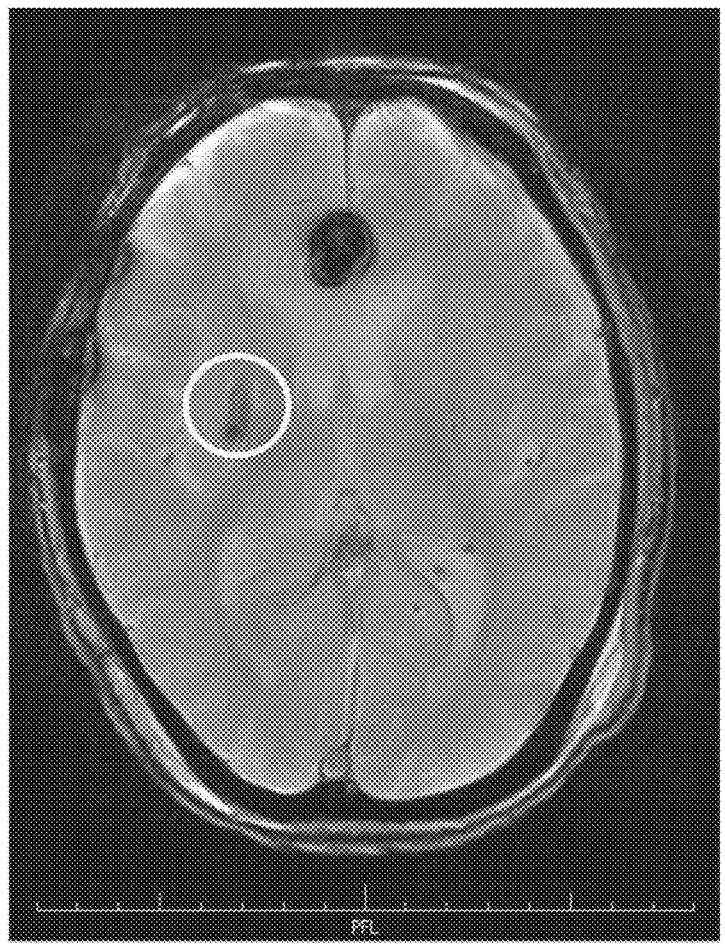

[Figure 3A]
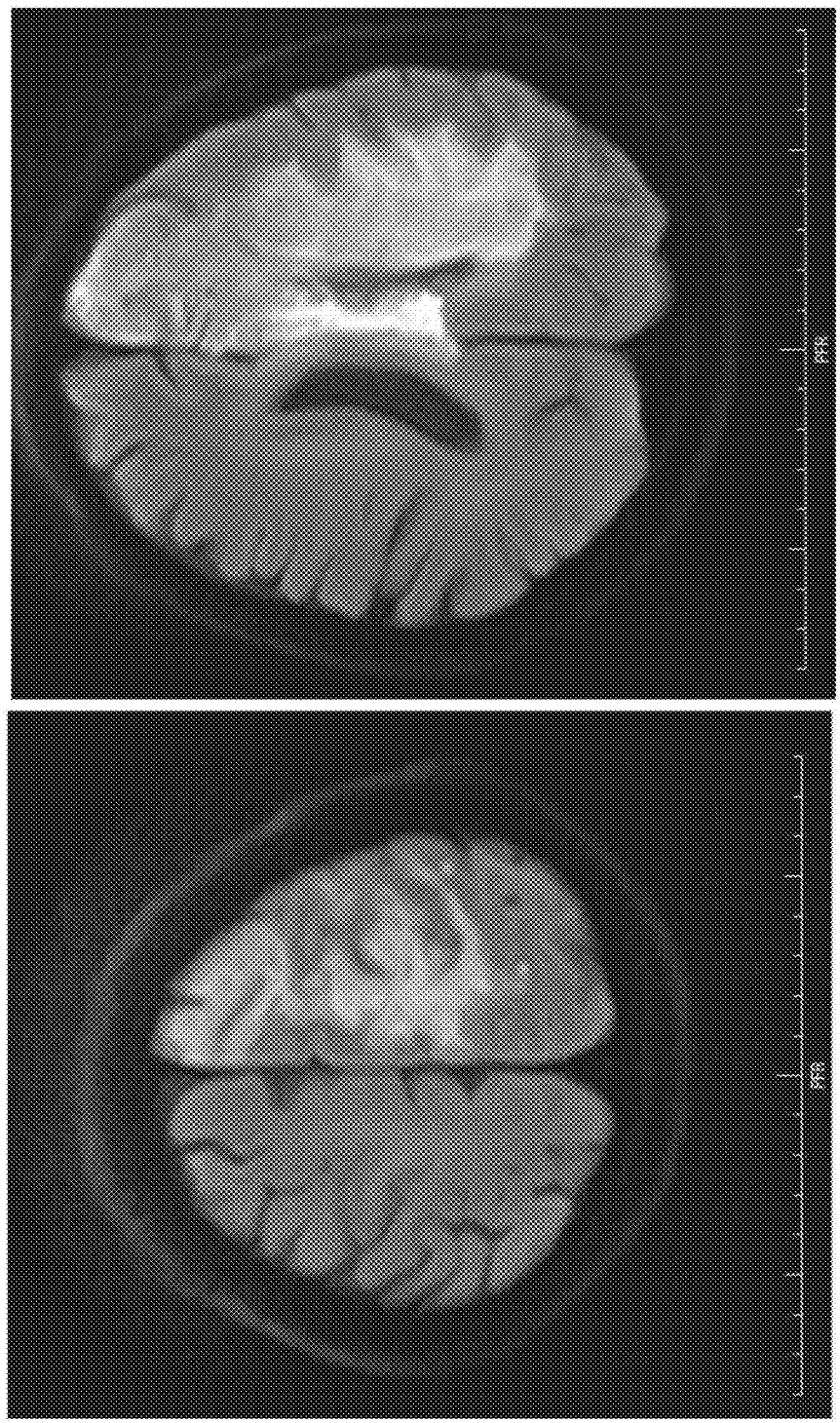

[Figure 3B]
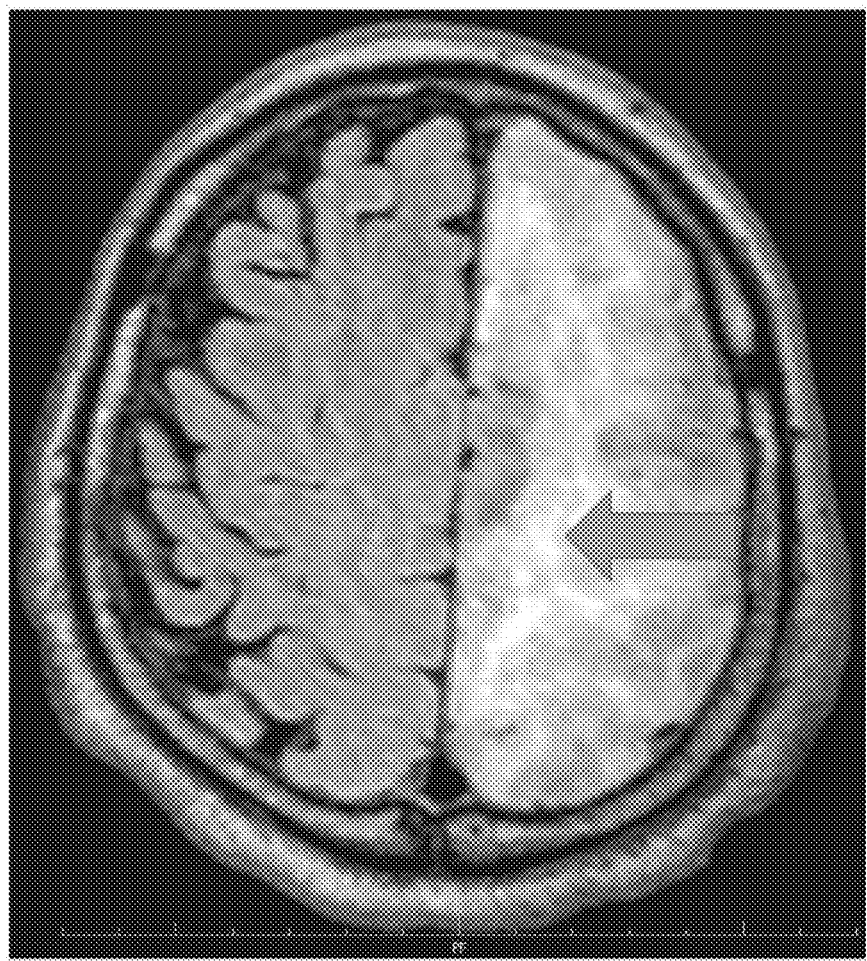

[Figure 3C]
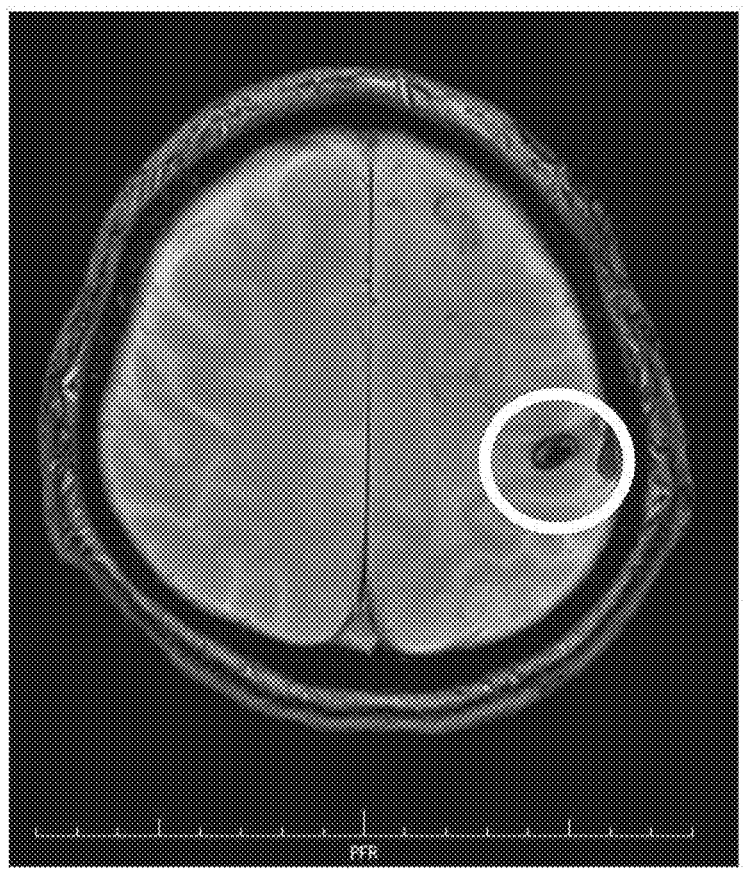

[Figure 4A]
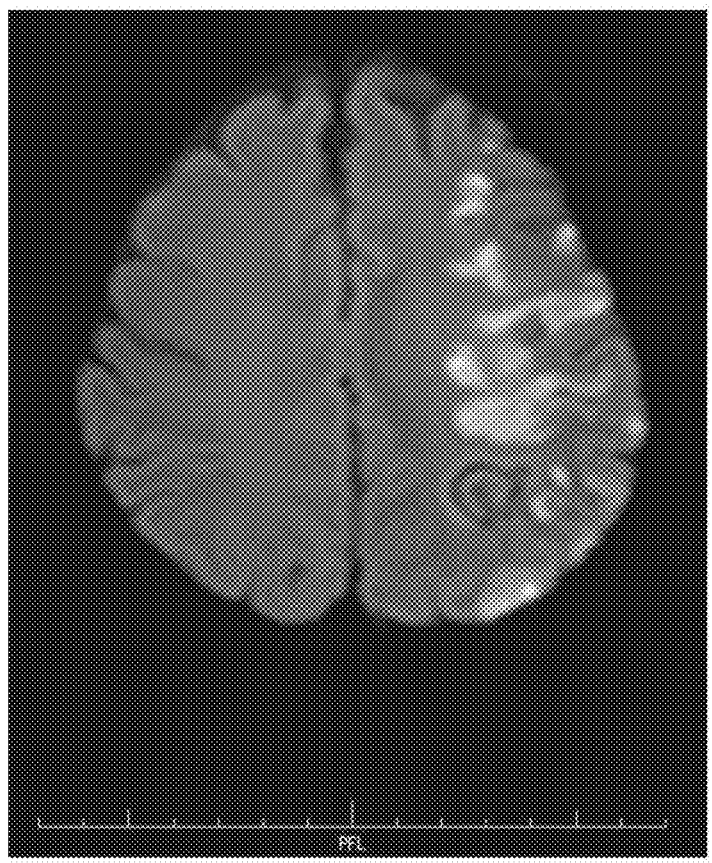

[Figure 4B]
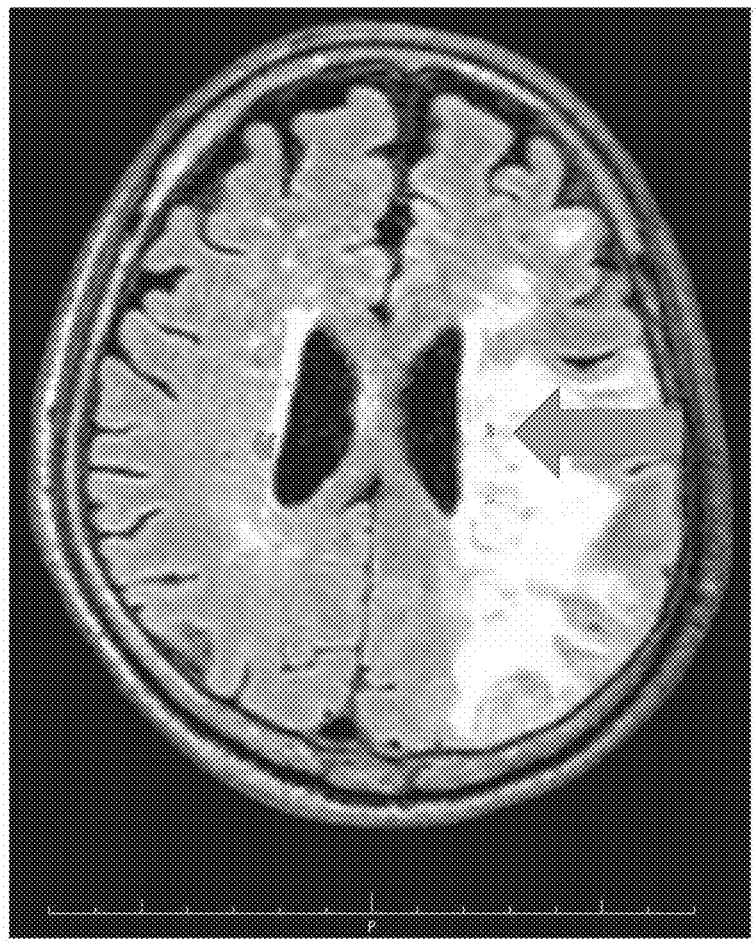

[Figure 4C]
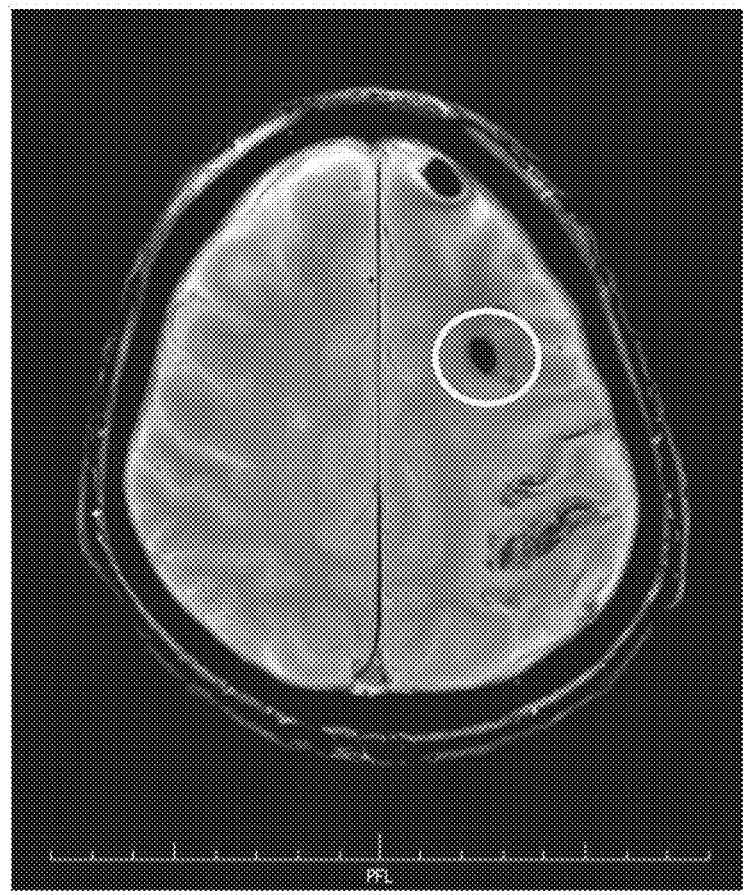

[Figure 5A]
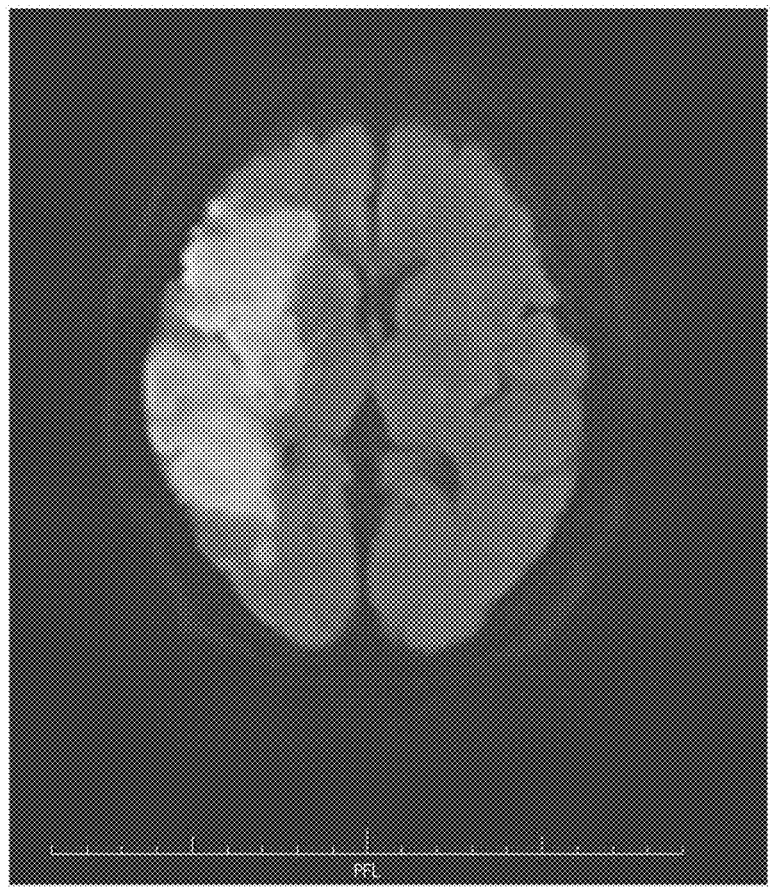

[Figure 5B]
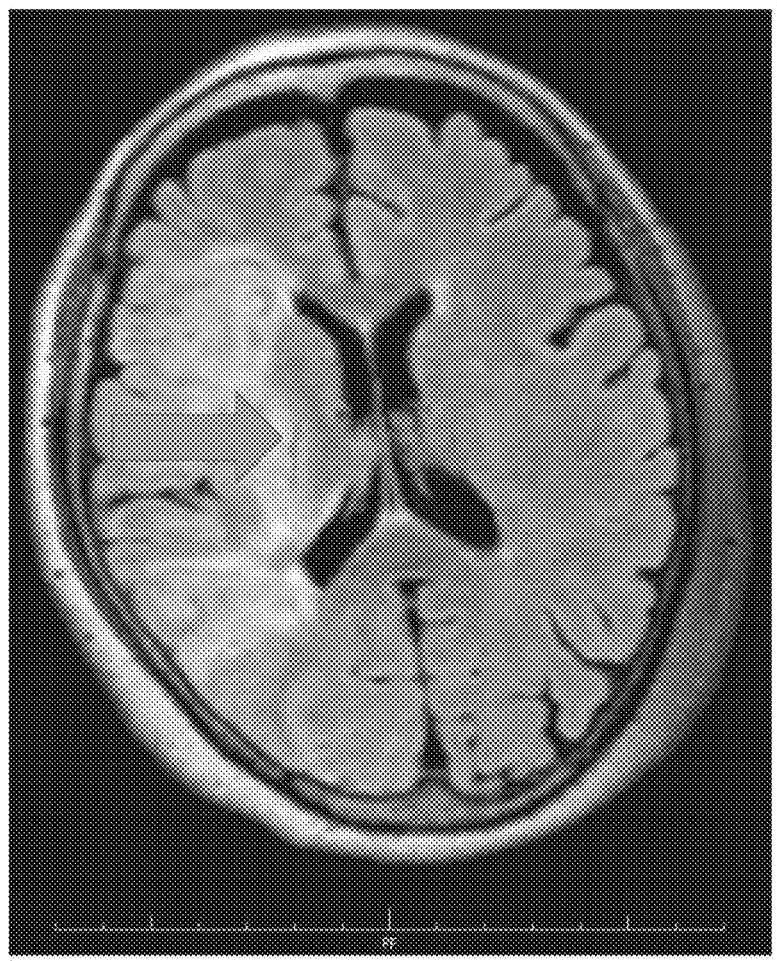

[Figure 5C]
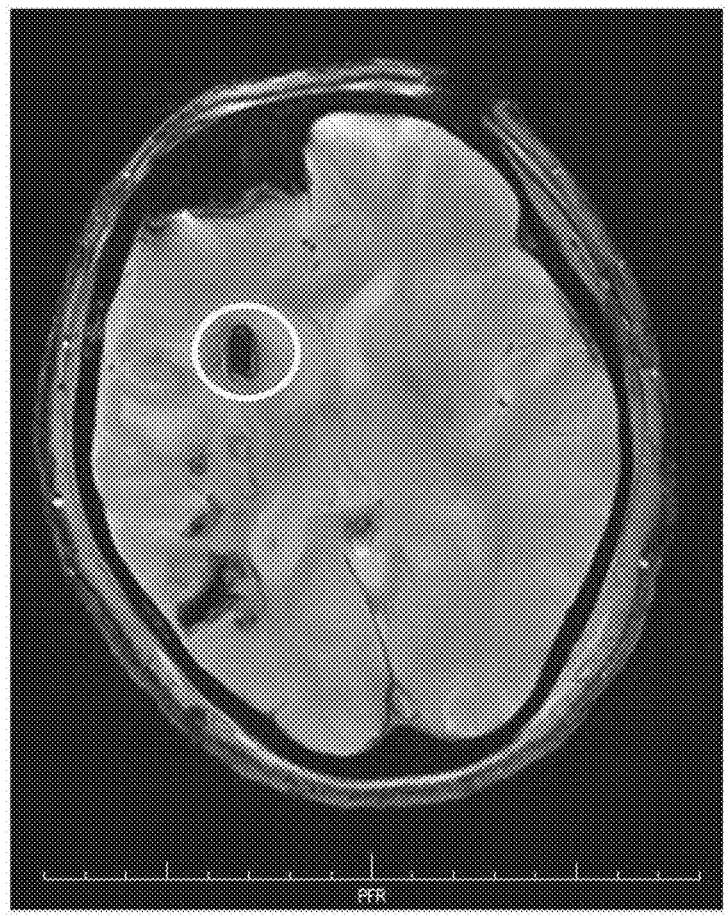

[Figure 6A]

[Figure 6B]
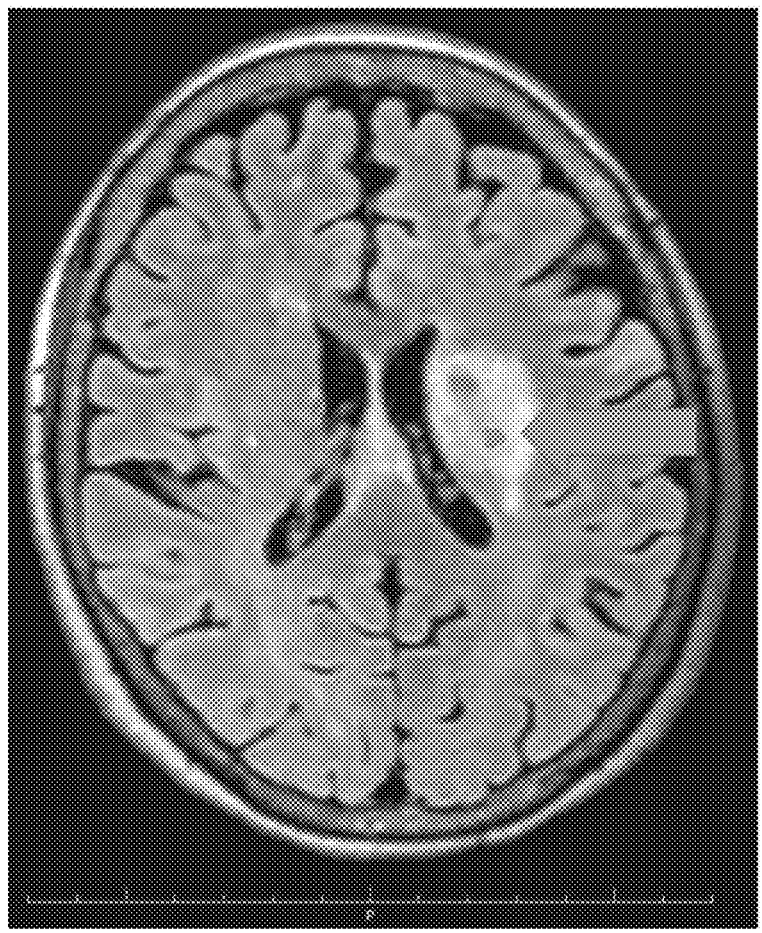

[Figure 6C]
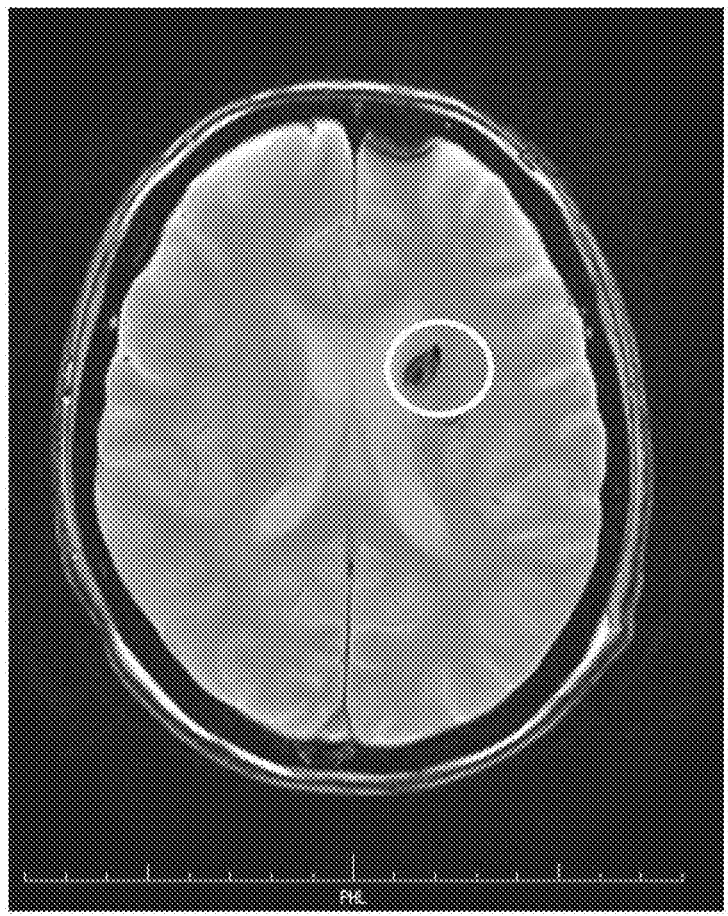

[Figure 7A]
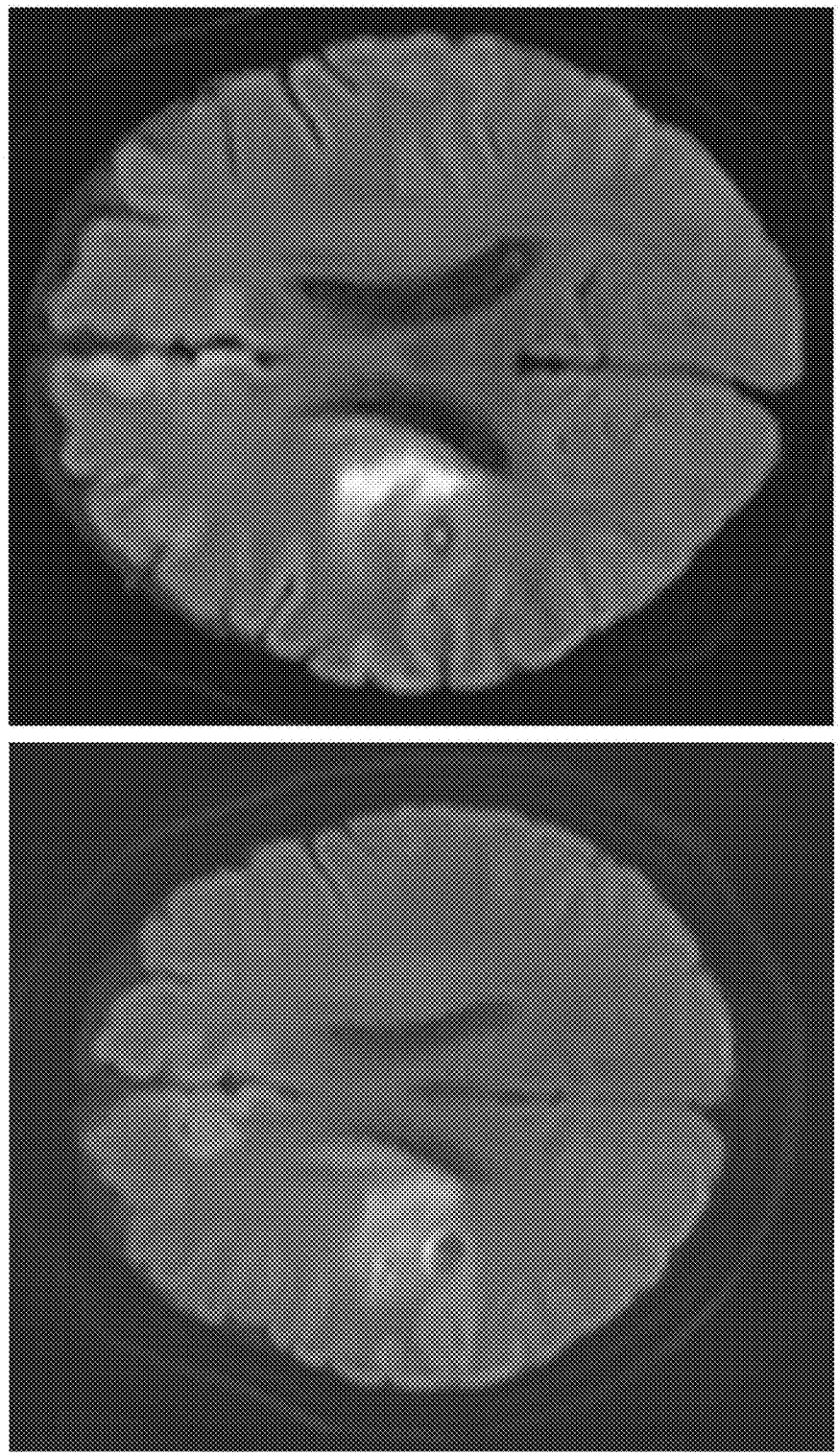

[Figure 7B]
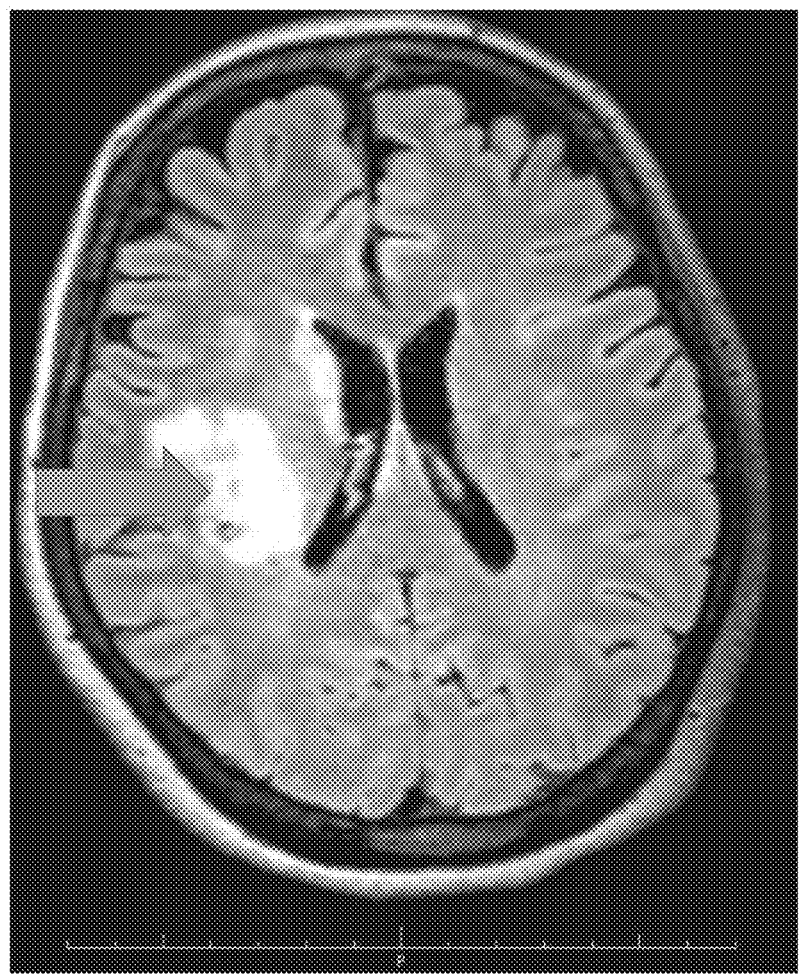

[Figure 7C]
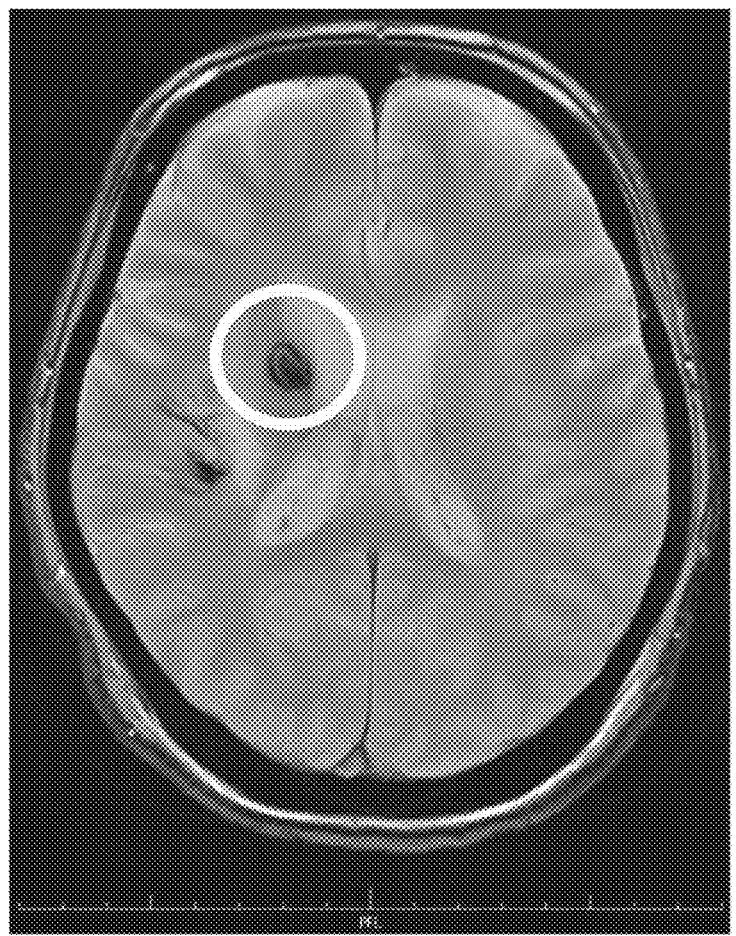

INTEGRATED SYSTEM FOR SAFE INTRACRANIAL ADMINISTRATION OF CELLS

TECHNICAL FIELD

The present disclosure relates to techniques useful in cell therapy for central nervous system disorders (cerebral infarction, cerebral hemorrhage, etc.).

BACKGROUND ART

Cell therapy is expected for central nervous system disorders (cerebral infarction, cerebral hemorrhage, etc.). Intracerebral administration can be considered as one of the administration methods, which can avoid the blockage of the blood-brain barrier, and which thus has the advantage of being able to send a large amount of cells to the affected area compared to transvascular (venous/arterial) administration. However, there is a risk of creating new brain damage as a problem in the intracerebral administration. In order to avoid such a risk, it is necessary to (1) prevent a risk regarding a cell administration site (avoid important sites), (2) prevent a risk regarding a region through which the administration needle passes (avoid sulci and blood vessels), and (3) prevent brain shift due to cerebrospinal fluid leakage. There is no existing technique disclosed for cell therapy for these integrated systems.

SUMMARY OF INVENTION

Solution to Problem

The present inventors provide a new method of surgery/administration in the present disclosure. The method is mainly characterized by the following.

(1) Determination of administration site: Motor fibers are visualized by brain MRI in advance to determine the cell administration site. The damaged part of the visualized motor fibers is determined (if the brain damage is strong and the motor fibers are not visualized, refer to the healthy motor fibers on the contralateral side) to select a site that is as close as possible to the site (within a radius of 1.5 cm) and that is not considered to have an important role in nerve function as the administration site.

(2) Determining the passing region for the administration needle: Thick veins on a brain surface are confirmed in advance using brain MRI, and they are formulated so that the needle does not penetrate the same site when the needle passes. In addition, once the needle is inserted into the brain, a passage is selected so that the needle does not come out of the sulcus (the needle can reach the sulci and damage the small veins and arteries that run on the brain surface). This approach can be depicted not only as a method of surgery, but also as a program invention.

(3) Method of preventing cerebrospinal fluid leakage: An incision of an arachnoid membrane on the surface of the brain causes the cerebrospinal fluid in the brain to flow out. Since the brain exists as if it were floating in the cerebrospinal fluid, a brain shift (sinking) occurs in which the position of the brain shifts over time. To prevent this, there is a method of, before incising the arachnoid membrane, coagulating and adhering the arachnoid membrane and pia mater on the brain surface at the planned puncture site using electrosurgical instruments such as bipolar coagulation tweezers. This can prevent the brain from shifting even when the needle is inserted. This is especially important if multiple punctures are required.

The present invention provides the following items.

(Item 1)

A method for identifying a site of administration of cells in cell therapy for a central nervous system disorder in a subject, the method comprising:
  A) acquiring, by an imaging device, image data on at least part of the brain of the subject;
  B) obtaining information on the brain of the subject by a computer device in communication with the imaging device;
  C) depicting motor fibers by the computer device using the acquired image data and data on the brain of the subject;
  D) identifying, by the computer device, a damage position in which the motor fibers are damaged, which identifies a part where running data on the motor fibers is lower than other sites to identify the lower part as damaged motor fibers;
  E) selecting, by the computer device, a safe region near the damage position as an administration site; and
  F) outputting the selected administration site as a graphic display.

(Item 2)

The method according to any of the preceding items, wherein the imaging device comprises an MRI, a CT, an ultrasound examination device or an angiography examination device.

(Item 3)

The method according to item 1, wherein the running data on the motor fibers is represented in a DTI image.

(Item 4)

The method according to any of the preceding items, wherein the running data is represented by an FA value (fractional anisotropy value) in the DTI image.

(Item 5)

The method according to any of the preceding items, wherein a decrease in the running data at a site where the running data on the motor fibers is lower than other parts is a decrease of at least 50% or more.

(Item 6)

The method according to any of the preceding items, wherein the safe region includes a position present within a radius of about 1.5 cm from the damage position.

(Item 7)

The method according to any of the preceding items, wherein the safe region is a position present within a radius of about 1.5 cm from the damage position and is selected from a site considered to have no important function on nerve function.

(Item 8)

The method according to any of the preceding items, wherein the administration site is positioned caudally to the brain relative to the damage position.

(Item 9)

The method according to any of the preceding items, wherein the administration site is determined for each damage position.

(Item 10)

The method according to any of the preceding items, wherein one or more of the administration sites exist with respect to the damage position.

(Item 11)

The method according to any of the preceding items, characterized in that when the running data on the motor fibers is not acquired, a damaged part is determined with reference to healthy motor fibers on a contralateral side.
(Item 12)
The method according to any of the preceding items, wherein, as for the selecting, a DWI image is compared with a T2 image to determine a region damaged by current cerebral infarction, and the region is excluded from the selection,
a site that is DWI-negative but has strong edema in the T2 image and a FLAIR image is also excluded from the selection, and
motor fibers are visualized in a DTI region, and the region of the visualized motor fibers is excluded from the selection.
(Item 13)
The method according to any of the preceding items, wherein in the T2-weighted image and the FLAIR image in the MRI, a site that meets both of:
a) a high signal intensity area in the FLAIR image plotting signal intensity; and
b) a high signal intensity area in the T2-weighted image plotting signal intensity,
is identified as edema.
(Item 14)
The method according to any of the preceding items, characterized in that:
[1] when tractography is visualized in the DTI image, a site that meets conditions of:
(a) normal brain tissue that is as close as possible to an area where the tractography is raptured or weakened in the DTI image (usually a white area with DWI in the acute phase of cerebral infarction; high signal intensity in T2/FLAIR in the chronic phase of cerebral infarction; high signal intensity in CT in the acute phase of trauma/cerebral hemorrhage; high signal intensity in T2/FLAIR in the chronic phase of trauma/cerebral hemorrhage); and
(b) a highly safe region (an area where there is little damage even if bleeding or allergic reaction occurs: a site other than the site generally referred to as an eloquent area* in AVM),
and
(c) optionally, a part that avoids, but is as close as possible to, the high signal intensity area in the T2/FLAIR image,
is selected as an administration site, or
[2] when tractography is not visualized in the DTI image,
(aa) the setting for ROI for visualizing tractography is set solely for each of the precentral gyrus, the crus posterius capsulae internae, and the bridge (usually, nerve fibers that pass through the following three: the precentral gyrus, the crus posterius capsulae internae, and the bridge are often selected.), and with the visualized tractography used as a reference, from among them, normally expected motor fibers in humans are selected, or
(bb) when tractography is not visualized even in the (aa), running of motor fibers is estimated with reference to tractography on the contralateral side, and a site where an injured site indicated as high signal intensity in a DWI image in the acute phase, or an injured site indicated as low signal intensity in a T2/FLAIR image in the chronic phase, overlaps with an estimated passing point of tractography is estimated to be the site where motor fibers are ruptured, to perform [1].

(Item 15)
A method for identifying a passing region for an administration needle for administration of cells in cell therapy for a central nervous system disorder in a subject, the method comprising:
(A) acquiring image data on at least part of the brain of the subject using an imaging device;
(B) obtaining information on the brain of the subject by a computer device in communication with the imaging device;
(C) depicting, by the computer device, a blood vessel from the acquired image data and the information on the brain of the subject;
(D) identifying, by the computer device, a route range that does not allow penetration of the blood vessel;
(E) identifying, by the computer device, a sulcus non-invasive range where a needle does not come out of the sulcus after the needle is inserted into the brain;
(F) setting, by the computer device, a route within a range where the route ranges calculated in (D) and (E) overlap with each other; and
(G) outputting the set route as a graphic display.
(Item 16)
The method according to item 15, wherein the blood vessel comprises a thick vein that flows from the surface of the brain into the superior sagittal sinus.
(Item 17)
The method according to any of the preceding items, wherein the identifying determines a high signal intensity area in a gadolinium-enhanced T1 image as a blood vessel.
(Item 18)
The method according to any of the preceding items, wherein the identifying is based on an MRI image and is achieved by measuring at least one of DWI, T2, FLAIR (fluid-attenuated inversion-recovery), and DTI, with regard to the MRI image.
(Item 19)
The method according to any of the preceding items, wherein the identifying is based on an MRI image and is determined by a sequence of (1) a FLAIR image, (3) a T2 image, and (3) a gadolinium-enhanced T1 image, with regard to the MRI image.
(Item 20)
The method according to any of the preceding items, wherein the identification of the sulcus non-invasive route is accomplished by confirming the T2-weighted image and the FLAIR image in MRI.
(Item 21)
The method according to any of the preceding items, wherein, in (E), a site that meets both of:
1) a low signal intensity area in the FLAIR image plotting signal intensity; and
2) a high signal intensity area in the T2-weighted image plotting signal intensity,
is identified as a sulcus.
(Item 22)
A method of preventing cerebrospinal fluid leakage in the brain of a subject, the method comprising:
A) incising the dura mater present on a surface of the brain; and
B) coagulating and adhering the arachnoid membrane and pia mater on a brain surface at a planned puncture initiating site using an electrosurgical instrument, wherein the arachnoid membrane is coagulated and adhered to the pia mater (a) until the arachnoid becomes cloudy, (b) until the microvessels present on the surface of the brain can no longer be confirmed visually on the arachnoid membrane or in the image displaying the arachnoid membrane, or (c) under a condition that an output power is set to an output power at which the arachnoid membrane is confirmed to become cloudy.

(Item 23)

The method according to any of the preceding items, wherein the prevention of cerebrospinal fluid leakage in the brain is performed in cell therapy for a central nervous system disorder of the subject.

(Item 24)

The method according to any of the preceding items, further comprising C) administering cells required for the subject.

(Item 25)

A system for preventing cerebrospinal fluid leakage in the brain of a subject, the system comprising:
- A) an incision tool that cuts through the dura mater present on a surface of the brain;
- B) an electrosurgical instrument configured to coagulate and adhere the arachnoid membrane and pia mater on the brain surface at a planned puncture initiating site, wherein the electrosurgical instrument is operated such that the arachnoid membrane is coagulated and adhered to the pia mater (a) until the arachnoid becomes cloudy, (b) until the microvessels present on the surface of the brain can no longer be confirmed visually on the arachnoid membrane or in the image displaying the arachnoid membrane, or (c) under a condition that an output power is set to an output power at which the arachnoid membrane is confirmed to become cloudy; and
- C) a sensor that can detect the cloudiness of the arachnoid membrane.

(Item 26)

A method for identifying a route of administration of cells in cell therapy for a central nervous system disorder in a subject, the method comprising:
- i) acquiring, by an imaging device, image data on at least part of the brain of the subject;
- ii) obtaining information on the brain of the subject by a computer device in communication with the imaging device;
- iii) providing a candidate for a route of administration of cells by the following procedure, the providing step comprising:
  - aa) selecting, by the computer device, a safe region near a damage position as an administration site;
  - bb) identifying an administration route to the selected administration site; and
  - cc) optionally, selecting, by the computer device, an excision position for passing an administration device for administering the cells in the scalp, and
- iv) outputting the selected administration site as a graphic display.

(Item 27)

The method according to any of the preceding items, wherein the aa) comprises:
- C) depicting, by the computer device, motor fibers using the acquired image data and data on the brain of the subject;
- D) identifying, by the computer device, a damage position at which the motor fibers are damaged, wherein in running data on the motor fibers, a part where the amount of the motor fibers is lower than other sites is identified to identify the lower part as damaged motor fibers; and
- E) selecting, by the computer device, a safe region near the damage position as an administration site.

(Item 28)

The method according to any of the preceding items, wherein the bb) comprises:
- (C) depicting, by the computer device, a blood vessel from the acquired image data and the information on the brain of the subject;
- (D) identifying, by the computer device, a route range that does not allow penetration of the blood vessel;
- (E) identifying, by the computer device, a sulcus non-invasive range where a needle does not come out of the sulcus after the needle is inserted into the brain; and
- (F) setting, by the computer device, a route within a range where the route ranges calculated in (D) and (E) overlap with each other.

(Item 29)

The method according to any of the preceding items, wherein the imaging device comprises an MRI, a CT, an ultrasound examination device or an angiography examination device.

(Item 30)

The method according to any of the preceding items, wherein the running data on the motor fibers is represented in a DTI image.

(Item 31)

The method according to any of the preceding items, wherein the running data is represented by an FA value (fractional anisotropy value) in the DTI image.

(Item 32)

The method according to any of the preceding items, wherein a decrease in the running data at a site where the running data on the motor fibers is lower than other parts is a decrease of at least 50% or more.

(Item 33)

The method according to any of the preceding items, wherein the safe region includes a position present within a radius of about 1.5 cm from the damage position.

(Item 34)

The method according to any of the preceding items, wherein the safe region is a position present within a radius of about 1.5 cm from the damage position and is selected from a site considered to have no important function on nerve function.

(Item 35)

The method according to any of the preceding items, wherein the administration site is positioned caudally to the brain relative to the damage position.

(Item 36)

The method according to any of the preceding items, wherein the administration site is determined for each damage position.

(Item 37)

The method according to any of the preceding items, wherein one or more of the administration sites exist with respect to the damage position.

(Item 38)

The method according to any of the preceding items, characterized in that when the running data on the motor fibers is not acquired, a damaged part is determined with reference to healthy motor fibers on a contralateral side.

(Item 39)

The method according to any of the preceding items, wherein, as for the selecting, a DWI image is compared with a T2 image to determine an area damaged by current cerebral infarction, and the area is excluded from the selection, a site that is DWI-negative but has strong edema in the T2 image and a FLAIR image is also excluded from the selection, and motor fibers are visualized in a DTI region, and the area of the visualized motor fibers is excluded from the selection.

(Item 40)

The method according to any of the preceding items, wherein in the T2-weighted image and the FLAIR image in the MRI, a site that meets both of:
 a) a high signal intensity area in the FLAIR image plotting signal intensity; and
 b) a high signal intensity area in the T2-weighted image plotting signal intensity,
 is identified as edema.

(Item 41)

The method according to any of the preceding items, characterized in that:
 [1] when tractography is visualized in the DTI image, a site that meets conditions of:
  (a) normal brain tissue that is as close as possible to an area where the tractography is raptured or weakened in the DTI image (usually a white area with DWI in the acute phase of cerebral infarction; high signal intensity in T2/FLAIR in the chronic phase of cerebral infarction; high signal intensity in CT in the acute phase of trauma/cerebral hemorrhage; high signal intensity in T2/FLAIR in the chronic phase of trauma/cerebral hemorrhage); and
  (b) a highly safe region (an area where there is little damage even if bleeding or allergic reaction occurs: a site other than the site generally referred to as an eloquent area* in AVM), and
  (c) optionally, a part that avoids, but is as close as possible to, the high signal intensity area in the T2/FLAIR image,
  is selected as an administration site, or
 [2] when tractography is not visualized in the DTI image,
  (aa) the setting for ROI for visualizing tractography is set solely for each of the precentral gyrus, the crus posterius capsulae internae, and the bridge (usually, nerve fibers that pass through the following three: the precentral gyrus, the crus posterius capsulae internae, and the bridge are often selected.), and with the visualized tractography used as a reference, from among them, normally expected motor fibers in humans are selected, or
  (bb) when tractography is not visualized even in the (aa), running of motor fibers is estimated with reference to tractography on the contralateral side, and a site where an injured site indicated as high signal intensity in a DWI image in the acute phase, or an injured site indicated as low signal intensity in a T2/FLAIR image in the chronic phase, overlaps with an estimated passing point of tractography is estimated to be the site where motor fibers are ruptured, to perform [1].

(Item 42)

The method according to any of the preceding items, wherein the blood vessel comprises a thick vein that flows from the surface of the brain into the superior sagittal sinus.

(Item 43)

The method according to any of the preceding items, wherein the identifying determines a high signal intensity area in a gadolinium-enhanced T1 image as a blood vessel.

(Item 44)

The method according to any of the preceding items, wherein the identifying is based on an MRI image and is achieved by measuring at least one of DWI, T2, FLAIR (fluid-attenuated inversion-recovery), and DTI, with regard to the MRI image.

(Item 45)

The method according to any of the preceding items, wherein the identifying is based on an MRI image and is determined by a sequence of (1) a FLAIR image, (3) a T2 image, and (3) a gadolinium-enhanced T1 image, with regard to the MRI image.

(Item 46)

The method according to any of the preceding items, wherein the identification of the sulcus non-invasive route is accomplished by confirming the T2-weighted image and the FLAIR image in MRI.

(Item 47)

The method according to any of the preceding items, wherein, in (E), a site that meets both of:
 1) a low signal intensity area in the FLAIR image plotting signal intensity; and
 2) a high signal intensity area in the T2-weighted image plotting signal intensity,
 is identified as a sulcus.

(Item 48)

A method for identifying a route of administration of cells in cell therapy for a central nervous system disorder in a subject, the method comprising:
 i) acquiring, by an imaging device, image data on at least part of the brain of the subject;
 ii) obtaining information on the brain of the subject by a computer device in communication with the imaging device;
 iii) providing a candidate for a route of administration of cells by the following procedure, the providing step comprising:
  a) optionally, selecting, by the computer device, an excision position for passing an administration device for administering the cells in the scalp;
  b) selecting, by the computer device, an opening for allowing the administration device to pass through in the cranial bone for administering cell therapy;
  c) identifying, by the computer device, at least one brain route exclusion region selected from the group consisting of motor fibers, cerebral blood vessels, sulci, and functional sites using the acquired image data and data on the brain of the subject;
  d) selecting, by the computer device, a safe region near the damage position as an administration site; and
  e) depicting an administration route between the opening and the administration site, wherein the administration route is depicted with information about the brain route exclusion region, and optionally providing suitability information about the administration route from the information about the brain route exclusion region, and
 iv) outputting the selected administration site as a graphic display.

(Item 49)

The method according to any of the preceding items, wherein the imaging device comprises an MRI, a CT, an ultrasound examination device or an angiography examination device.

(Item 50)

The method according to any of the preceding items, wherein the d) comprises:
- C) depicting, by the computer device, motor fibers using the acquired image data and data on the brain of the subject;
- D) identifying, by the computer device, a damage position in which the motor fibers are damaged, which identifies a part where running data on the motor fibers is lower than other sites to identify the lower part as damaged motor fibers; and
- E) selecting, by the computer device, a safe region near the damage position as an administration site.

(Item 51)

The method according to any of the preceding items, which comprises, in the c), deciding a high signal intensity area in a gadolinium-enhanced T1 image as the cerebral blood vessels.

(Item 52)

The method according to any of the preceding items, wherein, in the c), a site that meets both of:
- 1) a low signal intensity area in the FLAIR image plotting signal intensity; and
- 2) a high signal intensity area in the T2-weighted image plotting signal intensity, is identified as a sulcus.

(Item 53)

A method of predicting the probability of occurrence of adverse effects of cell therapy on a central nervous system disorder in a subject, the method comprising:
- 1) inputting a group of data indicating a cell administration position and data on the occurrence of adverse effects of cell therapy for each cell administration position into an artificial intelligence model as learning data and causing the artificial intelligence model to learn the learning data;
- 2) acquiring a group of data indicating a cell administration position;
- 3) inputting the group of data indicating a cell administration position acquired in the 2) into the learned artificial intelligence model; and
- 4) causing the learned artificial intelligence model to calculate the probability of occurrence of adverse effects of cell therapy.

(Item 54)

The method according to item 53, wherein the group of data indicating a cell administration position includes data on at least one of a distance between an administration position and a brain surface, a distance between an administration position and a damage position, a distance between an administration position and an edema area, and whether the administration position is a site other than the site referred to as the eloquent area in cerebral arteriovenous malformation (AVM).

(Item 55)

The method according to item 54 or 55, wherein the group of data indicating a cell administration position includes a combination of a distance between an administration position and a brain surface, a distance between an administration position and a damage position, a distance between an administration position and an edema area, and whether the administration position is a site other than the site referred to as the eloquent area in cerebral arteriovenous malformation (AVM).

(Item 56)

The method according to any one of items 53 to 55, wherein the cell administration position is identified by one or more of the methods according to items 1 to 14.

(Item 57)

A method of predicting the probability of occurrence of adverse effects of cell therapy on a central nervous system disorder in a subject, the method comprising:
- 1) inputting a group of data indicating a passing region for an administration needle for administering cells, and data on adverse effects of cell therapy for each passing region for an administration needle for administering cells, into an artificial intelligence model as learning data, and causing the artificial intelligence model to learn the learning data;
- 2) acquiring a group of data indicating a passing region for an administration needle for administering cells;
- 3) inputting the group of data indicating a passing region for an administration needle for administering cells acquired in the 2) into the learned artificial intelligence model;
- 4) causing the learned artificial intelligence model to calculate the probability of occurrence of adverse effects of cell therapy.

(Item 58)

The method according to item 57, wherein the group of data indicating a passing region for an administration needle for administering cells includes at least one of: a distance between the cranial bone and the brain surface directly below the skin through which an administration needle passes; whether the eloquent area is directly below an insertion point of an administration needle; whether there is a thick vein directly below an insertion point of an administration needle; whether an administration needle passes through an artificial object, such as an artificial bone, an artificial dura mater or a titanium plate; a distance between the sulcus and an administration needle; and a distance between an administration needle and a thick blood vessel in the brain.

(Item 59)

The method according to item 57 or 58, wherein the group of data indicating a passing region for an administration needle for administering cells includes a combination of: a distance between the cranial bone and the brain surface directly below the skin through which an administration needle passes; whether the eloquent area is directly below an insertion point of an administration needle; whether there is a thick vein directly below an insertion point of an administration needle; whether an administration needle passes through an artificial object, such as an artificial bone, an artificial dura mater or a titanium plate; a distance between the sulcus and an administration needle; and a distance between an administration needle and a thick blood vessel in the brain.

(Item 60)

The method according to any one of items 57 to 59, wherein the cell administration position is identified by one or more of the methods according to items 15 to 25.

(Item 61)

A method of predicting the probability of occurrence of adverse effects of cell therapy on a central nervous system disorder in a subject, the method comprising:
- 1) inputting a group of data indicating a cell administration position and a group of data indicating a passing region for an administration needle for administering cells to a cell administration position, and the group of data indicating a cell administration position and data on adverse effects of cell therapy for each passing region for the administration needle for administering cells to the cell administration position, into an artificial intelligence model as learning data, and causing the artificial intelligence model to learn the learning data;
2) acquiring a group of data indicating a cell administration position and a group of data indicating a passing region for an administration needle for administering cells to a cell administration position;
3) inputting the group of data indicating a cell administration position and the group of data indicating a passing region for an administration needle for administering cells to a cell administration position acquired in the 2) into the learned artificial intelligence model;
4) causing the learned artificial intelligence model to calculate the probability of occurrence of adverse effects of cell therapy.

(Item 62)

The method according to item 61, wherein the group of data indicating a cell administration position includes a combination of a distance between an administration position and a brain surface, a distance between an administration position and a damage position, a distance between an administration position and an edema area, and whether the administration position is a site other than the site referred to as the eloquent area in cerebral arteriovenous malformation (AVM).

(Item 63)

The method according to either one of items 61 and 62, wherein the group of data indicating a passing region for an administration needle for administering cells to a cell administration position includes a combination of: a distance between the cranial bone and the brain surface directly below the skin through which an administration needle passes; whether the eloquent area is directly below an insertion point of an administration needle; whether there is a thick vein directly below an insertion point of an administration needle; whether an administration needle passes through an artificial object, such as an artificial bone, an artificial dura mater or a titanium plate; a distance between the sulcus and an administration needle; and a distance between an administration needle and a thick blood vessel in the brain.

(Item 64)

The method according to any one of items 61 to 63,
wherein the group of data indicating a cell administration position includes at least one of: a distance between an administration position and a brain surface, a distance between an administration position and a damage position, a distance between an administration position and an edema area, and whether the administration position is a site other than the site referred to as the eloquent area in cerebral arteriovenous malformation (AVM), and
wherein the group of data indicating a passing region for an administration needle for administering cells to a cell administration position includes at least one of: a distance between the cranial bone and the brain surface directly below the skin through which an administration needle passes; whether the eloquent area is directly below an insertion point of an administration needle; whether there is a thick vein directly below an insertion point of an administration needle; whether an administration needle passes through an artificial object, such as an artificial bone, an artificial dura mater or a titanium plate; a distance between the sulcus and an administration needle; and a distance between an administration needle and a thick blood vessel in the brain.

(Item 65)

The method according to any one of items 61 to 64, wherein the cell administration position and the passing region for an administration needle for administering cells to the cell administration position are identified by one or more of the methods according to items 26 to 52.

(Item 66)

The method according to any one of items 53 to 65, wherein the adverse effects are adverse effects on motor function, sensory function, language function or vision, or blood loss.

(Item 67)

A program that causes a computer to execute a method of predicting the probability of occurrence of adverse effects of cell therapy on a central nervous system disorder in a subject, the method comprising:
1) inputting a group of data indicating a cell administration position and data on the occurrence of adverse effects of cell therapy for each cell administration position into an artificial intelligence model as learning data and causing the artificial intelligence model to learn the learning data;
2) acquiring a group of data indicating a cell administration position;
3) inputting the group of data indicating a cell administration position acquired in the 2) into the learned artificial intelligence model; and
4) causing the learned artificial intelligence model to calculate the probability of occurrence of adverse effects of cell therapy.

(Item 68)

The program according to item 67, wherein the group of data indicating a cell administration position includes data on at least one of a distance between an administration position and a brain surface, a distance between an administration position and a damage position, a distance between an administration position and an edema area, and whether the administration position is a site other than the site referred to as the eloquent area in cerebral arteriovenous malformation (AVM).

(Item 69)

The program according to item 67 or 68, wherein the group of data indicating a cell administration position includes a combination of a distance between an administration position and a brain surface, a distance between an administration position and a damage position, a distance between an administration position and an edema area, and whether the administration position is a site other than the site referred to as the eloquent area in cerebral arteriovenous malformation (AVM).

(Item 70)

The program according to any one of items 67 to 69, wherein the cell administration position is identified by one or more of the methods according to items 1 to 14.

(Item 71)

A program that causes a computer to execute a method of predicting the probability of occurrence of adverse effects of cell therapy on a central nervous system disorder in a subject, the method comprising:
1) inputting a group of data indicating a passing region for an administration needle for administering cells, and data on adverse effects of cell therapy for each passing region for an administration needle for administering cells, into an artificial intelligence model as learning data, and causing the artificial intelligence model to learn the learning data;

2) acquiring a group of data indicating a passing region for an administration needle for administering cells;

3) inputting the group of data indicating a passing region for an administration needle for administering cells acquired in the 2) into the learned artificial intelligence model;

4) causing the learned artificial intelligence model to calculate the probability of occurrence of adverse effects of cell therapy.

(Item 72)

The program according to item 71, wherein the group of data indicating a passing region for an administration needle for administering cells includes at least one of: a distance between the cranial bone and the brain surface directly below the skin through which an administration needle passes; whether the eloquent area is directly below an insertion point of an administration needle; whether there is a thick vein directly below an insertion point of an administration needle; whether an administration needle passes through an artificial object, such as an artificial bone, an artificial dura mater or a titanium plate; a distance between the sulcus and an administration needle; and a distance between an administration needle and a thick blood vessel in the brain.

(Item 73)

The program according to item 71 or 72, wherein the group of data indicating a passing region for an administration needle for administering cells includes a combination of: a distance between the cranial bone and the brain surface directly below the skin through which an administration needle passes; whether the eloquent area is directly below an insertion point of an administration needle; whether there is a thick vein directly below an insertion point of an administration needle; whether an administration needle passes through an artificial object, such as an artificial bone, an artificial dura mater or a titanium plate; a distance between the sulcus and an administration needle; and a distance between an administration needle and a thick blood vessel in the brain.

(Item 74)

The program according to any one of items 71 to 73, wherein the cell administration position is identified by one or more of the methods according to items 15 to 25.

(Item 75)

A program that causes a computer to execute a method of predicting the probability of occurrence of adverse effects of cell therapy on a central nervous system disorder in a subject, the method comprising:

1) inputting a group of data indicating a cell administration position and a group of data indicating a passing region for an administration needle for administering cells to a cell administration position, and the group of data indicating a cell administration position and data on adverse effects of cell therapy for each passing region for the administration needle for administering cells to the cell administration position, into an artificial intelligence model as learning data, and causing the artificial intelligence model to learn the learning data;

2) acquiring a group of data indicating a cell administration position and a group of data indicating a passing region for an administration needle for administering cells to a cell administration position;

3) inputting the group of data indicating a cell administration position and the group of data indicating a passing region for an administration needle for administering cells to a cell administration position acquired in the 2) into the learned artificial intelligence model;

4) causing the learned artificial intelligence model to calculate the probability of occurrence of adverse effects of cell therapy.

(Item 76)

The program according to item 75, wherein the group of data indicating a cell administration position includes a combination of a distance between an administration position and a brain surface, a distance between an administration position and a damage position, a distance between an administration position and an edema area, and whether the administration position is a site other than the site referred to as the eloquent area in cerebral arteriovenous malformation (AVM).

(Item 77)

The program according to either one of items 75 and 76, wherein the group of data indicating a passing region for an administration needle for administering cells to a cell administration position includes a combination of: a distance between the cranial bone and the brain surface directly below the skin through which an administration needle passes; whether the eloquent area is directly below an insertion point of an administration needle; whether there is a thick vein directly below an insertion point of an administration needle; whether an administration needle passes through an artificial object, such as an artificial bone, an artificial dura mater or a titanium plate; a distance between the sulcus and an administration needle; and a distance between an administration needle and a thick blood vessel in the brain.

(Item 78)

The program according to any one of items 75 to 77,
wherein the group of data indicating a cell administration position includes at least one of: a distance between an administration position and a brain surface, a distance between an administration position and a damage position, a distance between an administration position and an edema area, and whether the administration position is a site other than the site referred to as the eloquent area in cerebral arteriovenous malformation (AVM), and
wherein the group of data indicating a passing region for an administration needle for administering cells to a cell administration position includes at least one of: a distance between the cranial bone and the brain surface directly below the skin through which an administration needle passes; whether the eloquent area is directly below an insertion point of an administration needle; whether there is a thick vein directly below an insertion point of an administration needle; whether an administration needle passes through an artificial object, such as an artificial bone, an artificial dura mater or a titanium plate; a distance between the sulcus and an administration needle; and a distance between an administration needle and a thick blood vessel in the brain.

(Item 79)

The program according to any one of items 75 to 78, wherein the cell administration position and the passing region for an administration needle for administering cells to the cell administration position are identified by one or more of the methods according to items 26 to 52.

(Item 80)

The program according to any one of items 67 to 79, wherein the adverse effects are adverse effects on motor function, sensory function, language function or vision, or blood loss.

(Item 81)

A recording medium having a program stored thereon that causes a computer to execute a method of predicting the probability of occurrence of adverse effects of cell therapy on a central nervous system disorder in a subject, the method comprising:

1) inputting a group of data indicating a cell administration position and data on the occurrence of adverse effects of cell therapy for each cell administration position into an artificial intelligence model as learning data and causing the artificial intelligence model to learn the learning data;
2) acquiring a group of data indicating a cell administration position;
3) inputting the group of data indicating a cell administration position acquired in the 2) into the learned artificial intelligence model; and
4) causing the learned artificial intelligence model to calculate the probability of occurrence of adverse effects of cell therapy.

(Item 82)

The recording medium according to item 81, wherein the group of data indicating a cell administration position includes data on at least one of a distance between an administration position and a brain surface, a distance between an administration position and a damage position, a distance between an administration position and an edema area, and whether the administration position is a site other than the site referred to as the eloquent area in cerebral arteriovenous malformation (AVM).

(Item 83)

The recording medium according to item 67 or 82, wherein the group of data indicating a cell administration position includes a combination of a distance between an administration position and a brain surface, a distance between an administration position and a damage position, a distance between an administration position and an edema area, and whether the administration position is a site other than the site referred to as the eloquent area in cerebral arteriovenous malformation (AVM).

(Item 84)

The recording medium according to any one of items 81 to 83, wherein the cell administration position is identified by one or more of the methods according to items 1 to 14.

(Item 85)

A recording medium having a program stored thereon that causes a computer to execute a method of predicting the probability of occurrence of adverse effects of cell therapy on a central nervous system disorder in a subject, the method comprising:

1) inputting a group of data indicating a passing region for an administration needle for administering cells, and data on adverse effects of cell therapy for each passing region for an administration needle for administering cells, into an artificial intelligence model as learning data, and causing the artificial intelligence model to learn the learning data;
2) acquiring a group of data indicating a passing region for an administration needle for administering cells;
3) inputting the group of data indicating a passing region for an administration needle for administering cells acquired in the 2) into the learned artificial intelligence model;
4) causing the learned artificial intelligence model to calculate the probability of occurrence of adverse effects of cell therapy.

(Item 86)

The recording medium according to item 85, wherein the group of data indicating a passing region for an administration needle for administering cells includes at least one of: a distance between the cranial bone and the brain surface directly below the skin through which an administration needle passes; whether the eloquent area is directly below an insertion point of an administration needle; whether there is a thick vein directly below an insertion point of an administration needle; whether an administration needle passes through an artificial object, such as an artificial bone, an artificial dura mater or a titanium plate; a distance between the sulcus and an administration needle; and a distance between an administration needle and a thick blood vessel in the brain.

(Item 87)

The recording medium according to item 85 or 86, wherein the group of data indicating a passing region for an administration needle for administering cells includes a combination of: a distance between the cranial bone and the brain surface directly below the skin through which an administration needle passes; whether the eloquent area is directly below an insertion point of an administration needle; whether there is a thick vein directly below an insertion point of an administration needle; whether an administration needle passes through an artificial object, such as an artificial bone, an artificial dura mater or a titanium plate; a distance between the sulcus and an administration needle; and a distance between an administration needle and a thick blood vessel in the brain.

(Item 88)

The recording medium according to any one of items 85 to 87, wherein the cell administration position is identified by one or more of the methods according to items 15 to 25.

(Item 89)

A recording medium having a program stored thereon that causes a computer to execute a method of predicting the probability of occurrence of adverse effects of cell therapy on a central nervous system disorder in a subject, the method comprising:

1) inputting a group of data indicating a cell administration position and a group of data indicating a passing region for an administration needle for administering cells to a cell administration position, and the group of data indicating a cell administration position and data on adverse effects of cell therapy for each passing region for the administration needle for administering cells to the cell administration position, into an artificial intelligence model as learning data, and causing the artificial intelligence model to learn the learning data;
2) acquiring a group of data indicating a cell administration position and a group of data indicating a passing region for an administration needle for administering cells to a cell administration position;
3) inputting the group of data indicating a cell administration position and the group of data indicating a passing region for an administration needle for administering cells to a cell administration position acquired in the 2) into the learned artificial intelligence model;

4) causing the learned artificial intelligence model to calculate the probability of occurrence of adverse effects of cell therapy.

(Item 90)

The recording medium according to item 89, wherein the group of data indicating a cell administration position includes a combination of a distance between an administration position and a brain surface, a distance between an administration position and a damage position, a distance between an administration position and an edema area, and whether the administration position is a site other than the site referred to as the eloquent area in cerebral arteriovenous malformation (AVM).

(Item 91)

The recording medium according to either one of items 89 and 90, wherein the group of data indicating a passing region for an administration needle for administering cells to a cell administration position includes a combination of: a distance between the cranial bone and the brain surface directly below the skin through which an administration needle passes; whether the eloquent area is directly below an insertion point of an administration needle; whether there is a thick vein directly below an insertion point of an administration needle; whether an administration needle passes through an artificial object, such as an artificial bone, an artificial dura mater or a titanium plate; a distance between the sulcus and an administration needle; and a distance between an administration needle and a thick blood vessel in the brain.

(Item 92)

The recording medium according to any one of items 89 to 91,
wherein the group of data indicating a cell administration position includes at least one of: a distance between an administration position and a brain surface, a distance between an administration position and a damage position, a distance between an administration position and an edema area, and whether the administration position is a site other than the site referred to as the eloquent area in cerebral arteriovenous malformation (AVM), and
wherein the group of data indicating a passing region for an administration needle for administering cells to a cell administration position includes at least one of: a distance between the cranial bone and the brain surface directly below the skin through which an administration needle passes; whether the eloquent area is directly below an insertion point of an administration needle; whether there is a thick vein directly below an insertion point of an administration needle; whether an administration needle passes through an artificial object, such as an artificial bone, an artificial dura mater or a titanium plate; a distance between the sulcus and an administration needle; and a distance between an administration needle and a thick blood vessel in the brain.

(Item 93)

The recording medium according to any one of items 89 to 92, wherein the cell administration position and the passing region for an administration needle for administering cells to the cell administration position are identified by one or more of the methods according to items 26 to 52.

(Item 94)

The recording medium according to any one of items 81 to 93, wherein the adverse effects are adverse effects on motor function, sensory function, language function or vision, or blood loss.

(Item 95)

A system of predicting the probability of occurrence of adverse effects of cell therapy on a central nervous system disorder in a subject, the system comprising:
1) a learning section for inputting a group of data indicating a cell administration position and data on the occurrence of adverse effects of cell therapy for each cell administration position into an artificial intelligence model as learning data and causing the artificial intelligence model to learn the learning data;
2) an acquiring section for acquiring a group of data indicating a cell administration position;
3) an inputting section for inputting the group of data indicating a cell administration position acquired in the 2) into the learned artificial intelligence model; and
4) a calculating section for causing the learned artificial intelligence model to calculate the probability of occurrence of adverse effects of cell therapy.

(Item 96)

The system according to item 95, wherein the group of data indicating a cell administration position includes data on at least one of a distance between an administration position and a brain surface, a distance between an administration position and a damage position, a distance between an administration position and an edema area, and whether the administration position is a site other than the site referred to as the eloquent area in cerebral arteriovenous malformation (AVM).

(Item 97)

The system according to item 95 or 96, wherein the group of data indicating a cell administration position includes a combination of a distance between an administration position and a brain surface, a distance between an administration position and a damage position, a distance between an administration position and an edema area, and whether the administration position is a site other than the site referred to as the eloquent area in cerebral arteriovenous malformation (AVM).

(Item 98)

The system according to any one of items 95 to 97, wherein the cell administration position is identified by one or more of the methods according to items 1 to 14.

(Item 99)

A system of predicting the probability of occurrence of adverse effects of cell therapy on a central nervous system disorder in a subject, the system comprising:
1) a learning section for inputting a group of data indicating a passing region for an administration needle for administering cells, and data on adverse effects of cell therapy for each passing region for an administration needle for administering cells, into an artificial intelligence model as learning data, and causing the artificial intelligence model to learn the learning data;
2) acquiring a group of data indicating a passing region for an administration needle for administering cells;
3) an inputting section for inputting the group of data indicating a passing region for an administration needle for administering cells acquired in the 2) into the learned artificial intelligence model;
4) a calculating section for causing the learned artificial intelligence model to calculate the probability of occurrence of adverse effects of cell therapy.

(Item 100)

The system according to item 99, wherein the group of data indicating a passing region for an administration needle for administering cells includes at least one of: a distance between the cranial bone and the brain surface directly below the skin through which an administration needle passes; whether the eloquent area is directly below an insertion point of an administration needle; whether there is a thick vein directly below an insertion point of an administration needle; whether an administration needle passes through an artificial object, such as an artificial bone, an artificial dura mater or a titanium plate; a distance between the sulcus and an administration needle; and a distance between an administration needle and a thick blood vessel in the brain.

(Item 101)

The system according to item 99 or 100, wherein the group of data indicating a passing region for an administration needle for administering cells includes a combination of: a distance between the cranial bone and the brain surface directly below the skin through which an administration needle passes; whether the eloquent area is directly below an insertion point of an administration needle; whether there is a thick vein directly below an insertion point of an administration needle; whether an administration needle passes through an artificial object, such as an artificial bone, an artificial dura mater or a titanium plate; a distance between the sulcus and an administration needle; and a distance between an administration needle and a thick blood vessel in the brain.

(Item 102)

The system according to any one of items 99 to 101, wherein the cell administration position is identified by one or more of the methods according to items 15 to 25.

(Item 103)

A system of predicting the probability of occurrence of adverse effects of cell therapy on a central nervous system disorder in a subject, the system comprising:
1) a learning section for inputting a group of data indicating a cell administration position and a group of data indicating a passing region for an administration needle for administering cells to a cell administration position, and the group of data indicating a cell administration position and data on adverse effects of cell therapy for each passing region for the administration needle for administering cells to the cell administration position, into an artificial intelligence model as learning data, and causing the artificial intelligence model to learn the learning data;
2) an acquiring section for acquiring a group of data indicating a cell administration position and a group of data indicating a passing region for an administration needle for administering cells to a cell administration position;
3) an inputting section for inputting the group of data indicating a cell administration position and the group of data indicating a passing region for an administration needle for administering cells to a cell administration position acquired in the 2) into the learned artificial intelligence model;
4) a calculating section for causing the learned artificial intelligence model to calculate the probability of occurrence of adverse effects of cell therapy.

(Item 104)

The system according to item 103, wherein the group of data indicating a cell administration position includes a combination of a distance between an administration position and a brain surface, a distance between an administration position and a damage position, a distance between an administration position and an edema area, and whether the administration position is a site other than the site referred to as the eloquent area in cerebral arteriovenous malformation (AVM).

(Item 105)

The system according to either one of items 103 and 104, wherein the group of data indicating a passing region for an administration needle for administering cells to a cell administration position includes a combination of: a distance between the cranial bone and the brain surface directly below the skin through which an administration needle passes; whether the eloquent area is directly below an insertion point of an administration needle; whether there is a thick vein directly below an insertion point of an administration needle; whether an administration needle passes through an artificial object, such as an artificial bone, an artificial dura mater or a titanium plate; a distance between the sulcus and an administration needle; and a distance between an administration needle and a thick blood vessel in the brain.

(Item 106)

The system according to any one of items 93 to 105,
wherein the group of data indicating a cell administration position includes at least one of: a distance between an administration position and a brain surface, a distance between an administration position and a damage position, a distance between an administration position and an edema area, and whether the administration position is a site other than the site referred to as the eloquent area in cerebral arteriovenous malformation (AVM), and
wherein the group of data indicating a passing region for an administration needle for administering cells to a cell administration position includes at least one of: a distance between the cranial bone and the brain surface directly below the skin through which an administration needle passes; whether the eloquent area is directly below an insertion point of an administration needle; whether there is a thick vein directly below an insertion point of an administration needle; whether an administration needle passes through an artificial object, such as an artificial bone, an artificial dura mater or a titanium plate; a distance between the sulcus and an administration needle; and a distance between an administration needle and a thick blood vessel in the brain.

(Item 107)

The system according to any one of items 93 to 106, wherein the cell administration position and the passing region for an administration needle for administering cells to the cell administration position are identified by one or more of the methods according to items 26 to 52.

(Item 108)

The system according to any one of items 95 to 107, wherein the adverse effects are adverse effects on motor function, sensory function, language function or vision, or blood loss.

(Item A1)

A method for identifying a site of administration of cells in cell therapy for a central nervous system disorder in a subject, the method comprising:
X) inputting a group of image data on at least part of the brain of the subject and a group of data on a cell administration site into an artificial intelligence model as learning data and causing the artificial intelligence model to learn the learning data;
A) acquiring, by an imaging device, image data on at least part of the brain of the subject;

Y) inputting the image data on at least part of the brain of the subject acquired in the A) into the learned artificial intelligence model; and Z) causing the learned artificial intelligence model to calculate the data on the cell administration site.

(Item A2)

The method according to item A1, further comprising:

B) obtaining information on the brain of the subject by a computer device in communication with the imaging device;

C) depicting motor fibers by the computer device using the acquired image data and data on the brain of the subject;

D) identifying, by the computer device, a damage position in which the motor fibers are damaged, which identifies a part where running data on the motor fibers is lower than other sites to identify the lower part as damaged motor fibers; and F) outputting the calculated administration site as a graphic display.

(Item A3)

The method according to item A1 or A2, wherein the image data on at least part of the brain of the subject includes at least one of: running data on the motor fibers of the subject; data on a damage position in which the motor fibers are damaged; data on a position of the brain surface of the subject; data on an edema region of the subject; and data on a site referred to as the eloquent area in cerebral arteriovenous malformation (AVM) of the subject.

(Item A4)

The method according to any one of items A1 to A3, wherein the image data on at least part of the brain of the subject includes a combination of: running data on the motor fibers of the subject; data on a damage position in which the motor fibers are damaged; data on a position of the brain surface of the subject; data on an edema region of the subject; and data on a site referred to as the eloquent area in cerebral arteriovenous malformation (AVM) of the subject.

(Item A5)

The method according to any one of items A1 to A4, further comprising one or more of features according to items 1 to 14.

(Item A6)

A program that causes a computer to execute a method for identifying a cell administration site in cell therapy for a central nervous system disorder in a subject, the method comprising:

X) inputting a group of image data on at least part of the brain of the subject and a group of data on a cell administration site into an artificial intelligence model as learning data and causing the artificial intelligence model to learn the learning data;

A) acquiring, by an imaging device, image data on at least part of the brain of the subject;

Y) inputting the image data on at least part of the brain of the subject acquired in the A) into the learned artificial intelligence model; and Z) causing the learned artificial intelligence model to calculate the data on the cell administration site.

(Item A7)

The program according to item A6, wherein the method further comprises:

B) obtaining information on the brain of the subject by a computer device in communication with the imaging device;

C) depicting motor fibers by the computer device using the acquired image data and data on the brain of the subject;

D) identifying, by the computer device, a damage position in which the motor fibers are damaged, which identifies a part where running data on the motor fibers is lower than other sites to identify the lower part as damaged motor fibers; and F) outputting the calculated administration site as a graphic display.

(Item A8)

The program according to item A6 or A7, wherein the image data on at least part of the brain of the subject includes at least one of: running data on the motor fibers of the subject; data on a damage position in which the motor fibers are damaged; data on a position of the brain surface of the subject; data on an edema region of the subject; and data on a site referred to as the eloquent area in cerebral arteriovenous malformation (AVM) of the subject.

(Item A9)

The program according to any one of items A6 to A8, wherein the image data on at least part of the brain of the subject includes a combination of: running data on the motor fibers of the subject; data on a damage position in which the motor fibers are damaged; data on a position of the brain surface of the subject; data on an edema region of the subject; and data on a site referred to as the eloquent area in cerebral arteriovenous malformation (AVM) of the subject.

(Item A10)

The program according to any one of items A6 to A9, further comprising one or more of features according to items 1 to 14.

(Item A11)

A recording medium having a program stored thereon that causes a computer to execute a method for identifying a cell administration site in cell therapy for a central nervous system disorder in a subject, the method comprising:

X) inputting a group of image data on at least part of the brain of the subject and a group of data on a cell administration site into an artificial intelligence model as learning data and causing the artificial intelligence model to learn the learning data;

A) acquiring, by an imaging device, image data on at least part of the brain of the subject;

Y) inputting the image data on at least part of the brain of the subject acquired in the A) into the learned artificial intelligence model; and Z) causing the learned artificial intelligence model to calculate the data on the cell administration site.

(Item A12)

The recording medium according to item A11, wherein the method further comprises:

B) obtaining information on the brain of the subject by a computer device in communication with the imaging device;

C) depicting motor fibers by the computer device using the acquired image data and data on the brain of the subject;

D) identifying, by the computer device, a damage position in which the motor fibers are damaged, which identifies a part where running data on the motor fibers is lower than other sites to identify the lower part as damaged motor fibers; and F) outputting the calculated administration site as a graphic display.

(Item A13)

The recording medium according to item A11 or A12, wherein the image data on at least part of the brain of the subject includes at least one of: running data on the motor fibers of the subject; data on a damage position in which the motor fibers are damaged; data on a position of the brain surface of the subject; data on an edema region of the subject; and data on a site referred to as the eloquent area in cerebral arteriovenous malformation (AVM) of the subject.

(Item A14)

The recording medium according to any one of items A11 to A13, wherein the image data on at least part of the brain of the subject includes a combination of: running data on the motor fibers of the subject; data on a damage position in which the motor fibers are damaged; data on a position of the brain surface of the subject; data on an edema region of the subject; and data on a site referred to as the eloquent area in cerebral arteriovenous malformation (AVM) of the subject.

(Item A15)

The recording medium according to any one of items A11 to A14, further comprising one or more of features according to items 1 to 14.

(Item A16)

A system for identifying a cell administration site in cell therapy for a central nervous system disorder in a subject, the system comprising:
- X) a learning section for inputting a group of image data on at least part of the brain of the subject and a group of data on a cell administration site into an artificial intelligence model as learning data and causing the artificial intelligence model to learn the learning data;
- A) an acquiring section for acquiring, by an imaging device, image data on at least part of the brain of the subject;
- Y) an inputting section for inputting the image data on at least part of the brain of the subject acquired in the A) into the learned artificial intelligence model; and
- Z) a calculating section for causing the learned artificial intelligence model to calculate the data on the cell administration site.

(Item A17)

The system according to item A16, further comprising:
- B) an obtaining section for obtaining information on the brain of the subject by a computer device in communication with the imaging device;
- C) a depicting section for depicting motor fibers by the computer device using the acquired image data and data on the brain of the subject;
- D) an identifying section for identifying, by the computer device, a damage position in which the motor fibers are damaged, which identifies a part where running data on the motor fibers is lower than other sites to identify the lower part as damaged motor fibers; and
- F) an outputting section for outputting the calculated administration site as a graphic display.

(Item A18)

The system according to item A16 or A17, wherein the image data on at least part of the brain of the subject includes at least one of: running data on the motor fibers of the subject; data on a damage position in which the motor fibers are damaged; data on a position of the brain surface of the subject; data on an edema region of the subject; and data on a site referred to as the eloquent area in cerebral arteriovenous malformation (AVM) of the subject.

(Item A19)

The system according to any one of items A16 to A18, wherein the image data on at least part of the brain of the subject includes a combination of: running data on the motor fibers of the subject; data on a damage position in which the motor fibers are damaged; data on a position of the brain surface of the subject; data on an edema region of the subject; and data on a site referred to as the eloquent area in cerebral arteriovenous malformation (AVM) of the subject.

(Item A20)

The system according to any one of items A16 to A19, further comprising one or more of features according to items 1 to 14.

(Item B1)

A method for identifying a passing region for an administration needle for administration of cells in cell therapy for a central nervous system disorder in a subject, the method comprising:
- (X) inputting a group of image data on at least part of the brain of the subject and a group of data on a passing region for an administration needle for administering cells into an artificial intelligence model as learning data and causing the artificial intelligence model to learn the learning data;
- (A) acquiring image data on at least part of the brain of the subject using an imaging device;
- (Y) inputting the image data on at least part of the brain of the subject acquired in the (A) into the learned artificial intelligence model; and
- (Z) causing the learned artificial intelligence model to calculate the data on a passing region for an administration needle for administering cells.

(Item B2)

The method according to item B1, further comprising:
- (B) obtaining information on the brain of the subject by a computer device in communication with the imaging device;
- (C) depicting a blood vessel by the computer device based on the acquired image data and information about the brain of the subject;
- (D) identifying, by the computer device, a route range that does not allow penetration of the blood vessel;
- (E) identifying, by the computer device, a sulcus non-invasive range where a needle does not come out of the sulcus after the needle is inserted into the brain; and
- (G) outputting the calculated route as a graphic display.

(Item B3)

The method according to item B1 or B2, wherein the image data on at least part of the brain of the subject includes at least one of: running data on the motor fibers of the subject; data on a position of a brain sulcus of the patient; data on a distance between a brain surface and a cranial bone of the patient; data on a site referred to as the eloquent area in cerebral arteriovenous malformation (AVM) of the subject; data on a position of an artificial object, such as an artificial bone, an artificial dura mater or a titanium plate; data on a position of a thick artery directly below the skin; and data on a position of a thick blood vessel in the brain.

(Item B4)

The method according to any one of items B1 to B3, wherein the image data on at least part of the brain of the subject includes a combination of: running data on the motor fibers of the subject; data on a position of a brain sulcus of the patient; data on a distance between a brain surface and a cranial bone of the patient; data on a site referred to as the eloquent area in cerebral arteriovenous malformation (AVM) of the subject; data on a position of an artificial object, such as an artificial bone, an artificial dura mater or a titanium plate; data on a position of a thick artery directly below the skin; and data on a position of a thick blood vessel in the brain.

(Item B5)

The method according to any one of items B1 to B4, further comprising one or more of features according to items 15 to 25.

(Item B6)

A program that causes a computer to execute a method for identifying a passing region for an administration needle for administration of cells in cell therapy for a central nervous system disorder in a subject, the method comprising:
- (X) inputting a group of image data on at least part of the brain of the subject and a group of data on a passing region for an administration needle for administering cells into an artificial intelligence model as learning data and causing the artificial intelligence model to learn the learning data;
- (A) acquiring image data on at least part of the brain of the subject using an imaging device;
- (Y) inputting the image data on at least part of the brain of the subject acquired in the (A) into the learned artificial intelligence model; and
- (Z) causing the learned artificial intelligence model to calculate the data on a passing region for an administration needle for administering cells.

(Item B7)

The program according to item B6, wherein the method further comprises:
- (B) obtaining information on the brain of the subject by a computer device in communication with the imaging device;
- (C) depicting a blood vessel by the computer device based on the acquired image data and information about the brain of the subject;
- (D) identifying, by the computer device, a route range that does not allow penetration of the blood vessel;
- (E) identifying, by the computer device, a sulcus non-invasive range where a needle does not come out of the sulcus after the needle is inserted into the brain; and
- (G) outputting the calculated route as a graphic display.

(Item B8)

The program according to item B6 or B7, wherein the image data on at least part of the brain of the subject includes at least one of: running data on the motor fibers of the subject; data on a position of a brain sulcus of the patient; data on a distance between a brain surface and a cranial bone of the patient; data on a site referred to as the eloquent area in cerebral arteriovenous malformation (AVM) of the subject; data on a position of an artificial object, such as an artificial bone, an artificial dura mater or a titanium plate; data on a position of a thick artery directly below the skin; and data on a position of a thick blood vessel in the brain.

(Item B9)

The program according to any one of items B6 to B8, wherein the image data on at least part of the brain of the subject includes a combination of: running data on the motor fibers of the subject; data on a position of a brain sulcus of the patient; data on a distance between a brain surface and a cranial bone of the patient; data on a site referred to as the eloquent area in cerebral arteriovenous malformation (AVM) of the subject; data on a position of an artificial object, such as an artificial bone, an artificial dura mater or a titanium plate; data on a position of a thick artery directly below the skin; and data on a position of a thick blood vessel in the brain.

(Item B10)

The program according to any one of items B6 to B9, further comprising one or more of features according to items 15 to 25.

(Item B11)

A recording medium having a program stored thereon that causes a computer to execute a method for identifying a passing region for an administration needle for administration of cells in cell therapy for a central nervous system disorder in a subject, the method comprising:
- (X) inputting a group of image data on at least part of the brain of the subject and a group of data on a passing region for an administration needle for administering cells into an artificial intelligence model as learning data and causing the artificial intelligence model to learn the learning data;
- (A) acquiring image data on at least part of the brain of the subject using an imaging device;
- (Y) inputting the image data on at least part of the brain of the subject acquired in the (A) into the learned artificial intelligence model; and
- (Z) causing the learned artificial intelligence model to calculate the data on a passing region for an administration needle for administering cells.

(Item B12)

The recording medium according to item B11, wherein the method further comprises:
- (B) obtaining information on the brain of the subject by a computer device in communication with the imaging device;
- (C) depicting a blood vessel by the computer device based on the acquired image data and information about the brain of the subject;
- (D) identifying, by the computer device, a route range that does not allow penetration of the blood vessel;
- (E) identifying, by the computer device, a sulcus non-invasive range where a needle does not come out of the sulcus after the needle is inserted into the brain; and
- (G) outputting the calculated route as a graphic display.

(Item B13)

The recording medium according to item B11 or B12, wherein the image data on at least part of the brain of the subject includes at least one of: running data on the motor fibers of the subject; data on a position of a brain sulcus of the patient; data on a distance between a brain surface and a cranial bone of the patient; data on a site referred to as the eloquent area in cerebral arteriovenous malformation (AVM) of the subject; data on a position of an artificial object, such as an artificial bone, an artificial dura mater or a titanium plate; data on a position of a thick artery directly below the skin; and data on a position of a thick blood vessel in the brain.

(Item B14)

The recording medium according to any one of items B11 to B13, wherein the image data on at least part of the brain of the subject includes a combination of: running data on the motor fibers of the subject; data on a position of a brain sulcus of the patient; data on a distance between a brain surface and a cranial bone of the patient; data on a site referred to as the eloquent area in cerebral arteriovenous malformation (AVM) of the subject; data on a position of an artificial object, such as an artificial bone, an artificial dura mater or a titanium plate; data on a position of a thick artery directly below the skin; and data on a position of a thick blood vessel in the brain.

(Item B15)

The recording medium according to any one of items B11 to B14, further comprising one or more of features according to items 15 to 25.

(Item B16)

A system for identifying a passing region for an administration needle for administration of cells in cell therapy for a central nervous system disorder in a subject, the system comprising:
- (X) a learning section for inputting a group of image data on at least part of the brain of the subject and a group of data on a passing region for an administration needle for administering cells into an artificial intelligence model as learning data and causing the artificial intelligence model to learn the learning data;
- (A) an acquiring section for acquiring image data on at least part of the brain of the subject using an imaging device;
- (Y) an inputting section for inputting the image data on at least part of the brain of the subject acquired in the (A) into the learned artificial intelligence model; and
- (Z) a calculating section for causing the learned artificial intelligence model to calculate the data on a passing region for an administration needle for administering cells.

(Item B17)

The system according to item B16, further comprising:
- (B) an obtaining section for obtaining information on the brain of the subject by a computer device in communication with the imaging device;
- (C) a depicting section for depicting a blood vessel by the computer device based on the acquired image data and information about the brain of the subject;
- (D) a route range identifying section for identifying, by the computer device, a route range that does not allow penetration of the blood vessel;
- (E) a sulcus non-invasive range identifying section for identifying, by the computer device, a sulcus non-invasive range where a needle does not come out of the sulcus after the needle is inserted into the brain; and
- (G) an outputting section for outputting the calculated route as a graphic display.

(Item B18)

The system according to item B16 or B17, wherein the image data on at least part of the brain of the subject includes at least one of: running data on the motor fibers of the subject; data on a position of a brain sulcus of the patient; data on a distance between a brain surface and a cranial bone of the patient; data on a site referred to as the eloquent area in cerebral arteriovenous malformation (AVM) of the subject; data on a position of an artificial object, such as an artificial bone, an artificial dura mater or a titanium plate; data on a position of a thick artery directly below the skin; and data on a position of a thick blood vessel in the brain.

(Item B19)

The system according to any one of items B16 to B18, wherein the image data on at least part of the brain of the subject includes a combination of: running data on the motor fibers of the subject; data on a position of a brain sulcus of the patient; data on a distance between a brain surface and a cranial bone of the patient; data on a site referred to as the eloquent area in cerebral arteriovenous malformation (AVM) of the subject; data on a position of an artificial object, such as an artificial bone, an artificial dura mater or a titanium plate; data on a position of a thick artery directly below the skin; and data on a position of a thick blood vessel in the brain.

(Item B20)

The system according to any one of items B16 to B19, further comprising one or more of features according to items 15 to 25.

(Item C1)

A method for identifying a route of administration of cells in cell therapy for a central nervous system disorder in a subject, the method comprising:
- x) inputting a group of image data on at least part of the brain of the subject and a group of data on a route of administration of cells into an artificial intelligence model as learning data and causing the artificial intelligence model to learn the learning data;
- i) acquiring, by an imaging device, image data on at least part of the brain of the subject;
- y) inputting the image data on at least part of the brain of the subject acquired in the i) into the learned artificial intelligence model; and
- z) causing the learned artificial intelligence model to calculate the data on the route of administration of cells.

(Item C2)

The method according to item C1, further comprising:
- ii) obtaining information on the brain of the subject by a computer device in communication with the imaging device;
- iii) providing a candidate for a route of administration of cells by the following procedure, the providing step comprising:
  - aa) selecting, by the computer device, a safe region near a damage position as an administration site;
  - bb) identifying an administration route to the selected administration site; and
  - cc) optionally, selecting, by the computer device, an excision position for passing an administration device for administering the cells in the scalp, and
- iv) outputting the selected administration site as a graphic display.

(Item C3)

The method according to item C1 or C2, wherein the image data on at least part of the brain of the subject includes at least one of: running data on the motor fibers of the subject; data on a damage position in which the motor fibers are damaged; data on a position of the brain surface of the subject; data on an edema region of the subject; and data on a site referred to as the eloquent area in cerebral arteriovenous malformation (AVM) of the subject.

(Item C4)

The method according to any one of items C1 to C3, wherein the image data on at least part of the brain of the subject includes a combination of: running data on the motor fibers of the subject; data on a damage position in which the motor fibers are damaged; data on a position of the brain surface of the subject; data on an edema region of the subject; and data on a site referred to as the eloquent area in cerebral arteriovenous malformation (AVM) of the subject.

(Item C5)

The method according to any one of items C1 to C4, wherein the image data on at least part of the brain of the subject includes at least one of: running data on the motor fibers of the subject; data on a position of a brain sulcus of the patient; data on a distance between a brain surface and a cranial bone of the patient; data on a site referred to as the eloquent area in cerebral arteriovenous malformation (AVM) of the subject; data on a position of an artificial object, such as an artificial bone, an artificial dura mater or a titanium plate; data on a position of a thick artery directly below the skin; and data on a position of a thick blood vessel in the brain.

(Item C6)

The method according to any one of items C1 to C5, wherein the image data on at least part of the brain of the subject includes a combination of: running data on the motor fibers of the subject; data on a position of a brain sulcus of the patient; data on a distance between a brain surface and a cranial bone of the patient; data on a site referred to as the eloquent area in cerebral arteriovenous malformation (AVM) of the subject; data on a position of an artificial object, such as an artificial bone, an artificial dura mater or a titanium plate; data on a position of a thick artery directly below the skin; and data on a position of a thick blood vessel in the brain.

(Item C7)

The method according to any one of items C1 to C6, further comprising one or more of features according to items 26 to 47.

(Item C8)

A program that causes a computer to execute a method for identifying a route of administration of cells in cell therapy for a central nervous system disorder in a subject, the method comprising:
  x) inputting a group of image data on at least part of the brain of the subject and a group of data on a route of administration of cells into an artificial intelligence model as learning data and causing the artificial intelligence model to learn the learning data;
  i) acquiring, by an imaging device, image data on at least part of the brain of the subject;
  y) inputting the image data on at least part of the brain of the subject acquired in the i) into the learned artificial intelligence model; and
  z) causing the learned artificial intelligence model to calculate the data on the route of administration of cells.

(Item C9)

The program according to item C8, wherein the method further comprises:
  ii) obtaining information on the brain of the subject by a computer device in communication with the imaging device;
  iii) providing a candidate for a route of administration of cells by the following procedure, the providing step comprising:
    aa) selecting, by the computer device, a safe region near a damage position as an administration site;
    bb) identifying an administration route to the selected administration site; and
    cc) optionally, selecting, by the computer device, an excision position for passing an administration device for administering the cells in the scalp, and
  iv) outputting the selected administration site as a graphic display.

(Item C10)

The program according to item C8 or C9, wherein the image data on at least part of the brain of the subject includes at least one of: running data on the motor fibers of the subject; data on a damage position in which the motor fibers are damaged; data on a position of the brain surface of the subject; data on an edema region of the subject; and data on a site referred to as the eloquent area in cerebral arteriovenous malformation (AVM) of the subject.

(Item C11)

The program according to any one of items C8 to C10, wherein the image data on at least part of the brain of the subject includes a combination of: running data on the motor fibers of the subject; data on a damage position in which the motor fibers are damaged; data on a position of the brain surface of the subject; data on an edema region of the subject; and data on a site referred to as the eloquent area in cerebral arteriovenous malformation (AVM) of the subject.

(Item C12)

The program according to any one of items C8 to C11, wherein the image data on at least part of the brain of the subject includes at least one of: running data on the motor fibers of the subject; data on a position of a brain sulcus of the patient; data on a distance between a brain surface and a cranial bone of the patient; data on a site referred to as the eloquent area in cerebral arteriovenous malformation (AVM) of the subject; data on a position of an artificial object, such as an artificial bone, an artificial dura mater or a titanium plate; data on a position of a thick artery directly below the skin; and data on a position of a thick blood vessel in the brain.

(Item C13)

The program according to any one of items C8 to C12, wherein the image data on at least part of the brain of the subject includes a combination of: running data on the motor fibers of the subject; data on a position of a brain sulcus of the patient; data on a distance between a brain surface and a cranial bone of the patient; data on a site referred to as the eloquent area in cerebral arteriovenous malformation (AVM) of the subject; data on a position of an artificial object, such as an artificial bone, an artificial dura mater or a titanium plate; data on a position of a thick artery directly below the skin; and data on a position of a thick blood vessel in the brain.

(Item C14)

The program according to any one of items C8 to C13, further comprising one or more of features according to items 26 to 47.

(Item C15)

A recording medium having a program stored thereon that causes a computer to execute a method for identifying a route of administration of cells in cell therapy for a central nervous system disorder in a subject, the method comprising:
  x) inputting a group of image data on at least part of the brain of the subject and a group of data on a route of administration of cells into an artificial intelligence model as learning data and causing the artificial intelligence model to learn the learning data;
  i) acquiring, by an imaging device, image data on at least part of the brain of the subject;
  y) inputting the image data on at least part of the brain of the subject acquired in the i) into the learned artificial intelligence model; and
  z) causing the learned artificial intelligence model to calculate the data on the route of administration of cells.

(Item C16)

The recording medium according to item C15, wherein the method further comprises:
  ii) obtaining information on the brain of the subject by a computer device in communication with the imaging device;

iii) providing a candidate for a route of administration of cells by the following procedure, the providing step comprising:
  aa) selecting, by the computer device, a safe region near a damage position as an administration site;
  bb) identifying an administration route to the selected administration site; and
  cc) optionally, selecting, by the computer device, an excision position for passing an administration device for administering the cells in the scalp, and
iv) outputting the selected administration site as a graphic display.

(Item C17)

The recording medium according to item C15 or C16, wherein the image data on at least part of the brain of the subject includes at least one of: running data on the motor fibers of the subject; data on a damage position in which the motor fibers are damaged; data on a position of the brain surface of the subject; data on an edema region of the subject; and data on a site referred to as the eloquent area in cerebral arteriovenous malformation (AVM) of the subject.

(Item C18)

The recording medium according to any one of items C15 to C17, wherein the image data on at least part of the brain of the subject includes a combination of: running data on the motor fibers of the subject; data on a damage position in which the motor fibers are damaged; data on a position of the brain surface of the subject; data on an edema region of the subject; and data on a site referred to as the eloquent area in cerebral arteriovenous malformation (AVM) of the subject.

(Item C19)

The recording medium according to any one of items C15 to C18, wherein the image data on at least part of the brain of the subject includes at least one of: running data on the motor fibers of the subject; data on a position of a brain sulcus of the patient; data on a distance between a brain surface and a cranial bone of the patient; data on a site referred to as the eloquent area in cerebral arteriovenous malformation (AVM) of the subject; data on a position of an artificial object, such as an artificial bone, an artificial dura mater or a titanium plate; data on a position of a thick artery directly below the skin; and data on a position of a thick blood vessel in the brain.

(Item C20)

The recording medium according to any one of items C15 to C19, wherein the image data on at least part of the brain of the subject includes a combination of: running data on the motor fibers of the subject; data on a position of a brain sulcus of the patient; data on a distance between a brain surface and a cranial bone of the patient; data on a site referred to as the eloquent area in cerebral arteriovenous malformation (AVM) of the subject; data on a position of an artificial object, such as an artificial bone, an artificial dura mater or a titanium plate; data on a position of a thick artery directly below the skin; and data on a position of a thick blood vessel in the brain.

(Item C21)

The recording medium according to any one of items C15 to C20, further comprising one or more of features according to items 26 to 47.

(Item C22)

A system for identifying a route of administration of cells in cell therapy for a central nervous system disorder in a subject, the system comprising:
x) a learning section for inputting a group of image data on at least part of the brain of the subject and a group of data on a route of administration of cells into an artificial intelligence model as learning data and causing the artificial intelligence model to learn the learning data;
i) an acquiring section for acquiring, by an imaging device, image data on at least part of the brain of the subject;
y) an inputting section for inputting the image data on at least part of the brain of the subject acquired in the i) into the learned artificial intelligence model; and
z) a calculating section for causing the learned artificial intelligence model to calculate the data on the route of administration of cells.

(Item C23)

The system according to item C22, further comprising:
ii) an obtaining section for obtaining information on the brain of the subject by a computer device in communication with the imaging device;
iii) a providing section for providing a candidate for a route of administration of cells by the following procedure, the providing section comprising:
  aa) a selecting section for selecting, by the computer device, a safe region near a damage position as an administration site;
  bb) an identifying section for identifying an administration route to the selected administration site; and
  cc) a selecting section for optionally selecting, by the computer device, an excision position for passing an administration device for administering the cells in the scalp, and
iv) an outputting section for outputting the selected administration site as a graphic display.

(Item C24)

The system according to item C22 or C23, wherein the image data on at least part of the brain of the subject includes at least one of: running data on the motor fibers of the subject; data on a damage position in which the motor fibers are damaged; data on a position of the brain surface of the subject; data on an edema region of the subject; and data on a site referred to as the eloquent area in cerebral arteriovenous malformation (AVM) of the subject.

(Item C25)

The system according to any one of items C22 to C24, wherein the image data on at least part of the brain of the subject includes a combination of: running data on the motor fibers of the subject; data on a damage position in which the motor fibers are damaged; data on a position of the brain surface of the subject; data on an edema region of the subject; and data on a site referred to as the eloquent area in cerebral arteriovenous malformation (AVM) of the subject.

(Item C26)

The system according to any one of items C22 to C25, wherein the image data on at least part of the brain of the subject includes at least one of: running data on the motor fibers of the subject; data on a position of a brain sulcus of the patient; data on a distance between a brain surface and a cranial bone of the patient; data on a site referred to as the eloquent area in cerebral arteriovenous malformation (AVM) of the subject; data on a position of an artificial object, such as an artificial bone, an artificial dura mater or a titanium plate; data on a position of a thick artery directly below the skin; and data on a position of a thick blood vessel in the brain.

(Item C27)

The system according to any one of items C22 to C26, wherein the image data on at least part of the brain of the subject includes a combination of: running data on the motor fibers of the subject; data on a position of a brain sulcus of the patient; data on a distance between a brain surface and a cranial bone of the patient; data on a site referred to as the eloquent area in cerebral arteriovenous malformation (AVM) of the subject; data on a position of an artificial object, such as an artificial bone, an artificial dura mater or a titanium plate; data on a position of a thick artery directly below the skin; and data on a position of a thick blood vessel in the brain.

(Item C28)

The system according to any one of items C22 to C27, further comprising one or more of features according to items 26 to 47.

(Item D1)

A method for identifying a route of administration of cells in cell therapy for a central nervous system disorder in a subject, the method comprising:
- x) inputting a group of image data on at least part of the brain of the subject and a group of data on a route of administration of cells into an artificial intelligence model as learning data and causing the artificial intelligence model to learn the learning data;
- i) acquiring, by an imaging device, image data on at least part of the brain of the subject;
- y) inputting the image data on at least part of the brain of the subject acquired in the i) into the learned artificial intelligence model; and
- z) causing the learned artificial intelligence model to calculate the data on the route of administration of cells.

(Item D2)

The method according to item D1, further comprising:
- ii) obtaining information on the brain of the subject by a computer device in communication with the imaging device;
- iii) providing a candidate for a route of administration of cells by the following procedure, the providing step comprising:
  - a) optionally, selecting, by the computer device, an excision position for passing an administration device for administering the cells in the scalp;
  - b) selecting, by the computer device, an opening for allowing the administration device to pass through in the cranial bone for administering cell therapy;
  - c) identifying, by the computer device, at least one brain route exclusion region selected from the group consisting of motor fibers, cerebral blood vessels, sulci, and functional sites using the acquired image data and data on the brain of the subject;
  - d) selecting, by the computer device, a safe region near the damage position as an administration site; and
  - e) depicting an administration route between the opening and the administration site, wherein the administration route is depicted with information about the brain route exclusion region, and optionally providing suitability information about the administration route from the information about the brain route exclusion region, and
- iv) outputting the calculated administration site as a graphic display.

(Item D3)

The method according to item D1 or D2, wherein the image data on at least part of the brain of the subject includes at least one of: running data on the motor fibers of the subject; data on a damage position in which the motor fibers are damaged; data on a position of the brain surface of the subject; data on an edema region of the subject; and data on a site referred to as the eloquent area in cerebral arteriovenous malformation (AVM) of the subject.

(Item D4)

The method according to any one of items D1 to D3, wherein the image data on at least part of the brain of the subject includes a combination of: running data on the motor fibers of the subject; data on a damage position in which the motor fibers are damaged; data on a position of the brain surface of the subject; data on an edema region of the subject; and data on a site referred to as the eloquent area in cerebral arteriovenous malformation (AVM) of the subject.

(Item D5)

The method according to any one of items D1 to D4, wherein the image data on at least part of the brain of the subject includes at least one of: running data on the motor fibers of the subject; data on a position of a brain sulcus of the patient; data on a distance between a brain surface and a cranial bone of the patient; data on a site referred to as the eloquent area in cerebral arteriovenous malformation (AVM) of the subject; data on a position of an artificial object, such as an artificial bone, an artificial dura mater or a titanium plate; data on a position of a thick artery directly below the skin; and data on a position of a thick blood vessel in the brain.

(Item D6)

The method according to any one of items D1 to D5, wherein the image data on at least part of the brain of the subject includes a combination of: running data on the motor fibers of the subject; data on a position of a brain sulcus of the patient; data on a distance between a brain surface and a cranial bone of the patient; data on a site referred to as the eloquent area in cerebral arteriovenous malformation (AVM) of the subject; data on a position of an artificial object, such as an artificial bone, an artificial dura mater or a titanium plate; data on a position of a thick artery directly below the skin; and data on a position of a thick blood vessel in the brain.

(Item D7)

The method according to any one of items D1 to D6, further comprising one or more of features according to items 49 to 52.

(Item D8)

A program that causes a computer to execute a method for identifying a route of administration of cells in cell therapy for a central nervous system disorder in a subject, the method comprising:
- x) inputting a group of image data on at least part of the brain of the subject and a group of data on a route of administration of cells into an artificial intelligence model as learning data and causing the artificial intelligence model to learn the learning data;
- i) acquiring, by an imaging device, image data on at least part of the brain of the subject;
- y) inputting the image data on at least part of the brain of the subject acquired in the i) into the learned artificial intelligence model; and
- z) causing the learned artificial intelligence model to calculate the data on the route of administration of cells.

(Item D9)

The program according to item D8, wherein the method further comprises:
- ii) obtaining information on the brain of the subject by a computer device in communication with the imaging device;

iii) providing a candidate for a route of administration of cells by the following procedure, the providing step comprising:
  a) optionally, selecting, by the computer device, an excision position for passing an administration device for administering the cells in the scalp;
  b) selecting, by the computer device, an opening for allowing the administration device to pass through in the cranial bone for administering cell therapy;
  c) identifying, by the computer device, at least one brain route exclusion region selected from the group consisting of motor fibers, cerebral blood vessels, sulci, and functional sites using the acquired image data and data on the brain of the subject;
  d) selecting, by the computer device, a safe region near the damage position as an administration site; and
  e) depicting an administration route between the opening and the administration site, wherein the administration route is depicted with information about the brain route exclusion region, and optionally providing suitability information about the administration route from the information about the brain route exclusion region, and
iv) outputting the calculated administration site as a graphic display.

(Item D10)

The program according to item D8 or D9, wherein the image data on at least part of the brain of the subject includes at least one of: running data on the motor fibers of the subject; data on a damage position in which the motor fibers are damaged; data on a position of the brain surface of the subject; data on an edema region of the subject; and data on a site referred to as the eloquent area in cerebral arteriovenous malformation (AVM) of the subject.

(Item D11)

The program according to any one of items D8 to D10, wherein the image data on at least part of the brain of the subject includes a combination of: running data on the motor fibers of the subject; data on a damage position in which the motor fibers are damaged; data on a position of the brain surface of the subject; data on an edema region of the subject; and data on a site referred to as the eloquent area in cerebral arteriovenous malformation (AVM) of the subject.

(Item D12)

The program according to any one of items D8 to D11, wherein the image data on at least part of the brain of the subject includes at least one of: running data on the motor fibers of the subject; data on a position of a brain sulcus of the patient; data on a distance between a brain surface and a cranial bone of the patient; data on a site referred to as the eloquent area in cerebral arteriovenous malformation (AVM) of the subject; data on a position of an artificial object, such as an artificial bone, an artificial dura mater or a titanium plate; data on a position of a thick artery directly below the skin; and data on a position of a thick blood vessel in the brain.

(Item D13)

The program according to any one of items D8 to D12, wherein the image data on at least part of the brain of the subject includes a combination of: running data on the motor fibers of the subject; data on a position of a brain sulcus of the patient; data on a distance between a brain surface and a cranial bone of the patient; data on a site referred to as the eloquent area in cerebral arteriovenous malformation (AVM) of the subject; data on a position of an artificial object, such as an artificial bone, an artificial dura mater or a titanium plate; data on a position of a thick artery directly below the skin; and data on a position of a thick blood vessel in the brain.

(Item D14)

The program according to any one of items D8 to D13, further comprising one or more of features according to items 49 to 52.

(Item D15)

A recording medium having a program stored thereon that causes a computer to execute a method for identifying a route of administration of cells in cell therapy for a central nervous system disorder in a subject, the method comprising:
  x) inputting a group of image data on at least part of the brain of the subject and a group of data on a route of administration of cells into an artificial intelligence model as learning data and causing the artificial intelligence model to learn the learning data;
  i) acquiring, by an imaging device, image data on at least part of the brain of the subject;
  y) inputting the image data on at least part of the brain of the subject acquired in the i) into the learned artificial intelligence model; and
  z) causing the learned artificial intelligence model to calculate the data on the route of administration of cells.

(Item D16)

The recording medium according to item D15, wherein the method further comprises:
  ii) obtaining information on the brain of the subject by a computer device in communication with the imaging device;
  iii) providing a candidate for a route of administration of cells by the following procedure, the providing step comprising:
    a) optionally, selecting, by the computer device, an excision position for passing an administration device for administering the cells in the scalp;
    b) selecting, by the computer device, an opening for allowing the administration device to pass through in the cranial bone for administering cell therapy;
    c) identifying, by the computer device, at least one brain route exclusion region selected from the group consisting of motor fibers, cerebral blood vessels, sulci, and functional sites using the acquired image data and data on the brain of the subject;
    d) selecting, by the computer device, a safe region near the damage position as an administration site; and
    e) depicting an administration route between the opening and the administration site, wherein the administration route is depicted with information about the brain route exclusion region, and optionally providing suitability information about the administration route from the information about the brain route exclusion region, and
  iv) outputting the calculated administration site as a graphic display.

(Item D17)

The recording medium according to item D15 or D16, wherein the image data on at least part of the brain of the subject includes at least one of: running data on the motor fibers of the subject; data on a damage position in which the motor fibers are damaged; data on a position of the brain surface of the subject; data on an edema region of the subject; and data on a site referred to as the eloquent area in cerebral arteriovenous malformation (AVM) of the subject.

(Item D18)

The recording medium according to any one of items D15 to D17, wherein the image data on at least part of the brain of the subject includes a combination of: running data on the motor fibers of the subject; data on a damage position in which the motor fibers are damaged; data on a position of the brain surface of the subject; data on an edema region of the subject; and data on a site referred to as the eloquent area in cerebral arteriovenous malformation (AVM) of the subject.

(Item D19)

The recording medium according to any one of items D15 to D18, wherein the image data on at least part of the brain of the subject includes at least one of: running data on the motor fibers of the subject; data on a position of a brain sulcus of the patient; data on a distance between a brain surface and a cranial bone of the patient; data on a site referred to as the eloquent area in cerebral arteriovenous malformation (AVM) of the subject; data on a position of an artificial object, such as an artificial bone, an artificial dura mater or a titanium plate; data on a position of a thick artery directly below the skin; and data on a position of a thick blood vessel in the brain.

(Item D20)

The recording medium according to any one of items D15 to D19, wherein the image data on at least part of the brain of the subject includes a combination of: running data on the motor fibers of the subject; data on a position of a brain sulcus of the patient; data on a distance between a brain surface and a cranial bone of the patient; data on a site referred to as the eloquent area in cerebral arteriovenous malformation (AVM) of the subject; data on a position of an artificial object, such as an artificial bone, an artificial dura mater or a titanium plate; data on a position of a thick artery directly below the skin; and data on a position of a thick blood vessel in the brain.

(Item D21)

The recording medium according to any one of items D15 to D20, further comprising one or more of features according to items 49 to 52.

(Item D22)

A system for identifying a route of administration of cells in cell therapy for a central nervous system disorder in a subject, the system comprising:
- x) a learning section for inputting a group of image data on at least part of the brain of the subject and a group of data on a route of administration of cells into an artificial intelligence model as learning data and causing the artificial intelligence model to learn the learning data;
- i) an acquiring section for acquiring, by an imaging device, image data on at least part of the brain of the subject;
- y) an inputting section for inputting the image data on at least part of the brain of the subject acquired in the i) into the learned artificial intelligence model; and
- z) a calculating section for causing the learned artificial intelligence model to calculate the data on the route of administration of cells.

(Item D23)

The system according to item D22, further comprising:
- ii) an obtaining section for obtaining information on the brain of the subject by a computer device in communication with the imaging device;
- iii) a providing section for providing a candidate for a route of administration of cells by the following procedure, the providing section comprising:
  - a) an excision position selecting section for optionally selecting, by the computer device, an excision position for passing an administration device for administering the cells in the scalp;
  - b) an opening selecting section for selecting, by the computer device, an opening for allowing the administration device to pass through in the cranial bone for administering cell therapy;
  - c) an identifying section for identifying, by the computer device, at least one brain route exclusion region selected from the group consisting of motor fibers, cerebral blood vessels, sulci, and functional sites using the acquired image data and data on the brain of the subject;
  - d) a selecting section for selecting, by the computer device, a safe region near the damage position as an administration site; and
  - e) an information providing section for depicting an administration route between the opening and the administration site, wherein the administration route is depicted with information about the brain route exclusion region, and optionally providing suitability information about the administration route from the information about the brain route exclusion region, and
- iv) an outputting section for outputting the calculated administration site as a graphic display.

(Item D24)

The system according to item D22 or D23, wherein the image data on at least part of the brain of the subject includes at least one of: running data on the motor fibers of the subject; data on a damage position in which the motor fibers are damaged; data on a position of the brain surface of the subject; data on an edema region of the subject; and data on a site referred to as the eloquent area in cerebral arteriovenous malformation (AVM) of the subject.

(Item D25)

The system according to any one of items D22 to D24, wherein the image data on at least part of the brain of the subject includes a combination of: running data on the motor fibers of the subject; data on a damage position in which the motor fibers are damaged; data on a position of the brain surface of the subject; data on an edema region of the subject; and data on a site referred to as the eloquent area in cerebral arteriovenous malformation (AVM) of the subject.

(Item D26)

The system according to any one of items D22 to D25, wherein the image data on at least part of the brain of the subject includes at least one of: running data on the motor fibers of the subject; data on a position of a brain sulcus of the patient; data on a distance between a brain surface and a cranial bone of the patient; data on a site referred to as the eloquent area in cerebral arteriovenous malformation (AVM) of the subject; data on a position of an artificial object, such as an artificial bone, an artificial dura mater or a titanium plate; data on a position of a thick artery directly below the skin; and data on a position of a thick blood vessel in the brain.

(Item D27)

The system according to any one of items D22 to D26, wherein the image data on at least part of the brain of the subject includes a combination of: running data on the motor fibers of the subject; data on a position of a brain sulcus of the patient; data on a distance between a brain surface and a cranial bone of the patient; data on a site referred to as the eloquent area in cerebral arteriovenous malformation (AVM) of the subject; data on a position of an artificial object, such as an artificial bone, an artificial dura mater or a titanium plate; data on a position of a thick artery directly below the skin; and data on a position of a thick blood vessel in the brain.

(Item D28)

The system according to any one of items D22 to D27, further comprising one or more of features according to items 49 to 52.

In the present invention, it is intended that the above one or more features may be provided in further combinations, in addition to the explicit combinations. Still further embodiments and advantages of the present invention will be appreciated by those skilled in the art upon reading and understanding the following detailed description as necessary.

Advantageous Effects of Invention

Examples of the effects achieved by each of the inventions will be described hereinafter.

(1) Determination on the Administration Site

The provision of an objective method, as in the present disclosure, allows performing of accurate administration and allows significant increasing of the success rate of cell therapy for the brain. Furthermore, the computer-programming of the method provides a practitioner with a choice of successful administration sites, which allows the practitioner to perform surgery with a certain degree of objectivity, rather than surgery where the practitioner relies on experience and intuition, thereby contributing to increased reproducibility and success rate.

(2) Determination on the Passing Route for the Administration Needle

The provision of an objective method, as in the present disclosure, allows performing of accurate administration and allows significant increasing of the success rate of cell therapy for the brain. Furthermore, the computer-programming of the method provides a practitioner with a choice of successful administration routes, which allows the practitioner to perform surgery with a certain degree of objectivity, rather than surgery where the practitioner relies on experience and intuition, thereby contributing to increased reproducibility and success rate.

(3) Method of Preventing Cerebrospinal Fluid Leakage

The provision of an objective method against cerebrospinal fluid leakage, as in the present disclosure, allows performing of cell therapy with a significantly reduced probability of failure and also allows significant increasing of the success rate of cell therapy for the brain. Furthermore, the computer-programming of the method provides a practitioner with a choice of successful approaches against cerebrospinal fluid leakage, which allows the practitioner to perform surgery with a certain degree of objectivity, rather than surgery where the practitioner relies on experience and intuition, thereby contributing to increased reproducibility and success rate.

BRIEF DESCRIPTION OF DRAWINGS

FIG. 1A FIG. 1 shows an MRI image of a patient whose cell administration position has been determined according to the present disclosure. A: DWI image.

FIG. 1B FIG. 1 shows an MRI image of a patient whose cell administration position has been determined according to the present disclosure. B: DTI image.

FIG. 1C FIG. 1 shows an MRI image of a patient whose cell administration position has been determined according to the present disclosure. C: FLAIR image. In Figure C, the cell administration position is circled.

FIG. 2A FIG. 2 shows an MRI image of a patient whose cell administration position has been determined according to the present disclosure. A: DWI image.

FIG. 2B FIG. 2 shows an MRI image of a patient whose cell administration position has been determined according to the present disclosure. B: DTI image.

FIG. 2C FIG. 2 shows an MRI image of a patient whose cell administration position has been determined according to the present disclosure. C: FLAIR image. In Figure C, the cell administration position is circled.

FIG. 3A FIG. 3 shows an MRI image of a patient whose cell administration position has been determined according to the present disclosure. A: DWI IMAGE.

FIG. 3B FIG. 3 shows an MRI image of a patient whose cell administration position has been determined according to the present disclosure. B: DTI image.

FIG. 3C FIG. 3 shows an MRI image of a patient whose cell administration position has been determined according to the present disclosure. C: FLAIR image. In Figure C, the cell administration position is circled.

FIG. 4A FIG. 4 shows an MRI image of a patient whose cell administration position has been determined according to the present disclosure. A: DWI image.

FIG. 4B FIG. 4 shows an MRI image of a patient whose cell administration position has been determined according to the present disclosure. B: DTI image.

FIG. 4C FIG. 4 shows an MRI image of a patient whose cell administration position has been determined according to the present disclosure. C: FLAIR image. In Figure C, the cell administration position is circled.

FIG. 5A FIG. 5 shows an MRI image of a patient whose cell administration position has been determined according to the present disclosure. A: DWI image.

FIG. 5B FIG. 5 shows an MRI image of a patient whose cell administration position has been determined according to the present disclosure. B: DTI image.

FIG. 5C FIG. 5 shows an MRI image of a patient whose cell administration position has been determined according to the present disclosure. C: FLAIR image. In Figure C, the cell administration position is circled.

FIG. 6A FIG. 6 shows an MRI image of a patient whose cell administration position has been determined according to the present disclosure. A: DWI image.

FIG. 6B FIG. 6 shows an MRI image of a patient whose cell administration position has been determined according to the present disclosure. B: DTI image.

FIG. 6C FIG. 6 shows an MRI image of a patient whose cell administration position has been determined according to the present disclosure. C: FLAIR image. In Figure C, the cell administration position is circled.

FIG. 7A FIG. 7 shows an MRI image of a patient whose cell administration position has been determined according to the present disclosure. A: DWI image.

FIG. 7B FIG. 7 shows an MRI image of a patient whose cell administration position has been determined according to the present disclosure. B: DTI image.

FIG. 7C FIG. 7 shows an MRI image of a patient whose cell administration position has been determined according to the present disclosure. C: FLAIR image. In Figure C, the cell administration position is circled.

DESCRIPTION OF EMBODIMENTS

Hereinafter, specific embodiments of the present disclosure will be described in detail, but the present disclosure is not limited to the following embodiments, and the present disclosure can be carried out with appropriate modifications within the intended scope of the present disclosure. In addition, although the description may be omitted as appropriate for the portions where the descriptions are duplicated, the gist of the invention is not limited.

Throughout the entire specification, a singular expression should be understood as encompassing the concept thereof in the plural form, unless specifically noted otherwise. Thus, singular articles (e.g., "a", "an", "the", and the like in the case of English) should also be understood as encompassing the concept thereof in the plural form, unless specifically noted otherwise. Further, the terms used herein should be understood as being used in the meaning that is commonly used in the art, unless specifically noted otherwise. Therefore, unless defined otherwise, all terminologies and scientific technical terms that are used herein have the same meaning as the general understanding of those skilled in the art to which the present invention pertains. In case of a contradiction, the present specification (including the definitions) takes precedence.

Definitions

As used herein, the term "subject" or "object" or "test object" (subject in English) is used synonymously with the term, a patient, and such a term refers to any living body or animal covered by the techniques of the present disclosure, such as cell therapy, and is sometimes referred to as an object. Note that they all have the same meaning. The subject is preferably human, but is not limited to such.

As used herein, the term "central nervous system disorder" refers to any disorder of the central nervous system.

As used herein, the term "cell therapy" (also referred to as "cellular therapy" or "cytotherapy" in English) refers to the transplantation of human or animal cells to prevent, treat, or ameliorate one or more symptoms associated with diseases or disorders that include, but are not limited to, replacement or repair of damaged tissue or organ, regulation of immune response, reduction of inflammatory symptoms and cancer, etc.

As used herein, the term "imaging device" refers to any device for capturing tomographic images of the body. The imaging devices include magnetic resonance imaging (MRI) devices, computed tomography (CT) devices, angiography examination devices, ultrasonography devices, etc., but preferably, MRI (devices). Images can be presented or displayed by photoacoustic imaging technology, which is also referred to as graphic display. The images can be displayed particularly on computer monitors, plasma screens, LCD screens, CRTs, projection screens, fog screens, water screens, VR goggles, helmets or glasses with an image display screen worn on the head, or any other structures capable of displaying an image, so that the subject can see the images.

As used herein, the term "motor fiber" refers to a nerve fiber that transmits a signal to direct the movement of the muscles of a subject's body or internal organs. Motor fibers pass through the precentral gyrus, the crus posterius capsulae internae, and the bridges. The term is used interchangeably with "motor nerves".

As used herein, the term "running data on the motor fiber" refers to a method of estimating the running mode of nerve fiber bundles such as white matter from imaging data such as MRI images, and data depicting the running of nerve fibers estimated by the method. As used herein, it may be used interchangeably with tractography.

As used herein, the term "electrosurgical device" refers to any device capable of cauterizing, coagulating, and/or cutting tissue, which is attached to a suitable electrosurgical energy source and which has active electrodes. The active electrode is any form of conductive element, which may be in the form of a thin flat blade with an elongated and pointed or rounded distal end. Any electrosurgical devices capable of coagulating and adhering the arachnoid and mucous membranes may be used, and the electrosurgical devices include, but are not limited to, electrosurgical instruments such as bipolar coagulation tweezers.

As used herein, the term "brain shift" refers to the movement of the brain caused by cerebrospinal fluid leakage during trepanning and air invasion. The brain shift interferes with the identification of target locations in stereotactic brain surgery.

As used herein, the term "eloquent area" refers to an area responsible for important brain functions such as motor function, sensory function, language function, and vision.

As used herein, the term "brain surface" refers to the surface of the cerebrum. It refers to the arachnoid membrane or pia mater that covers the brain surface of a specific site, in the case of, for example, the arachnoid membrane of the brain surface, or the pia mater of the brain surface, of the specific site.

As used herein, the term "cerebrospinal fluid" refers to a clear, colorless fluid that fills the ventricular system and the subarachnoid space. The cerebrospinal fluid resides in the region between the arachnoid membrane and pia mater. It is a waste fluid produced from the choroid plexus of the ventricular system, and has a role in buffering the water content of the brain and maintaining the shape and position of the brain. The subject term is used interchangeably with "cerebrospinal fluid".

As used herein, the term "sulcus" refers to a groove on the surface of the brain, which is a region filled with cerebrospinal fluid.

As used herein, the term "gyrus" refers to a raised portion that is present in the cerebral cortex and that is a region surrounded by sulci.

As used herein, the term "apex of the gyrus" refers to a site of the gyrus that is closest to the cranial bone and its surrounding regions, and does not include the region around the sulcus.

As used herein, the term "National Institute of Health Stroke Scale (NIHSS)" refers to the stroke severity rating scale. It includes items for evaluation of consciousness, evaluation of gaze, evaluation of visual field, evaluation of facial palsy, evaluation of quadriplegia, evaluation of ataxia, evaluation of sensory impairment, aphasia, dysarthria, extinction phenomenon, and neglect. For each item, the severity increases as the score increases, and the maximum score is set to be 42.

As used herein, the term "modified Rankin Scale (mRS)" is an evaluation standard frequently used as a general prognosis evaluation scale for stroke. The evaluation can be conducted on a 7-point scale from 0 to 6. The severity increases as the score increases.

As used herein, the term "Functional Independence Measure (FIM)" is an index that quantifies and evaluates the degree of independence of activities of daily living. This is also referred to as a functional independence measure. Since this includes cognitive items, such as communication and social cognition, in addition to motor items, it is possible to evaluate actual activities of daily living. There are thirteen motor items and five cognitive items. Each item is evaluated on a 7-point scale, and as the score increases, it indicates being more independent.

As used herein, the "Barthel Index (BI)" refers to one of the evaluation scales in the rehabilitation of cerebrovascular accidents. This includes ten evaluation items: feeding, mobility on level surfaces, grooming, toilet use, bathing, transfers (wheelchair), stairs, dressing, bowel control, and bladder control, where as the score increases, it indicates being more independent.

As used herein, the term "Fugl-Meyer Assessment (FMA)" refers to a comprehensive method for assessing physical function of stroke, which evaluates items of upper limb motor function, lower limb motor function, balance, sensation, range of motion and pain. As the score increases, it indicates higher physical function. (MRI images)

As used herein, the MRI (magnetic resonance imaging) is also referred to as nuclear magnetic resonance imaging (NMRI). Two-thirds of the human body is composed of water, and hydrogen (H) is also contained in the structural formulas of various fatty acids and amino acids; thus, in medical MRI, the image is visualized by the signal of this hydrogen atom (1H). Hydrogen is composed of one proton (proton) and one electron, and the electron rotates (spins) around the proton. Due to this spin, each hydrogen atom is slightly magnetized. Normally, magnetization is not seen as a whole due to the disparate directions of this spin. When a strong magnetic field is applied from the outside, the spin directions of individual hydrogen atoms are forcibly corrected in the same direction. When a radio wave of a specific frequency (e.g. 42.58 MHz) is applied to this state, the hydrogen nuclei resonate with the radio wave and emit the radio wave by themselves. This phenomenon is referred to as nuclear magnetic resonance, and a map showing the signal intensity distribution, with the addition of positional information to this phenomenon, becomes a nuclear magnetic resonance image, that is, MRI. By pulsating radio waves of this specific frequency and changing the conditions, different types of images are visualized (T1-weighted image, T2-weighted image, etc.).

As used herein, T1WI is used as an abbreviation for T1 weighted image (T1WI). In T1WI, water is visualized in black and with low signal intensity signals (the ventricles are black), presenting an image similar to CT, and is characterized by easy capture of anatomical structures such as the cerebral cortex and white matter.

Substances that are high signal intensity in T1 weighted images include: fat; subacute hematoma (methemoglobin); brain white matter (compared to gray matter) (since myelination has not progressed in infants, the contrast between white matter and gray matter is opposite); water with a lot of dissolved protein; cortical necrosis area, which may be high signal intensity; significant calcified nest, which may be high signal intensity; normal posterior pituitary and anterior pituitary of newborns and pregnant women (late pregnancy); manganese deposition site, where globus pallidus may be high signal intensity, especially with liver dysfunction; contrast-enhanced area with Gd (gadolinium), the site of failure/defect of the blood-brain barrier is imaged with regard to the central nervous system, and the contrast effect does not necessarily reflect the vascularity. Paramagnetic substance: the above-mentioned methemoglobin, manganese, and gadolinium are also paramagnetic substances. Other paramagnetic substances may include melanin (melanoma can be high signal intensity in T1-weighted images without bleeding). Substances that are low signal intensity in T1-weighted images may include water (cerebrospinal fluid), brain gray matter (compared to white matter), many lesions (reflecting increased water content, such as infarctions and tumors), hyperacute/acute hematoma (before methemoglobin production), and other substances that do not include those that generate signals, such as bone cortex, calcification, and air.

As used herein, T2WI is an abbreviation for T2 weighted image (T2WI). In T2WI, water is visualized in white with high signal intensity signals (the ventricles are white), and many lesions are visualized with high signal intensity signals, which is useful for extracting lesions.

Substances that are high signal intensity in T2-weighted images include water (cerebrospinal fluid), many lesions (reflecting increased water content, such as tumor, infarction, edema, and demyelination), brain gray matter (compared to white matter) (the contrast between white matter and gray matter is opposite in infants), subacute hematoma (after red blood cell destruction), and hyperacute hematoma (before oxyhemoglobin is converted to deoxyhemoglobin). Substances that are low signal intensity in T2-weighted images include acute hematoma (before red blood cells are destroyed, containing deoxyhemoglobin or methemoglobin inside), obsolete bleeding foci (hemosiderin), areas high in iron (ferritin) (especially, globus pallidus, midbrain red nucleus, substantia nigra, cerebellar dentate nucleus), brain white matter (compared to gray matter), substances that do not include those that generate signals such as bone cortex, dense calcification and air, water with a large amount of dissolved protein, tissues with less water, such as fibrosis and dense tissues, and paramagnetic material with non-uniform distribution (such as deposition sites of the above acute hematoma, obsolete bleeding and iron, and melanin).

As used herein, FLAIR is an abbreviation for "FLAIR image: Fluid Attenuated Inversion Recovery (water suppression image)". The FLAIR image is basically a T2-weighted image (a T2WI-like image in which the ventricles look black) in which the water signal is suppressed, where the lesion adjacent to the ventricles is clearly visualized. This is useful for confirming the site of chronic cerebral infarction (visualized in white) such as binswanger-type leukoencephalopathy seen in hidden cerebral infarction and vascular dementia represented by lacunar infarction. Simply put, it is a T2-weighted image (there is also a T1-weighted element) captured by devising conditions so that the cerebrospinal fluid becomes black. It is often imaged to reduce oversight of lesions close to cerebrospinal fluid, such as around the ventricles and near the cortex. A small amount of subarachnoid hemorrhage that cannot be detected by CT may be visualized. In acute cerebral infarction, occluded blood vessels may be perceived as high signal intensity. The pulsation of cerebrospinal fluid and the artifacts caused by magnetic substances are strong, and the detection rate of posterior fossa lesions is said to be slightly inferior, but there is no problem in practical use.

As used herein, T2*WI is a T2*weighted image (T2 star weighted image) or T2 star weighted image (T2*WT). T2*weighted images have extremely high power to detect hemorrhagic lesions (visualized in black), and are excellent in confirming previously developed hemorrhagic lesions and detecting asymptomatic microbleeding.

As used herein, DWI is an abbreviation for Diffusion weighted image, which is an image of the diffusion motion (free motion degree) of water molecules. The region where the diffusion decreases is visualized as high signal intensity signals. This is useful for making a decision on the site of cerebral infarction in the hyperacute phase (visualized in white) because the diffusion decreases in cerebral infarction in the acute phase.

As used herein, the term "prognosis" means predicting the likelihood of death or progression due to a disease or disorder such as cancer. Prognostic factors are variables related to the natural course of the disease or disorder, and these affect the recurrence rate of patients who have once developed the disease or disorder. Clinical indicators associated with worse prognosis include, for example, any cellular indicator used in the present disclosure. Prognostic factors are often used to classify patients into subgroups with different pathologies. By associating the genetic information with diagnostically useful trait information using the techniques disclosed herein, it may be possible to provide prognostic factors based on the control's genetic information.

As used herein, the term "program" is used in the usual sense as used in the art, is an orderly description of the processing that a computer should perform, and is treated as a "product" under the Patent Law in Japan. All computers operate according to the program. In modern computers, the program is expressed as data in a broad sense and stored in a recording medium or a storage device.

As used herein, the term "recording medium" is a recording medium having stored thereon a program for executing the method of the present disclosure, and the recording medium may be any recording medium that can record programs. The recording medium may be, for example, a ROM or an HDD, which can be stored internally, a magnetic disk, a flash memory, such as a USB memory, or other external storage devices, but the recording medium is not limited thereto.

As used herein, the term "system" means a configuration for executing the method or program of the present disclosure. The system originally means a system or organization for accomplishing a purpose, in which a plurality of elements are systematically composed and influence each other. In the field of computers, it refers to the entire configuration of hardware, software, OS, network, etc.

As used herein, the term "machine learning" refers to a technology for imparting a computer the ability to learn without explicit programming. This is a process of improving a function unit's own performance by acquiring new knowledge/skill or reconfiguring existing knowledge/skill. Most of the effort required for programming details can be reduced by programming a computer to learn from experience. In the machine learning field, a method of constructing a computer program that enables automatic improvement from experience has been discussed. Data analysis/machine learning plays a role in elemental technology that is the foundation of intelligent processing along with field of the algorithms. Generally, data analysis/machine learning is utilized in conjunction with other technologies, thus requiring the knowledge in the cooperating field (domain specific knowledge; e.g., medical field). The range of application thereof includes roles such as prediction (collect data and predict what would happen in the future), search (find a notable feature from the collected data), and testing/depicting (find relationship of various elements in the data). Machine learning is based on an indicator indicating the degree of achievement of a goal in the real world. The user of machine learning must understand the goal in the real world. An indicator that improves when an objective is achieved needs to be formularized. Machine learning has the opposite problem that is an ill-posed problem for which it is unclear whether a solution is found. The behavior of the learned rule is not definitive, but is stochastic (probabilistic). Machine learning requires an innovative operation with the premise that some type of uncontrollable element would remain. The tailor-made method of the invention can be considered as a solution to such a problem. It is useful for a user of machine learning to sequentially select data or information in accordance with the real world goal while observing performance indicators during training and operation.

Linear regression, logistic regression, support vector machine, or the like can be used for machine learning, and cross validation (CV) can be performed to calculate differentiation accuracy of each model. After ranking, a feature can be increased one at a time for machine learning (linear regression, logistic regression, support vector machine, or the like) and cross validation to calculate differentiation accuracy of each model. A model with the highest accuracy can be selected thereby. Any machine learning can be used herein. Linear, logistic, support vector machine (SVM), or the like can be used as supervised machine learning.

Machine learning uses logical reasoning. There are roughly three types of logical reasoning, i.e., deduction, induction, and abduction as well as analogy. Deduction, under the hypothesis that Socrates is a human and all humans die, reaches a conclusion that Socrates would die, which is a special conclusion. Induction, under the hypothesis that Socrates would die and Socrates is a human, reaches a conclusion that all humans would die, and determines a general rule. Abduction, under a hypothesis that Socrates would die and all humans die, arrives at Socrates is a human, which falls under a hypothesis/explanation. However, it should be noted that how induction generalizes is dependent on the premise, so that this may not be objective. Analogy is a probabilistic logical reasoning method which reasons that if object A has 4 features and object B has three of the same features, object B also has the remaining one feature so that object A and object B are the same or similar and close.

Impossibility has three basic principles, i.e., impossible, very difficult, and unsolved. Further, impossible includes generalization error, no free lunch theorem, and ugly duckling theorem and true model observation is impossible, so that this is impossible to verify. Such an ill-posed problem should be noted.

Feature/attribute in machine learning represents the state of an object being predicted when viewed from a certain aspect. A feature vector/attribute vector combines features (attributes) depicting an object being predicted in a vector form.

As used herein, the term "model" and "hypothesis" are used synonymously, which is expressed using mapping depicting the relationship of inputted prediction targets to prediction results, or a mathematical function or Boolean expression of a candidate set thereof. For learning with machine learning, a model considered the best approximation of the true model is selected from a model set by referring to training data.

Examples of models include generation model, identification model, function model, and the like. Models show a difference in the direction of classification model expression of the mapping relationship between the input (object being predicted) x and output (result of prediction) y. A generation model expresses a conditional distribution of output y given input x. An identification model expresses a joint distribution of input x and output y. The mapping relationship is probabilistic for an identification model and a generation model. A function model has a definitive mapping relationship, expressing a definitive functional relationship between input x and output y. While identification is sometimes considered slightly more accurate in an identification model and a generation model, there is basically no difference in view of the no free lunch theorem.

Model complexity: the degree of whether mapping relationship of an object being predicted and prediction result can be described in more detail and complexity. Generally, more training data is required for a model set that is more complex.

If a mapping relationship is expressed as a polynomial equation, a higher order polynomial equation can express a more complex mapping relationship. A higher order polynomial equation is considered a more complex model than a linear equation.

If a mapping relationship is expressed by a decision tree, a deeper decision tree with more nodes can express a more complex mapping relationship. Therefore, a decision tree with more nodes can be considered a more complex model than a decision tree with less nodes.

Classification thereof is also possible by the principle of expressing the corresponding relationship between inputs and outputs. For a parametric model, the distribution or shape of the function is completely determined by parameters. For a nonparametric model, the shape thereof is basically determined from data. Parameters only determine smoothness.

Parameter: an input for designating one of a set of functions or distribution of a model. It is also denoted as $Pr[y|x; \theta]$, $y=f(x; \theta)$, or the like to distinguish from other inputs.

For a parametric model, the shape of a Gaussian distribution is determined by mean/variance parameters, regardless of the number of training data. For a nonparametric model, only the smoothness is determined by the number of bin parameter in a histogram. This is considered more complex than a parametric model.

For learning in machine learning, a model considered the best approximation of the true model is selected from a model set by referring to training data. There are various learning methods depending on the "approximation" performed. A typical method is the maximum likelihood estimation, which is a standard of learning that selects a model with the highest probability of producing training data from a probabilistic model set. Maximum likelihood estimation can select a model that best approximates the true model. KL divergence to the true distribution becomes small for greater likelihood. There are various types of estimation that vary by the type of form for finding a parameter or estimated prediction value. Point estimation finds only one value with the highest certainty. Maximum likelihood estimation, MAP estimation, and the like use the mode of a distribution or function and are most often used. Meanwhile, interval estimation is often used in the field of statistics in a form of finding a range within which an estimated value falls, where the probability of an estimated value falling within the range is 95%. Distribution estimation is used in Bayesian estimation or the like in combination with a generation model introduced with a prior distribution for finding a distribution within which an estimated value falls.

Preferable Embodiments

The preferred embodiments of the present disclosure will be described hereinafter. It is understood that the embodiments provided herein, including the ones hereinafter, are provided to facilitate better understanding of the present disclosure, so that the scope of the present disclosure should not be limited by the following descriptions. Thus, it is apparent that those skilled in the art can refer to the descriptions herein to make appropriate modifications within the scope of the present disclosure. It is also understood that the following embodiments of the present disclosure can be used individually or as a combination.

(Cell Administration Method for Cell Therapy of the Brain)

The present disclosure provides, in one aspect, a method for identifying a site of administration of cells in cell therapy for a central nervous system disorder in a subject.

This method includes at least one of the following steps or procedures:

i) acquiring, by an imaging device, image data on at least part of the brain of the subject;

ii) obtaining information on the brain of the subject by a computer device in communication with the imaging device;

iii) providing a candidate for a route of administration of cells by the following procedure, the providing step including:

a) identifying, by the computer device, an excision position for passing an administration device for administering the cells in the scalp;

b) identifying, by the computer device, an opening for allowing the administration device to pass through in the cranial bone for administering cell therapy;

c) identifying, by the computer device, at least one brain route exclusion region selected from the group consisting of motor fibers, cerebral blood vessels, sulci, and functional sites using the acquired image data and data on the brain of the subject;

d) selecting, by the computer device, a safe region near the damage position as an administration site; and e) depicting an administration route between the opening and the administration site, wherein the administration route is depicted with information about the brain route exclusion region, and optionally providing suitability information about the administration route from the information about the brain route exclusion region, and iv) outputting the selected administration site as a graphic display.

In another aspect, the present disclosure provides a method for identifying a route of administration of cells in cell therapy for a central nervous system disorder in a subject, the method including:

i) acquiring, by an imaging device, image data on at least part of the brain of the subject;

ii) obtaining information on the brain of the subject by a computer device in communication with the imaging device;

iii) providing a candidate for a route of administration of cells by the following procedure, the providing step including:

aa) selecting, by the computer device, a safe region near a damage position as an administration site;

bb) identifying an administration route to the selected administration site; and cc) optionally, selecting, by the computer device, an excision position for passing an administration device for administering the cells in the scalp, and iv) outputting the selected administration site as a graphic display.

In one embodiment, i) acquiring, by an imaging device, image data on at least part of the brain of the subject may obtain at least part of image data on the brain of the subject using normal contrast procedures such as MRI or CT. Preferably, the image data on the brain to be acquired substantially covers the region to be targeted for cell therapy, and more preferably, it is advantageous that an image of the entire brain is obtained.

The image data includes DICOM, JPEG and TIFF, but DICOM is preferable.

In one embodiment, ii) obtaining information on the brain of the subject by a computer device in communication with the imaging device can be achieved using any brain information acquisition route performed in the art. Examples of useful information on the brain include past medical history of the brain, information on damage, information on motor fibers, and functional information (language field/higher brain functional area), etc.

In one embodiment, iii) providing a candidate for a route of administration of cells by the following procedure includes, for example, a) identifying, by the computer device, an excision position for passing an administration device for administering the cells in the scalp; b) identifying, by the computer device, an opening for allowing the administration device to pass through in the cranial bone for administering cell therapy; c) identifying, by the computer device, at least one brain route exclusion region selected from the group consisting of motor fibers, cerebral blood vessels, sulci, and functional sites using the acquired image data and data on the brain of the subject; d) selecting, by the computer device, a safe region near the damage position as an administration site; and e) depicting an administration route between the opening and the administration site, wherein the administration route is depicted with information about the brain route exclusion region, and optionally providing suitability information about the administration route from the information about the brain route exclusion region. As to the safe region, since the locations of the parts that have an important role for neural function have already been identified in humans with almost no individual difference, it is possible to incorporate these parts into the computer in advance. While left-handed people are almost the same as right-handed people, there are, very rarely, people who are left-handed and have functions on the opposite side (mainly in the area of language, both right-handed and left-handed people usually have a language field in the left hemisphere, so some ingenuity is required in that case; however, this modification is possible by a method known in the art; on rare occasions, there are left-handed people whose language field is in the right hemisphere). Even so, the language field can be confirmed by another method (MRI) in advance. Although care must be taken when the language field is in the right hemisphere and the administration route and administration site are set so as to pass through it, this is designable.

As used herein, for a) identifying, by the computer device, an excision position for passing an administration device for administering the cells in the scalp, techniques commonly used in the field of neurosurgery can be used. For example, if there is a scar that has been resected from the skin, resection that intersects the scar at an angle should be avoided. For example, an MRI image can be imported into Medtronic's navigation calculation system FlameLink, which allows confirming a skin depression. If the skin has already been incised, the incision is basically used. If the target Burr hole deviates significantly from the previous skin incision line, it should be coped by making a long incision in the skin and removing the galea.

As used herein, for b) identifying, by the computer device, an opening for allowing the administration device to pass through in the cranial bone for administering cell therapy, techniques commonly used in the field of neurosurgery can be used. For example, if possible, areas with an artificial object, such as an artificial bone, an artificial dura mater or a titanium plate are excluded from the administration route in order to prevent postoperative infection. The burr hole should be selected so that the insertion point does not overlap the functional site. Where the brain is atrophied and has sunk considerably (about 5 mm), even if the dura mater is incised, the distance to the brain is far, which can be a cause of an accident. Thus, the site where the brain surface is directly below the bone (the apex of the gyrus) is selected as the administration route. Where the burr hole is located near the midline, there may be a thick vein that perfuses the superior sagittal sinus (SSS) (in some cases, it may have become a venous lake). Thus, FlameLink is used to confirm that there are no thick veins around the dural incision site in advance.

As used herein, for c) identifying, by the computer device, at least one brain route exclusion region selected from the group consisting of motor fibers, cerebral blood vessels, sulci, and functional sites using the acquired image data and data on the brain of the subject, it can be identified by any approach used in the art. This can determine the administration site using at least one, preferably two, three, or four of the DWI image, T2 image, FLAIR image and DTI image. The region damaged by cerebral infarction is determined from the DWI image. It is recommended, preferably, not to administer cells to the region damaged by cerebral infarction because there is no blood flow therethrough and the administered cells will die. Next, using T2 images and FLAIR images, sites that are DWI-negative (that have avoided cell death) but have strong edema (recoverable but not necessarily desirable for administration) are evaluated, and motor fibers are visualized from DTI images to evaluate where the motor fibers are ruptured, which allows selecting of a candidate or range of the administration route. Next, an area that is close to the area where the tractography is ruptured or weakened (usually the white area on the DWI) and that is highly safe (an area where there is little damage even if bleeding or allergic reaction occurs: sites other than the site generally referred to as the eloquent area in AVM) can be selected as the cell administration site. At the time of selection, it may be useful to be careful to avoid the high signal intensity areas of the T2/FLAIR image and administer cells to the substantially normal side thereof. Tractography may not be visualized because the injury damage is too considerable. In such a case, however, the running of nerve fibers can be estimated with reference to contralateral tractography, and an estimated tractography can be created, to determine the cell administration site. To prevent cells from coming out of the administration site, it is recommended to exclude positions close to the brain surface (within 1 cm, 1.5 cm, 2 cm, 2.5 cm or 3 cm from the brain surface) from the candidate positions for administration. While the sites are visualized white in the DTI image, it may be advantageous to exclude regions within 1 cm, 1.5 cm, 2 cm, 2.5 cm, or 3 cm from sites that are visualized white in the DTI image, but not visualized white in the DWI image from the candidate positions for administration.

These administration sites and administration routes can be finalized on navigation software using MRI. The MRI used can also be an image taken at a location that is not onsite.

According to one embodiment, for d) selecting, by the computer device, a safe region near the damage position as an administration site, it can be carried out using any approaches known in the art and a combination thereof. For example, an area that is close to the area where the tractography is ruptured or weakened (usually the white area on the DWI) and that is highly safe (an area where there is little damage even if bleeding or allergic reaction occurs: sites other than the site generally referred to as the eloquent area in AVM) is selected as the cell administration site. At the time of selection, it is possible to avoid the high signal intensity area of the T2/FLAIR image and administer cells as close as possible thereto.

According to one embodiment, for e) depicting an administration route between the opening and the administration site, wherein the administration route is depicted with information about the brain route exclusion region, it can be carried out using any approaches known in the art and a combination thereof. Here, in this case, optionally, it is possible to provide suitability information about the administration route from the information about the brain route exclusion region.

As used herein, as for outputting the selected administration site as a graphic display, it can be achieved using any approaches known in the art.

The present disclosure may be provided as a program that causes a computer to achieve the above, or may be provided as a recording medium on which the program is recorded.

Alternatively, in another aspect, the present disclosure provides a system of identifying a route of administration of cells in cell therapy for a central nervous system disorder in a subject.

This system includes at least one of the following configurations:
i) an imaging device for acquiring image data on at least a part of the brain of the subject;
ii) a computer device in communication with the imaging device, for obtaining information on the brain of the subject;
iii) an arithmetic unit for achieving the provision of candidate routes for administering the cells by the following procedure, the procedure including:
   a) identifying, by the computer device, an excision position for passing an administration device for administering the cells in the scalp;
   b) identifying, by the computer device, an opening for allowing the administration device to pass through in the cranial bone for administering cell therapy;
   c) identifying, by the computer device, at least one brain route exclusion region selected from the group consisting of motor fibers, cerebral blood vessels, sulci, and functional sites using the acquired image data and data on the brain of the subject;
   d) selecting, by the computer device, a safe region near the damage position as an administration site; and
   e) depicting an administration route between the opening and the administration site, wherein the administration route is depicted with information about the brain route exclusion region, and optionally providing suitability information about the administration route from the information about the brain route exclusion region, and
iv) a display unit for outputting the selected administration site as a graphic display.

In one embodiment, i) acquiring, by an imaging device, image data on at least part of the brain of the subject may obtain at least part of image data on the brain of the subject using normal contrast procedures such as MRI or CT. Preferably, the image data on the brain to be acquired substantially covers the region to be targeted for cell therapy, and more preferably, it is advantageous that an image of the entire brain is obtained.

(Administration Position Determination)

In one embodiment, the present disclosure provides a method for identifying a site of administration of cells in cell therapy for a central nervous system disorder in a subject. This method includes: A) acquiring, by an imaging device, image data on at least part of the brain of the subject; B) obtaining information on the brain of the subject by a computer device in communication with the imaging device; C) depicting motor fibers by the computer device using the acquired image data and data on the brain of the subject; D) identifying, by the computer device, a damage position in which the motor fibers are damaged, which identifies a part where running data on the motor fibers is lower than other sites to identify the lower part as damaged motor fibers; E) selecting, by the computer device, a safe region near the damage position as an administration site; and F) outputting the selected administration site as a graphic display.

In one embodiment, for A) acquiring, by an imaging device, image data on at least part of the brain of the subject; it can be achieved using any approaches known in the art, which are detailed elsewhere herein, and any of these approaches can be applied.

In one embodiment, for B) obtaining information on the brain of the subject by a computer device in communication with the imaging device, it can be achieved using any approaches known in the art, which are detailed elsewhere herein, and any of these approaches can be applied.

In one embodiment, for C) depicting motor fibers by the computer device using the acquired image data and data on the brain of the subject, it can be achieved using any approaches known in the art, which are detailed elsewhere herein, and any of these approaches can be applied. At least one of DWI, T2, FLAIR, and DTI images can be used to depict motor fibers. For example, using T2 images and FLAIR images, sites that are DWI-negative (that have avoided cell death) but have strong edema (recoverable but not necessarily desirable for administration) are evaluated, and motor fibers are visualized from DTI images, which can evaluate where the motor fibers are ruptured.

In one embodiment, for D) identifying, by the computer device, a damage position in which the motor fibers are damaged, it can be achieved by identifying a part where running data on the motor fibers is lower than other sites to identify the lower part as damaged motor fibers.

In one embodiment, for E) selecting, by the computer device, a safe region near the damage position as an administration site, it can be achieved using any approaches known in the art, which are detailed elsewhere herein; and a site that is highly safe at the time of cell administration and has little damage even if bleeding or allergic reaction occurs (generally sites other than the site referred to as the eloquent area in cerebral arteriovenous malformation (AVM)) can be indicated as a safe region for cell administration; or alternatively, a region that is with a radius of 1.5 cm from the center of the identified damage position, excluding the motor fiber site, and that is a safe region for cell administration, excluding a cell non-administrable region, can be indicated as a candidate position for cell administration.

In one embodiment, for F) outputting the selected administration site as a graphic display, it can be achieved using any approaches known in the art, which are detailed elsewhere herein.

According to one embodiment, the imaging devices include, but are not limited to, MRI, CT, angiography, and ultrasonography. Preferably, MRI is used.

According to one embodiment, the running data on the present disclosure is expressed by FA value (fractional anisotropy value). For example, while it is possible to visually check the ruptured or thinned part of the tractography, it is also possible to program it into a computer. The running of fibers can be quantified (FA value), and the part where this value is significantly lower than other sites (for example, 40%, 50%, 60%, etc.) can be extracted and that site can be evaluated as an injured site. Therefore, the decrease in running data at sites where the running data on motor fibers is lower than other sites may be at least 40%, 50%, 60%, or lower. Alternatively, a site that is as close as possible (for example, within 2 cm, within 2.5 cm, within 3 cm, within 3.5 cm, within 4 cm) and that is not considered to have an important role in neural function can be selected as an administration site. Preferably, the safe region selected from a position that is located within a radius of about 1.5 cm from the damage position and that is not considered to have an important role in nerve function. Since the locations of the parts that have an important role for neural function have already been identified in humans with almost no individual difference, it is possible to incorporate these parts into the computer in advance. For example, while left-handed people are almost the same as right-handed people, there are, very rarely, people who are left-handed and have functions on the opposite side. Mainly in the area of language, both right-handed and left-handed people usually have a language field in the left hemisphere; however, there are left-handed people whose language field is in the right hemisphere on rare occasions, which can be identifiable. That is, upon confirming the language field of the left-handed people in advance by other methods (MRI), care must be taken when the language field is found in the right hemisphere and when an administration route and an administration site passing therethrough are set. Those skilled in the art, however, can appropriately perform the above, and it is also possible to design the above as a computer program.

According to one embodiment, the administration site can be positioned on the caudal side of the brain (caudal side of the injured part) with respect to the damage position. It can be said that this is commonly an expression of hitting from the bottom.

According to one embodiment, the administration site is determined for each damage position.

In one embodiment, there are one or more administration sites for the damage position. The number of administration sites can be appropriately determined by those skilled in the art depending on the case, and can be determined by those skilled in the art based on the relative relationship between the amount of cells to be administered and the brain region to be recovered.

In one embodiment, among the visualized motor fibers, if the brain damage is strong and not visualized, the present disclosure is characterized by determining the damaged part by referring to the contralateral healthy motor fibers. This can be achieved simply by taking symmetry.

The present disclosure may be provided as a program that causes a computer to achieve the above, or may be provided as a recording medium on which the program is recorded.

Alternatively, in another aspect, the present disclosure provides a system of identifying a site of administration of cells in cell therapy for a central nervous system disorder in a subject. This system includes: A) an imaging device for acquiring image data on at least a part of the brain of the subject; B) a computer device in communication with the imaging device, for obtaining information on the brain of the subject, the computer device capable of depicting motor fibers using the acquired image data and data on the brain of the subject, identifying a damage position in which the motor fibers are damaged, identifying a part where running data on the motor fibers is lower than other sites to identify the lower part as damaged motor fibers, and selecting a safe region near the damage position as an administration site; and D) a display unit for outputting the administration site as a graphic display.

(Method of Determining a Passing Region for an Administration Needle for Administering Cells)

In one aspect, the present disclosure provides a method of determining a passing region for an administration needle for administering cells.

In this aspect of the present disclosure, the present disclosure provides a method for identifying a passing region for an administration needle for administration of cells in cell therapy for a central nervous system disorder in a subject, the method including:

A) acquiring image data on at least part of the brain of the subject using an imaging device;

B) obtaining information on the brain of the subject by a computer device in communication with the imaging device;

C) depicting, by the computer device, a blood vessel from the acquired image data and the information on the brain of the subject;

D) identifying, by the computer device, a route range that does not allow penetration of the blood vessel;

E) identifying, by the computer device, a sulcus non-invasive range where a needle does not come out of the sulcus after the needle is inserted into the brain;

F) setting, by the computer device, a route within a range where the route ranges calculated in (D) and (E) overlap with each other; and G) outputting the set route as a graphic display.

In one embodiment, for A) acquiring image data on at least part of the brain of the subject using an imaging device, it can be achieved using any approaches known in the art, which are detailed elsewhere herein, and any of these approaches can be applied.

In one embodiment, for B) obtaining information on the brain of the subject by a computer device in communication with the imaging device, it can be achieved using any approaches known in the art, which are detailed elsewhere herein, and any of these approaches can be applied.

In one embodiment, for C) depicting, by the computer device, a blood vessel from the acquired image data and the information on the brain of the subject, it can be achieved using any approaches known in the art, and any of these approaches can be applied. For example, at least one of a DWI image, a T2 image, a FLAIR image, and a DTI image can be used to depict blood vessels. This can be achieved by, but not limited to, using gadolinium-enhanced T1 images and identifying strong signals, while utilizing the fact that only blood vessels are strongly visualized with high signals. It is also possible to use the original image of MRA (magnetic resonance angiography) to visualize blood vessels.

In one embodiment, for D) identifying, by the computer device, a route range that does not allow penetration of the blood vessel, it can be achieved using any approaches known in the art, and any of these approaches can be applied. For example, the route range can be identified by depicting a blood vessel using at least one of a DWI image, a T2 image, a FLAIR image, and a DTI image, and using the result to identify a route or range that does not allow the penetration. It is also possible to use the original image of MRA (magnetic resonance angiography) to visualize blood vessels.

In one embodiment, for E) identifying, by the computer device, a sulcus non-invasive range where a needle does not come out of the sulcus after the needle is inserted into the brain, it can be achieved using any approaches known in the art, and any of these approaches can be applied. For example, the route range can be identified by depicting a blood vessel using at least one of a DWI image, a T2 image, a FLAIR image, and a DTI image, and using the result to identify a sulcus non-invasive range where a needle does not come out of the sulcus after the needle is inserted into the brain. For example, this is based on an MRI image and can be achieved by measuring at least DWI, T2, FLAIR, and DTI with regard to the MRI image.

In one embodiment, for F) setting, by the computer device, a route within a range where the route ranges calculated in (D) and (E) overlap with each other, it can also be achieved using any approaches known in the art, and any of these approaches can be applied. For example, it is an approach for selecting an overlapping range as an appropriate candidate route, by calculating, using the information obtained in the steps D) and E).

In one embodiment, for G) outputting the set route as a graphic display, it can be achieved using any approaches known in the art, which are detailed elsewhere herein, and any of these approaches can be applied.

In one embodiment, when tractography is visualized in a diffusion tensor (DTI) image, a site that meets conditions of: (a) normal brain tissue that is as close as possible to an area where the tractography is raptured or weakened in the DTI image (usually a white area with DWI in the acute phase of cerebral infarction; high signal intensity in T2/FLAIR in the chronic phase of cerebral infarction; high signal intensity in CT in the acute phase of trauma/cerebral hemorrhage; high signal intensity in T2/FLAIR in the chronic phase of trauma/cerebral hemorrhage); and (b) a highly safe region (an area where there is little damage even if bleeding or allergic reaction occurs: a site other than the site generally referred to as an eloquent area* in AVM), and (c) optionally, a part that avoids, but is as close as possible to, the high signal intensity area in the T2/FLAIR image, is selected as an administration site. On the other hand, when tractography is not visualized in the diffusion tensor image, (aa) the setting for ROI for visualizing tractography is set solely for each of the precentral gyrus, the crus posterius capsulae internae, and the bridge (usually, nerve fibers that pass through the following three: the precentral gyrus, the crus posterius capsulae internae, and the bridge are often selected.), and with the visualized tractography used as a reference, from among them, normally expected motor fibers in humans are selected, and (bb) when tractography is not visualized even in the (aa), running of motor fibers is estimated with reference to tractography on the contralateral side, and a site where an injured site indicated as high signal intensity in a DWI image in the acute phase, or an injured site indicated as low signal intensity in a T2/FLAIR image in the chronic phase, overlaps with an estimated passing point of tractography is estimated to be the site where motor fibers are ruptured, to perform the procedure that is performed when tractography is visualized in the diffusion tensor image.

In one embodiment, as to the selection of the administration site, the current region damaged by the cerebral infarction is determined in the DWI region, and the subject region is excluded from the selection. For example, the T2 high signal is favorable for determining the damaged part over time. It may be advantageous that: a site that is DWI-negative but has strong edema in the T2 image and a FLAIR image is also excluded from the selection; and motor fibers are visualized in a DTI region, and the region of the visualized motor fibers is excluded from the selection.

In one embodiment, the blood vessels that the method according to the present disclosure should avoid as a route include a thick vein that flows from the surface of the brain into the superior sagittal sinus.

In one embodiment, as to the identifying of a blood vessel, it is possible to decide the blood vessel by using a gadolinium-enhanced T1 image and utilizing the fact that only the blood vessel is strongly visualized with a high signal. Specifically, when the signal intensity (signal intensity) is quantified while the inside of the brain is used as a pixel image, two peaks: the brain parenchyma (low signal) and the blood vessel (high signal), are confirmed. The high signal intensity area thereof is decided as a blood vessel, or a normal T1-weighted image that does not use gadolinium is also taken at the same time, and an image obtained by subtracting it from the gadolinium-enhanced T1 image is prepared, and similar pixel image signal intensity is generated, thereby evaluating a single peak (blood vessel) that emerges. For visualizing the blood vessel, it is also possible to use the original image of MRA (magnetic resonance angiography) and measure the signal intensity with the pixel image to confirm the blood vessel based on the fact that the peak value thereof is higher than other parts of the brain.

In one embodiment, as for the identifying of the blood vessel, the identifying is based on an MRI image and is achieved by measuring at least one, two, three or four of at least DWI, T2, FLAIR and DTI, with regard to the MRI image. While not wishing to be bound by theory, it is preferable to have FLAIR, GdT1 and DTI. DWI is a convenient imaging method in which the area of cerebral infarction appears white for only one week after the onset. Usually, whether or not one have a cerebral infarction is decided by this. Since the exemplary clinical trial includes patients in the acute phase, DWI is very useful in determining which part has been injured and paralyzed; however, in chronic patients over time, taking DWI may not give much useful information because such a part does not appear white (the period is over). Furthermore, DWI may not be evaluated for trauma or cerebral hemorrhage. Furthermore, T2 and FLAIR give very similar images, and FLAIR has a particularly large amount of information. Thus, when it comes to the minimum sequence required to calculate the optimal administration site and administration route on the app, it may be advantageous to include FLAIR, gadolinium-enhanced T1 and DTI. Alternatively, preferred sequences could also be depicted as (1) FLAIR images, (3) T2 images, and (3) gadolinium-enhanced T1 images. This exemplifies three parameters that are customarily used to build some of the navigation software (e.g., those provided by Medtronic). As described above, FLAIR, GdT1, and DTI are examples of the minimum requirements. As an illustrative example, it is also possible to create a navigation with FLAIR/GdT1/T2 and decide the area while looking at the DWI and DTI on another computer.

In one embodiment, regions in the brain can be classified as below when signal intensities are plotted on T2-weighted and FLAIR (fluid-attenuated inversion-recovery) images on MRI.

TABLE 1

| brain region | T2 image | FLAIR mage |
| --- | --- | --- |
| normal brain parenchyma | middle signal | middle signal |
| brain sulcus | high signal | low signal |
| brain edema | high signal | high signal |

When it is sometimes difficult to distinguish between the low signal of FLAIR in the sulcus and the signal in FLAIR of the normal brain parenchyma, it is possible to determine the site more accurately by using the T2 high signal of the sulcus and the T2 medium signal of the normal brain parenchyma.

In one embodiment, the identification of a sulcus non-invasive route is achieved by confirming with a T2-weighted image and a FLAIR (fluid-attenuated inversion-recovery) image on MRI. In the T2 image, normal brain parenchyma is visualized with medium signal, while sulci and intracerebral edema are visualized with high signal. Furthermore, in the FLAIR image, normal brain parenchyma is visualized with a medium signal, sulci are visualized with a low signal, and intracerebral edema is visualized with a high signal. This makes it easy to identify the sulcus. Specifically, A) in FLAIR, when the signal intensity is plotted on a pixel image of the brain, there are two peaks that are distinguished by the normal brain parenchyma (medium signal) and the sulcus (low signal). The low signal intensity area thereof is decided to be the sulcus. B) In T2-weighted image, when the signal intensity is plotted on a pixel image of the brain, there are two peaks that are distinguished by the normal brain parenchyma (medium signal) and the sulcus (high signal) The high signal intensity area is decided to be the sulcus. The sulcus confirmed in both of these is decided to be the actual sulcus. In one embodiment, as to the confirmation by T2-weighted image and FLAIR (fluid-attenuated inversion-recovery) image on MRI, A) in FLAIR, when the signal intensity is plotted on a pixel image of the brain, there are two peaks that are distinguished by the normal brain parenchyma (medium signal) and the sulcus (low signal). The low signal intensity area is decided to be the sulcus.

B) In T2-weighted image, when the signal intensity is plotted on a pixel image of the brain, there are two peaks that are distinguished by the normal brain parenchyma (medium signal) and the sulcus (high signal). The high signal intensity area is decided to be the sulcus. The sulcus confirmed in both of these is decided to be the actual sulcus.

The present disclosure may be provided as a program that causes a computer to achieve the above, or may be provided as a recording medium on which the program is recorded.

Alternatively, in another aspect, the present disclosure provides a system of identifying a passing region for an administration needle for administration of cells in cell therapy for a central nervous system disorder in a subject. The system includes: A) an imaging device for acquiring image data on at least a part of the brain of the subject; B) a computer device in communication with the imaging device, for obtaining information on the brain of the subject, where the computer device depicts a blood vessel from the acquired image data and information on the brain of the subject, and identifies a route range that does not allow penetration of the blood vessel, identifies a sulcus non-invasive range where a needle does not come out of the sulcus after the needle is inserted into the brain, and sets a route within a range where the route ranges calculated in (D) and (E) overlap with each other; and G) a display unit for outputting the set route as a graphic display.

(Prevention of Cerebrospinal Fluid Leakage)

In one aspect, the present disclosure provides a method of preventing cerebrospinal fluid leakage in the brain of a subject, the method including: A) incising the dura mater present on a surface of the brain; and B) coagulating and adhering the arachnoid membrane and pia mater on a brain surface at a planned puncture initiating site using an electrosurgical device, such as an electrosurgical instrument including a bipolar coagulation tweezer, where the coagulating and adhering are performed until the arachnoid becomes cloudy, or where an image condition or output condition under which the arachnoid is understood to become cloudy is set. Here, the image condition under which the arachnoid is understood to become cloudy is: for example, a condition under which the cloudiness of the arachnoid can be identified by visual inspection; a condition under which the cloudiness of the arachnoid can be identified by setting the level of the image displaying the arachnoid membrane through a camera etc. to the level at which the microvessels present on the surface of the brain can no longer be confirmed; or a condition under which the cloudiness of the arachnoid can be identified by setting the level of the image displaying the arachnoid membrane through a camera etc. to the level known to achieve clouding of the arachnoid, in accordance with the type of machines for outputting.

The present disclosure may be provided as a program that causes a computer to achieve the above, or may be provided as a recording medium on which the program is recorded.

In one embodiment, the prevention of cerebrospinal fluid leakage in the brain is performed in cell therapy for a central nervous system disorder of the subject.

In a further embodiment, the method of preventing cerebrospinal fluid leakage according to the present disclosure includes C) administering cells required for the subject.

In another aspect, the present disclosure provides a system for preventing cerebrospinal fluid leakage in the brain of a subject, the system including A) an incision tool that cuts through the dura mater present on a surface of the brain; B) an electrosurgical device, such as an electrosurgical instrument including a bipolar coagulation tweezer, the electrosurgical device configured to coagulate and adhere the arachnoid membrane and pia mater on a brain surface at a planned puncture initiating site, where the electrosurgical device is operated until the arachnoid becomes cloudy or can be set to an image or output condition with which the arachnoid is understood to become cloudy; and C) a sensor that can detect the cloudiness of the arachnoid membrane.

In one aspect, the present disclosure provides a method for identifying a route of administration of cells in cell therapy for a central nervous system disorder in a subject, the method including:

i) acquiring, by an imaging device, image data on at least part of the brain of the subject;
ii) obtaining information on the brain of the subject by a computer device in communication with the imaging device;
iii) providing a candidate for a route of administration of cells by the following procedure, the providing step comprising:
aa) selecting, by the computer device, a safe region near a damage position as an administration site;
bb) identifying an administration route to the selected administration site; and cc) optionally, selecting, by the computer device, an excision position for passing an administration device for administering the cells in the scalp, and iv) outputting the selected administration site as a graphic display.

In other aspects, the present disclosure provides a method for identifying a route of administration of cells in cell therapy for a central nervous system disorder in a subject, the method including:

i) acquiring, by an imaging device, image data on at least part of the brain of the subject;

ii) obtaining information on the brain of the subject by a computer device in communication with the imaging device;

iii) providing a candidate for a route of administration of cells by the following procedure, the providing step including:

a) optionally, selecting, by the computer device, an excision position for passing an administration device for administering the cells in the scalp;

b) selecting, by the computer device, an opening for allowing the administration device to pass through in the cranial bone for administering cell therapy;

c) identifying, by the computer device, at least one brain route exclusion region selected from the group consisting of motor fibers, cerebral blood vessels, sulci, and functional sites using the acquired image data and data on the brain of the subject;

d) selecting, by the computer device, a safe region near the damage position as an administration site; and e) depicting an administration route between the opening and the administration site, wherein the administration route is depicted with information about the brain route exclusion region, and optionally providing suitability information about the administration route from the information about the brain route exclusion region, and iv) outputting the selected administration site as a graphic display.

In one aspect, the present disclosure provides a method of predicting the probability of occurrence of adverse effects of cell therapy on a central nervous system disorder in a subject, the method including:

1) inputting a group of data indicating a cell administration position and data on the occurrence of adverse effects of cell therapy for each cell administration position into an artificial intelligence model as learning data and causing the artificial intelligence model to learn the learning data;

2) acquiring a group of data indicating a cell administration position;

3) inputting the group of data indicating a cell administration position acquired in the 2) into the learned artificial intelligence model; and 4) causing the learned artificial intelligence model to calculate the probability of occurrence of adverse effects of cell therapy.

In one embodiment, the group of data indicating a cell administration position includes data on at least one of a distance between an administration position and a brain surface, a distance between an administration position and a damage position, a distance between an administration position and an edema area, and whether the administration position is a site other than the site referred to as the eloquent area in cerebral arteriovenous malformation (AVM).

In some embodiments, the group of data indicating a cell administration position includes a combination of a distance between an administration position and a brain surface, a distance between an administration position and a damage position, a distance between an administration position and an edema area, and whether the administration position is a site other than the site referred to as the eloquent area in cerebral arteriovenous malformation (AVM).

In another aspect, the present disclosure provides a method of predicting the probability of occurrence of adverse effects of cell therapy on a central nervous system disorder in a subject, the method including:

1) inputting a group of data indicating a passing region for an administration needle for administering cells, and data on adverse effects of cell therapy for each passing region for an administration needle for administering cells, into an artificial intelligence model as learning data, and causing the artificial intelligence model to learn the learning data;

2) acquiring a group of data indicating a passing region for an administration needle for administering cells;

3) inputting the group of data indicating a passing region for an administration needle for administering cells acquired in the 2) into the learned artificial intelligence model;

4) causing the learned artificial intelligence model to calculate the probability of occurrence of adverse effects of cell therapy.

In one embodiment, the group of data indicating a passing region for an administration needle for administering cells includes at least one of: a distance between the cranial bone and the brain surface directly below the skin through which an administration needle passes; whether the eloquent area is directly below an insertion point of an administration needle; whether there is a thick vein directly below an insertion point of an administration needle; whether an administration needle passes through an artificial object, such as an artificial bone, an artificial dura mater or a titanium plate; a distance between the sulcus and an administration needle; and a distance between an administration needle and a thick blood vessel in the brain.

In other embodiments, the group of data indicating a passing region for an administration needle for administering cells includes a combination of: a distance between the cranial bone and the brain surface directly below the skin through which an administration needle passes; whether the eloquent area is directly below an insertion point of an administration needle; whether there is a thick vein directly below an insertion point of an administration needle; whether an administration needle passes through an artificial object, such as an artificial bone, an artificial dura mater or a titanium plate; a distance between the sulcus and an administration needle; and a distance between an administration needle and a thick blood vessel in the brain.

In one aspect, the present disclosure provides a method of predicting the probability of occurrence of adverse effects of cell therapy on a central nervous system disorder in a subject, the method including:

1) inputting a group of data indicating a cell administration position and a group of data indicating a passing region for an administration needle for administering cells to a cell administration position, and the group of data indicating a cell administration position and data on adverse effects of cell therapy for each passing region for the administration needle for administering cells to the cell administration position, into an artificial intelligence model as learning data, and causing the artificial intelligence model to learn the learning data;

2) acquiring a group of data indicating a cell administration position and a group of data indicating a passing region for an administration needle for administering cells to a cell administration position;
3) inputting the group of data indicating a cell administration position and the group of data indicating a passing region for an administration needle for administering cells to a cell administration position acquired in the 2) into the learned artificial intelligence model;
4) causing the learned artificial intelligence model to calculate the probability of occurrence of adverse effects of cell therapy.

In one embodiment, the group of data indicating a cell administration position includes a combination of a distance between an administration position and a brain surface, a distance between an administration position and a damage position, a distance between an administration position and an edema area, and whether the administration position is a site other than the site referred to as the eloquent area in cerebral arteriovenous malformation (AVM).

In some embodiments, the group of data indicating a passing region for an administration needle for administering cells to a cell administration position includes a combination of: a distance between the cranial bone and the brain surface directly below the skin through which an administration needle passes; whether the eloquent area is directly below an insertion point of an administration needle; whether there is a thick vein directly below an insertion point of an administration needle; whether an administration needle passes through an artificial object, such as an artificial bone, an artificial dura mater or a titanium plate; a distance between the sulcus and an administration needle; and a distance between an administration needle and a thick blood vessel in the brain.

In other embodiments, the group of data indicating a cell administration position includes at least one of: a distance between an administration position and a brain surface, a distance between an administration position and a damage position, a distance between an administration position and an edema area, and whether the administration position is a site other than the site referred to as the eloquent area in cerebral arteriovenous malformation (AVM); and the group of data indicating a passing region for an administration needle for administering cells to a cell administration position includes at least one of: a distance between the cranial bone and the brain surface directly below the skin through which an administration needle passes; whether the eloquent area is directly below an insertion point of an administration needle; whether there is a thick vein directly below an insertion point of an administration needle; whether an administration needle passes through an artificial object, such as an artificial bone, an artificial dura mater or a titanium plate; a distance between the sulcus and an administration needle; and a distance between an administration needle and a thick blood vessel in the brain.

The present disclosure also provides a program for performing the above-mentioned method, a recording medium having the program stored thereon, and a device and system for performing the above-mentioned method. This method can be activated on the Internet, where the administrator may be allowed to acquire the obtained data (so-called Google, Facebook, etc.) so that data for better methods can be accumulated. Post-operative images and motor function recovery assessment data can also be entered to evaluate the adverse effects of cell therapy.

(Program Configuration Examples)

According to one embodiment, the present disclosure can be provided as a program, which captures MRI images of the brain of a patient with cerebral infarction and measures DWI, T2, FLAIR and DTI on the captured MRI images. This can be achieved by incorporating the images obtained by the measurement into the program.

This program performs the following steps to determine a cell administration site. Specifically, a pre-incorporated site that is highly safe at the time of cell administration and has little damage even if bleeding or allergic reaction occurs (generally sites other than the site referred to as the eloquent area in cerebral arteriovenous malformation (AVM)) is indicated as a safe region for cell administration; in the case where the patient is in the acute phase of trauma/cerebral hemorrhage, high signal intensity regions (at least 50 or more in the Hansfield unit) on CT are indicated as cell non-administrable regions; regions within 2 cm, 1 cm, or 3 cm from the brain surface are indicated as cell non-administrable regions; regions within 0.5 cm from sites that are visualized white in the DTI image, but not visualized white in the DWI image are indicated as cell non-administrable regions; in the T2 image and FLAIR image, sites where edema is strongly present are indicated as cell non-administrable regions; in the DTI image, the precentral gyrus, the crus posterius capsulae internae, and the bridge are selected as a region of interest (ROI), motor fibers are visualized, a part where running data on the motor fibers is lower than other sites (where the FA value is at least 50% or more lower) is identified as a damage position; and a region that is with a radius of 1.5 cm centered on the identified damage position, excluding the motor fiber site, and that is a safe region for cell administration, excluding a cell non-administrable region, can be indicated as a candidate position for cell administration.

Alternatively, the above can be achieved with the following configurations. For example, MRI images of the brain of a patient with cerebral infarction are captured, and DWI, T2, FLAIR and DTI are measured on the captured MRI images. The images obtained by the measurement are incorporated into a computer; and an exemplary program of the present disclosure can achieve the above by performing the following: a cell administration site is determined; a pre-incorporated site that is highly safe at the time of cell administration and has little damage even if bleeding or allergic reaction occurs (generally sites other than the site referred to as the eloquent area in cerebral arteriovenous malformation (AVM)) is indicated as a safe region for cell administration; in the case where the patient is in the acute phase of trauma/cerebral hemorrhage, high signal intensity regions on CT are indicated as cell non-administrable regions; regions within 2 cm from the brain surface are indicated as cell non-administrable regions; in the T2 image and FLAIR image, sites where edema is strongly present are indicated as cell non-administrable region; in the case where injury damage in the brain is considerable and motor fibers cannot be visualized even if the precentral gyrus, the crus posterius capsulae internae and the bridge are selected as the ROI or even with the precentral gyrus, the crus posterius capsulae internae, and the bridge alone, the running of nerve fibers is estimated with reference to healthy motor fibers on a contralateral side; and a region that is with a radius of 1.5 cm centered on the identified damage position, excluding the motor fiber site, and that is a safe region for cell administration, excluding a cell non-administrable region, is indicated as a candidate position for cell administration.

In addition, the present disclosure can be provided as a program for determining a cell administration position. This program captures MRI images of the brain of a patient with a cerebral infarction and measures DWI, T2, FLAIR and DTI on the captured MRI images. The images obtained by the measurement are incorporated into a computer, and the program according to the present disclosure performs the following in order to determine a cell administration site. Specifically, a pre-incorporated site that is highly safe at the time of cell administration and has little damage even if bleeding or allergic reaction occurs (generally sites other than the site referred to as the eloquent area in cerebral arteriovenous malformation (AVM)) is indicated as a safe region for cell administration; in the case where the patient has a chronic phase of cerebral infarction or a chronic phase of trauma/cerebral hemorrhage, a high signal intensity region in T2/FLAIR (A) in FLAIR, when the signal intensity is plotted on a pixel image of the brain, there are two peaks that are distinguished by the normal brain parenchyma (medium signal) and the sulcus (low signal). The low signal intensity area thereof is decided to be the sulcus; B) In T2-weighted image, when the signal intensity is plotted on a pixel image of the brain, there are two peaks that are distinguished by the normal brain parenchyma (medium signal) and the sulcus (high signal). The high signal intensity area is decided to be the sulcus. The sulcus confirmed in both of them is decided to be the actual sulcus) is indicated as a cell non-administrable region; regions within 2 cm from the brain surface are indicated as cell non-administrable regions; regions within 0.5 cm from sites that are visualized white in the DTI image, but not visualized white in the DWI image are indicated as cell non-administrable regions; in the T2 image and FLAIR image, sites where edema is strongly present are indicated as cell non-administrable region; in the DTI image, the precentral gyrus, the crus posterius capsulae internae, and the bridge are selected as a region of interest (ROI), motor fibers are visualized, a part where running data on the motor fibers is lower than other sites (where the FA value is at least 50% or more lower) is identified as a damage position; and a region that is with a radius of 1.5 cm centered on the identified damage position, excluding the motor fiber site, and that is a safe region for cell administration, excluding a cell non-administrable region, can be indicated as a candidate position for cell administration.

As to another configuration example, and for example, as to an example of the program according to the present disclosure, it is also possible to determine the cell administration position when the injury damage in the brain is considerable. In this case, the program captures MRI images of the brain of a patient with a cerebral infarction and measures DWI, T2, FLAIR and DTI on the captured MRI images. The images obtained by the measurement are incorporated into a computer, so that a cell administration site can be determined. Here, the computer program can perform the following: a pre-incorporated site that is highly safe at the time of cell administration and has little damage even if bleeding or allergic reaction occurs (generally sites other than the site referred to as the eloquent area in cerebral arteriovenous malformation (AVM)) is indicated as a safe region for cell administration; in the case where the patient has a chronic phase of cerebral infarction or a chronic phase of trauma/cerebral hemorrhage, high signal intensity regions on T2/FLAIR are indicated as cell non-administrable regions; regions within 2 cm from the brain surface are indicated as cell non-administrable regions; regions within 0.5 cm from sites that are visualized white in the DTI image, but not visualized white in the DWI image are indicated as cell non-administrable regions; in the T2 image and FLAIR image, sites where edema is strongly present are indicated as cell non-administrable regions; in the case where injury damage in the brain is considerable and motor fibers cannot be visualized even if the precentral gyrus, the crus posterius capsulae internae and the bridge are selected as the ROI or even with the precentral gyrus, the crus posterius capsulae internae, and the bridge alone, the running of nerve fibers is estimated with reference to healthy motor fibers on a contralateral side; and a region that is with a radius of 1.5 cm centered on the identified damage position, excluding the motor fiber site, and that is a safe region for cell administration, excluding a cell non-administrable region, can be indicated as a candidate position for cell administration.

As an example of the program in the present disclosure, for example, provided is a program to select one of candidate positions for cell administration and then determine a cell administration route. This exemplary program captures MRI images of the brain of a patient with cerebral infarction and allows the computer to take in gadolinium-enhanced T1, T2, FLAIR and DTI images with regard to the captured MRI images. Here, this program performs the steps below to determine the cell administration route. Specifically, the skin region where the distance between the brain surface directly below the skin and the cranial bone is less than 10 mm and the apex of the gyrus is directly below the skin can be indicated as a recommended insertion region. For example, it is possible to provide classification in three stages: if the distance between the brain surface and the cranial bone is less than 5 mm, it is safe (recommended), if the distance is 5 mm or more and less than 10 mm, administration is allowed (medium difficulty), and if the distance is 10 mm or more, administration is not allowed (high difficulty). This makes it possible to provide software (application) that allows physicians to select various routes. The numerical values for classifying the distance between the brain surface and the cranial bone into safe (recommended), administrable (medium difficulty) and non-administrable (high difficulty) can be freely adjusted by the physicians.

In addition, the region of the skin directly underneath the eloquent area is indicated as a non-insertable region, and a skin region with a thick vein directly underneath, in the gadolinium-enhanced T1 image, is indicated as a non-insertable region. Here, the thickness of the vein can be determined as follows. When the signal intensity (signal intensity) is quantified while the inside of the brain is used as a pixel image, two peaks: the brain parenchyma (low signal) and the blood vessel (high signal), are confirmed. The high signal intensity area thereof is decided as a blood vessel, or a normal T1-weighted image that does not use gadolinium is also taken at the same time, and an image obtained by subtracting it from the gadolinium-enhanced T1 image is prepared, and similar pixel image signal intensity is generated, thereby evaluating a single peak (blood vessel) that emerges. Furthermore, for visualizing the blood vessel, it is also possible to use the original image of MRA (magnetic resonance angiography) and measure the signal intensity with the pixel image to confirm the blood vessel based on the fact that the peak value thereof is higher than other parts of the brain. In addition, areas with an artificial object, such as an artificial bone, an artificial dura mater or a titanium plate can be indicated as non-administrable sites, and the sulcus region, in FLAIR/T2 images, can be indicated as a non-administrable region. Here, the sulcus region can be decided as follows. A) in FLAIR, when the signal intensity is plotted on a pixel image of the brain, there are two peaks that are distinguished by the normal brain parenchyma (medium signal) and the sulcus (low signal). The low signal intensity area thereof is decided to be the sulcus. B) In T2-weighted image, when the signal intensity is plotted on a pixel image of the brain, there are two peaks that are distinguished by the normal brain parenchyma (medium signal) and the sulcus (high signal). The high signal intensity area is decided to be the sulcus. The sulcus confirmed in both A) and B) is decided to be the actual sulcus. Here, the route through the sulcus is not the preferred option, and moreover, if the distance between the sulcus and the needle is very close, it is likely to damage the blood vessels. Accordingly, it is also possible to classify the degree of safety of the route according to the distance between the sulcus and the needle. For example, it can be classified as follows.

Safe (recommended) range: The distance between the sulcus and the needle is 5 mm or more.
Administrable range (medium difficulty): The distance between the sulcus and the needle is 5 mm or more and less than 10 mm.
Non-administrable range (high difficulty): The distance between the sulcus and the needle is less than 10 mm (including the case where the needle penetrates the sulcus).

The numerical value for classifying the distance between the sulcus and the needle into the safe (recommended) range, administrable range (medium difficulty) and non-administrable range (high difficulty) can also be freely adjusted by the physicians.

Alternatively, in the gadolinium-enhanced T1 image, the region within 1 mm from a thick blood vessel in the brain can be indicated as the non-administrable region. In addition, if the distance between the needle and the thick blood vessel in the brain is very close, it is also likely to damage the blood vessel; and it is also possible to classify the degree of safety of the route according to the distance between the needle and the thick blood vessel in the brain. For example, it can be classified as follows.

Safe (recommended) range: The distance between the needle and the thick blood vessel in the brain is 5 mm or more.
Administrable range (medium difficulty): The distance between the needle and the thick blood vessel in the brain is 5 mm or more and less than 1 mm.
Non-administrable range (high difficulty): The distance between the needle and the thick blood vessel in the brain is less than 1 mm (including the case where the needle penetrates the blood vessel).

The numerical value for classifying the distance between the needle and the thick blood vessel in the brain into the safe (recommended) range, administrable range (medium difficulty) and non-administrable range (high difficulty) can be freely adjusted by the physicians.

In addition, of the linear route connecting the candidate position for cell administration and the recommended insertion region, the distance between the brain surface and the cranial bone is within the safe (recommended) range, the distance between the sulcus and the needle is within the safe (recommended) range, the distance between the needle and the thick blood vessel in the brain is within the safe (recommended) range, and it is possible to preferentially indicate the route that does not pass through the non-administrable site/region.

Alternatively, in an exemplary program, it is possible to capture MRI images of the brain of a patient with cerebral infarction, cause a computer to take in gadolinium-enhanced T1, T2, FLAIR and DTI images of the captured MRI images, and determine a cell administration route.

In this program, it is possible to: indicate a skin region where the distance between the brain surface directly below the skin and the cranial bone is less than 5 mm and the apex of the gyrus is directly below the skin, as a recommended insertion region; indicate a skin region directly under the eloquent area as a non-insertable region; indicate a skin area with a thick vein directly underneath, in the gadolinium-enhanced T1 image, as a non-insertable region; indicate a previous skin incision site as a skin depression on an MRI image; then, indicate a region of a previous incision as a recommended incision region, a region less than 3 cm from the previous incision as an incisable region, and a region 3 cm or more away from the previous incision as a non-incisable region; indicate an area with an artificial object, such as an artificial bone, an artificial dura mater or a titanium plate as a non-administrable site; indicate a sulcus region, in FLAIR/T2 images, as a non-administrable region; indicate a region within 1 mm of the thick blood vessel in the brain and within blood vessels in the sulci, in the gadolinium-enhanced T1 image, as a non-administrable region; and of the linear route connecting the candidate position for cell administration and a region that is a recommended insertion region and that is also a recommended incision region, determine the distance between the brain surface and the cranial bone to be within the safe (recommended) range; determine the distance between the sulcus and the needle to be within the safe (recommended) range; determine the distance between the needle and the thick blood vessel in the brain to be within the safe (recommended) range; and preferentially indicate the route that does not pass through the non-administrable site/region.

References literatures, such as scientific literature, patents and patent applications, cited herein are incorporated herein by reference in their entirety to the same extent that each of the literatures is specifically described.

As described above, the present disclosure has been described while showing preferred embodiments to facilitate understanding. The present disclosure is described hereinafter based on Examples. The above descriptions and the following Examples are not provided to limit the present disclosure, but for the sole purpose of exemplification. Thus, the scope of the present disclosure is not limited to the embodiments or the Examples specifically described herein and is limited only by the scope of claims.

EXAMPLES

Examples will be described hereinafter. The handling of humans used in the examples below was carried out with consent and based on GCP, and when required, in accordance with the standards stipulated by the regulatory agency and the Declaration of Helsinki, while respecting ICH standards, and in accordance with the ethical code stipulated by Hokkaido University. The inventors complied with the standards advocated by the Declaration of Helsinki and ICH, as well as various standards stipulated by the Hokkaido University Ethics Committee, and complied with the standards advocated by the Declaration of Helsinki and ICH, as well as various standards stipulated by the Hokkaido University Ethics Committee. (Sigma-Aldrich, and the like).

Example 1: Determination of Administration Site

According to the present example, motor fibers are visualized by brain MRI in advance to determine the cell administration site. The damaged part of the visualized motor fibers is determined (if the brain damage is strong and the motor fibers are not visualized, refer to the healthy motor fibers on the contralateral side) to select a site that is as close as possible to the site (within a radius of 1.5 cm) and that is not considered to have an important role in nerve function as the administration site.

The procedure is as follows.

The administration site is determined using at least DWI images, T2 images, FLAIR images and DTI images.

First, the region damaged by the cerebral infarction is determined from the DWI image. (Cells should never be administered here because the cells die due to lack of blood flow.) With the use of T2 images and FLAIR images, sites that are DWI-negative (that have avoided cell death) but have strong edema (recoverable but not necessarily desirable for administration) are evaluated, and motor fibers are visualized from DTI images, to evaluate where the motor fibers are ruptured.

An area that is close to the area where the tractography is ruptured or weakened (usually the white area on the DWI) and that is highly safe (an area where there is little damage even if bleeding or allergic reaction occurs: sites other than the site generally referred to as the eloquent area in AVM) is selected as a cell administration site. At the time of selection, care should be taken to avoid high signal intensity areas in the T2/FLAIR image and administer the cells as close as possible thereto.

If the tractography is not visualized because the injury damage is too considerable, the running of nerve fibers is estimated with reference to the contralateral tractography, and an estimated tractography is created, to determine a cell administration site.

Positions close to the brain surface (within 2 cm from the brain surface) are excluded from the candidate positions for administration to prevent cells from coming out of the administration site.

The administration site is finalized on the navigation software using MRI. The MRI used may be an image taken at other hospitals.

Example 2: Administration Position Determination Example 1

The cell administration position was determined in a 74-year-old female with lacunar infarction.

There was a white part on the right radial crown in the DWI image, and thus, this site was decided to be an infarct site (FIG. 1A). From the DTI image, it was found that the infarct site was the path of tractography, that is, it was found that motor nerve fibers (blue) passed through the cerebral infarction (and the signals were less than on the other side); accordingly, it was determined that the motor fibers were ruptured in there and paralysis occurred (FIG. 1B). The upper white matter of the right caudate nucleus was selected, which causes almost no symptoms (silent area) even if cerebral hemorrhage or cell allergy occurs (FIG. 1C). Twenty million cells were administered to the selected position.

(Results)

Three hundred sixty days after the administration, the decrease in NIHSS (National Institute of Health Stroke Scale), which is one of the stroke severity evaluation scales, improvements in functional independence measure (FIM) and Barthel index (BI) were observed; however, the Fugl-Meyer rating (FMA) did not change (Table 2).

TABLE 2

|  | 14 days after offset | 7 days before administration | 1 month later | 3 months later | 6 months later | 12 months later | 24 months later |
| --- | --- | --- | --- | --- | --- | --- | --- |
| NIHSS | 11 | 7 | 6 | 5 | 5 | 5 | 5 |
| mRS | 4 | 4 | 4 | 4 | 4 | 3 | 3 |
| FIM | 76 | 98 | 110 | 109 | 117 | 119 | 123 |
| BI | 40 | 60 | 75 | 80 | 90 | 90 | 85 |
| FMA | 136 | 147 | 144 | 13 | 143 | 144 | 142 |

Example 3: Administration Position Determination Example 2

The cell administration position was determined in a 67-year-old male with cardiogenic embolism and right middle cerebral vein obstruction.

In the DWI image, there was a white part from the radial crown to the crus posterius capsulae internae, and thus, this site was decided to be an infarct site (FIG. 2A). From the DTI image, it was found that motor nerve fibers (blue) passed through the cerebral infarction (and the signals were less than on the other side); accordingly, it was determined that the motor fibers were ruptured in there. In consideration of the infarct site and tractography (FIG. 2B), the site outside the infarct site confirmed by DWI was determined as the administration site (FIG. 2C). Twenty million cells were administered to the selected position.

(Results)

Three hundred sixty days after the administration, the decrease in NIHSS and improvement in FIM and BI were observed; however, FMA did not change. The improvement in motor function over time was observed (Table 3).

TABLE 3

|  | 14 days after offset | 7 days before administration | 1 month later | 3 months later | 6 months later | 12 months later | 24 months later |
| --- | --- | --- | --- | --- | --- | --- | --- |
| NIHSS | 9 | 7 | 7 | 6 | 8 | 6 | 6 |
| mRS | 4 | 4 | 4 | 4 | 4 | 4 | 3 |
| FIM | 51 | 74 | 83 | 84 | 105 | 111 | 104 |
| BI | 40 | 50 | 60 | 65 | 75 | 80 | 70 |
| FMA | 128 | 128 | 124 | 123 | 126 | 145 | 142 |

Example 4: Administration Position Determination Example 3

The cell administration position was determined in a 58-year-old male with atherothrombotic infarction and right cervical carotid artery occlusion.

A white cerebral infarction was observed extensively in the left hemisphere on DWI (FIG. 3A), while the motor fibers visualized by tractography were not visualized in the region of cerebral infarction (due to the wide range of damage) (FIG. 3B). Accordingly, in consideration of (1) normal brain tissue and (2) the contralateral and anatomically inferred running of motor nerve fibers, twenty million cells were administered to the left postcentral gyrus subcortical white matter (FIG. 3C).

(Results)

Three hundred sixty days after the administration, the decrease in NIHSS and improvement in FIM were observed; however, BI and FMA did not change (Table 4).

TABLE 4

|  | 14 days after offset | 7 days before administration | 1 month later | 3 months later | 6 months later | 12 months later |
|---|---|---|---|---|---|---|
| NIHSS | 22 | 19 | 16 | 15 | 15 | 17 |
| mRS | 5 | 5 | 5 | 4 | 4 | 4 |
| FIM | 18 | 26 | 34 | 37 | 39 | 43 |
| BI | 0 | 15 | 15 | 15 | 15 | 20 |
| FMA | 116 | 124 | 123 | 111 | 105 | 97 |

Example 5: Administration Position Determination Example 4

The cell administration position was determined in a 64-year-old male with atherothrombotic infarction and right middle cerebral artery stenosis.

In the DWI image, scattered white areas, which were high signal intensity, were recognized in the left frontal lobe, and thus, this site was decided to be the infarct site (FIG. 4A). From the DTI image, a weak tractography signal was confirmed in the infarcted area, and the signal was less than on the other side. Thus, it was determined that the motor fibers were ruptured in there (FIG. 4B). A site as close as possible to this, which is also a site anterior to the lateral side of the infarct site confirmed by DWI, was determined to be the administration site (FIG. 4C). Fifty million cells were administered to the selected position.
(Results)

One hundred eighty days after the administration, the decrease in NIHSS and improvement in FIM and BI were observed; however, FMA did not change (Table 5).

TABLE 5

|  | 14 days after offset | 7 days before administration | 1 month later | 3 months later | 6 months later | 12 months later |
|---|---|---|---|---|---|---|
| NIHSS | 23 | 21 | 14 | 14 | 14 | 14 |
| mRS | 4 | 4 | 4 | 4 | 4 | 4 |
| FIM | 41 | 45 | 56 | 56 | 57 | 62 |
| BI | 20 | 25 | 50 | 45 | 45 | 45 |
| FMA | 121 | 110 | 112 | 98 | 101 | 103 |

Example 6: Administration Position Determination Example 5

Extensive cerebral infarction occurred in the right hemisphere (FIG. 5A). It was found that motor nerve fibers (blue) passed through the cerebral infarction (and the signal was less than on the other side), and it was considered that nerve fibers were damaged and paralyzed at the site where tractography passed through the DWI (FIG. 5B). Accordingly, cells were administered to the right caudate nucleus, which was near the site and was considered safe (FIG. 5C).
(Results)

One year after the operation, improvement was observed in all of NIHSS, BI, FMA, and FIM (Table 6).

TABLE 6

|  | 14 days after offset | 7 days before administration | 1 month later | 3 months later | 6 months later | 12 months later |
|---|---|---|---|---|---|---|
| NIHSS | 14 | 14 | 11 | 11 | 11 | 10 |
| mRS | 5 | 4 | 4 | 4 | 4 | 3 |

TABLE 6-continued

|  | 14 days after offset | 7 days before administration | 1 month later | 3 months later | 6 months later | 12 months later |
|---|---|---|---|---|---|---|
| FIM | 46 | 62 | 67 | 82 | 98 | 108 |
| BI | 10 | 25 | 40 | 65 | 70 | 75 |
| FMA | 108 | 112 | 122 | 128 | 126 | 136 |

Example 7: Administration Position Determination Example 6

Tractography had passed through a cerebral infarct lesion (DWI positive) in the left internal capsule (FIGS. 6A and 6B), and thus, it was determined that paralysis was caused by the same site, and cells were administered to the left caudate nucleus head in the immediate vicinity of the cerebral infarction lesion (DWI) (FIG. 6C).
(Results)

Half a year after the operation, improvement was observed in all of NIHSS, BI, FMA, and FIM (Table 7).

TABLE 7

|  | 14 days after onset | 7 days before administration | 1 month later | 3 months later | 6 months later |
|---|---|---|---|---|---|
| NIHSS | 13 | 11 | 10 | 9 | 7 |
| mRS | 5 | 5 | 4 | 4 | 3 |
| FIM | 33 | 35 | 68 | 98 | 112 |
| BI | 10 | 15 | 60 | 65 | 85 |
| FMA | 112 | 120 | 128 | 123 | 131 |

Example 8: Administration Position Determination Example 7

There was an acute cerebral infarction, which appeared white in DWI, in the radiate crown in the deep white matter of the right frontal lobe (FIG. 7A). Tractography was not visualized, probably because it was passing through the interior (FIG. 7B). Accordingly, cells were administered to the lateral white matter of the right caudate nucleus, which was close to the assumed tractography from the opposite side and was considered safe (FIG. 7C).
(Results)

One month after the administration, and compared with seven days before the administration, improvements in NIHSS, FIM, BI and FMA were recognized. There was no change in mRS (Table 8).

TABLE 8

|  | 14 days after onset | 7 days before administration | 1 month later |
|---|---|---|---|
| NIHSS | 11 | 9 | 7 |
| mRS | 5 | 4 | 4 |
| FIM | 61 | 77 | 99 |
| BI | 20 | 45 | 65 |
| FMA | 112 | 123 | 141 |

Example 9: Determining the Passing Region for the Administration Needle

According to the present example, thick veins on the surface of the brain were confirmed in advance using brain MRI, and they were formulated so that the needle would not penetrate the same site when the needle passed. In addition, once the needle was inserted into the brain, a passage was selected so that the needle would not come out of the sulcus (the needle can reach the sulci and damage the small veins and arteries that run on the surface of the brain). This approach can be described not only as a method of surgery, but also as a program.

The procedure is as follows.

MRI FLAIR images, T2 images, and gadolinium-enhanced T1 images are used to determine the cell administration route.

If the skin has already been incised, the incision is basically used. If the target Burr hole deviates significantly from the previous skin incision line, it should be coped by making a long incision in the skin and removing the Galea.

The incision site of the skin is confirmed as a skin depression by importing an MRI image into Medtronic's navigation calculation system FlameLink.

If possible, areas with an artificial object, such as an artificial bone, an artificial dura mater or a titanium plate are excluded from the administration route in order to prevent postoperative infection.

The burr hole is selected so that the insertion point does not overlap the functional site.

Where the brain is atrophied and has sunk considerably (about 5 mm), even if the dura mater is incised, the distance to the brain is long, which can be a cause of an accident. Thus, the site where the brain surface is directly below the bone (the apex of the gyrus) is selected as the administration route.

Where the burr hole is located near the midline, there may be a thick vein that perfuses the superior sagittal sinus (SSS) (in some cases, it may have become a venous lake). Thus, FlameLink is used to confirm that there are no thick veins around the dural incision site in advance.

Once in the sulcus, there are possibilities to damage relatively thick blood vessels running on the surface of the brain. Thus, selected is an administration route that enters the brain parenchyma directly below the burr hole and does not appear in the sulcus until the target administration position. As the confirmation of the administration route, performed are: confirmation that the needle traveling in the brain does not appear in the sulcus on the FLAIR/T2 image; and confirmation on gadolinium images that there is no contact with thick blood vessels in the brain and blood vessels around the sulcus.

Example 10: Example of Determining the Passing Region of the Dosing Needle

The cell administration route was determined using FLAIR images, T2 images, and gadolinium-enhanced T1 images of MRI. Since the skin had been previously incised, the route was determined to be a burr hole using the incision. MRI images were imported into Medtronic's navigation calculation system FlameLink, and the incision site of the skin was confirmed as a skin depression, thereby selecting an administration route at a site where the brain surface was directly below the bone (the apex of the gyrus) and in such a manner that the insertion point would not overlap with the functional site. After the administration route was determined, it was confirmed that the needle traveling in the brain did not appear in the sulcus using FLAIR/T2 images, and it was confirmed that there was no contact with thick blood vessels in the brain and the blood vessels around the sulcus, using gadolinium images.

(Results)

No complications, such as intracerebral hemorrhage, were observed in any of the administration cases.

Example 11: Method of Preventing Cerebrospinal Fluid Leakage

According to the present example, an incision of an arachnoid membrane on the surface of the brain causes the cerebrospinal fluid in the brain to flow out. Since the brain exists as if it were floating in the cerebrospinal fluid, a brain shift (sinking) occurs in which the position of the brain shifts over time. To prevent this, there is a method of, before incising the arachnoid membrane, coagulating and adhering the arachnoid membrane and pia mater on the brain surface at the planned puncture site using electrosurgical instruments such as bipolar coagulation tweezers. This can prevent the brain from shifting even when the needle is inserted. This is especially important if multiple punctures are required.

The procedure is as follows.

The arachnoid membrane was coagulated until it became cloudy and the arachnoid membrane was adhered to the pia mater.

Cerebrospinal fluid leakage did not occur even when the arachnoid membrane was incised with the arachnoid membrane and the pia mater adhered with each other, which enabled the cells to be administered to the originally planned site. No brain shift (sinking) occurred either.

Example 12: Example 1 of Program for Determining Cell Administration Position In the present example, determination of the cell administration position using a program is performed.

MRI images of the brain of a patient with cerebral infarction are captured, and DWI, T2, FLAIR, and DTI images are incorporated into the program for the captured MRI images.

The program performs the steps below to determine a cell administration site.

- A pre-incorporated site that is highly safe at the time of cell administration and has little damage even if bleeding or allergic reaction occurs (generally sites other than the site referred to as the eloquent area in cerebral arteriovenous malformation (AVM)) is indicated as a safe region for cell administration.
- The part that appears white in the DWI image is indicated as a cell non-administrable region.
- Regions within 2 cm from the brain surface are indicated as cell non-administrable regions.
- In the T2 image and FLAIR image, the site where edema is strong (a site that meets both A) a high signal intensity area in the FLAIR image plotting signal intensity, and B) a high signal intensity area in the T2-weighted image plotting signal intensity) is indicated as a cell non-administrable region.
- In the DTI image, the precentral gyrus, the crus posterius capsulae internae, and the bridge are selected as a region of interest (ROI), motor fibers are visualized, a part where running data on the motor fibers is lower than other sites (where the FA value (fractional anisotropy value) is at least 50% or more lower) is identified as a damage position.

A region that is with a radius of 1.5 cm centered on the identified damage position, excluding the motor fiber site, and that is a safe region for cell administration, excluding a cell non-administrable region, is indicated as a candidate position for cell administration.

Example 13: Example 2 of Program for Determining Cell Administration Position

In the present example, determination of the cell administration position using a program is performed when the injury damage in the brain is considerable.

MRI images of the brain of a patient with cerebral infarction are captured, and DWI, T2, FLAIR and DTI are measured with regard to the captured MRI images. Images obtained by the measurement are incorporated into the program.

The program performs the steps below to determine a cell administration site.

A pre-incorporated site that is highly safe at the time of cell administration and has little damage even if bleeding or allergic reaction occurs (generally sites other than the site referred to as the eloquent area in AVM) is indicated as a safe region for cell administration.

The part that appears white in the DWI image is indicated as a cell non-administrable region.

Regions within 2 cm from the brain surface are indicated as cell non-administrable regions.

In the T2 image and FLAIR image, the site where edema is strong (a site that meets both A) a high signal intensity area in the FLAIR image plotting signal intensity, and B) a high signal intensity area in the T2-weighted image plotting signal intensity) is indicated as a cell non-administrable region.

If the injury damage in the brain is considerable and motor fibers cannot be visualized even if the precentral gyrus, the crus posterius capsulae internae and the bridge are selected as the ROI or even with the precentral gyrus, the crus posterius capsulae internae, and the bridge alone, the running of nerve fibers is estimated with reference to healthy motor fibers on a contralateral side. A site where an injured site indicated as high signal intensity in the DWI image in the acute phase, or an injured site indicated as low signal intensity in the T2/FLAIR image in the chronic phase, overlaps with an estimated passing point of tractography is estimated to be the site where motor fibers are ruptured.

A region that is with a radius of 1.5 cm centered on the identified damage position, excluding the motor fiber site, and that is a safe region for cell administration, excluding a cell non-administrable region, is indicated as a candidate position for cell administration.

Example 14: Example 3 of Program for Determining Cell Administration Position

In the present example, determination of the cell administration position using a program is performed.

MRI images of the brain of a patient with cerebral infarction are captured, and DWI, T2, FLAIR and DTI are measured with regard to the captured MRI images. Images obtained by the measurement are incorporated into the program.

The program performs the steps below to determine a cell administration site.

A pre-incorporated site that is highly safe at the time of cell administration and has little damage even if bleeding or allergic reaction occurs (generally sites other than the site referred to as the eloquent area in AVM) is indicated as a safe region for cell administration.

If the patient is in the acute phase of trauma/cerebral hemorrhage, the high signal intensity area (at least 50 or more in the Hansfield unit) on CT is indicated as a cell non-administrable region.

Regions within 2 cm from the brain surface are indicated as cell non-administrable regions.

In the T2 image and FLAIR image, the site where edema is strongly present is indicated as a cell non-administrable region.

In the DTI image, the precentral gyrus, the crus posterius capsulae internae, and the bridge are selected as a region of interest (ROI) to visualize the motor fibers, and a part where running data on the motor fibers is lower than other sites (where the FA value is at least 50% or more lower) is identified as a damage position.

A region that is with a radius of 1.5 cm centered on the identified damage position, excluding the motor fiber site, and that is a safe region for cell administration, excluding a cell non-administrable region, is indicated as a candidate position for cell administration.

Example 15: Example 4 of Program for Determining Cell Administration Position

In the present example, determination of the cell administration position using a program is performed when the injury damage in the brain is considerable.

MRI images of the brain of a patient with cerebral infarction are captured, and DWI, T2, FLAIR and DTI are measured with regard to the captured MRI images. Images obtained by the measurement are incorporated into the program.

The program performs the steps below to determine a cell administration site.

A pre-incorporated site that is highly safe at the time of cell administration and has little damage even if bleeding or allergic reaction occurs (generally sites other than the site referred to as the eloquent area in AVM) is indicated as a safe region for cell administration.

If the patient is in the acute phase of trauma/cerebral hemorrhage, the high signal intensity region on CT is indicated as a cell non-administrable region.

Regions within 2 cm from the brain surface are indicated as cell non-administrable regions.

In the T2 image and FLAIR image, the site where edema is strongly present is indicated as a cell non-administrable region.

If the injury damage in the brain is considerable and motor fibers cannot be visualized even if the precentral gyrus, the crus posterius capsulae internae and the bridge are selected as the ROI or even with the precentral gyrus, the crus posterius capsulae internae, and the bridge alone, the running of nerve fibers is estimated with reference to healthy motor fibers on a contralateral side.

A region that is with a radius of 1.5 cm centered on the identified damage position, excluding the motor fiber site, and that is a safe region for cell administration, excluding a cell non-administrable region, is indicated as a candidate position for cell administration.

Example 16: Example 5 of Program for Determining Cell Administration Position In the present example, determination of the cell administration position using a program is performed.

MRI images of the brain of a patient with cerebral infarction are captured, and DWI, T2, FLAIR and DTI are measured with regard to the captured MRI images. Images obtained by the measurement are incorporated into the program.

The program performs the steps below to determine a cell administration site.

- A pre-incorporated site that is highly safe at the time of cell administration and has little damage even if bleeding or allergic reaction occurs (generally sites other than the site referred to as the eloquent area in AVM) is indicated as a safe region for cell administration.
- If the patient has a chronic phase of cerebral infarction or a chronic phase of trauma/cerebral hemorrhage, a site that meets both A) a high signal intensity area in the FLAIR image plotting signal intensity, and B) a high signal intensity area in the T2-weighted image plotting signal intensity is indicated as a cell non-administrable region.
- Regions within 2 cm from the brain surface are indicated as cell non-administrable regions.
- In the T2 image and FLAIR image, the site where edema is strongly present is indicated as a cell non-administrable region.
- In the DTI image, the precentral gyrus, the crus posterius capsulae internae, and the bridge are selected as a region of interest (ROI) to visualize the motor fibers, and a part where running data on the motor fibers is lower than other sites (where the FA value is at least 50% or more lower) is identified as a damage position.
- A region that is with a radius of 1.5 cm centered on the identified damage position, excluding the motor fiber site, and that is a safe region for cell administration, excluding a cell non-administrable region, is indicated as a candidate position for cell administration.

Example 17: Example 6 of Program for Determining Cell Administration Position In the present example, determination of the cell administration position using a program is performed when the injury damage in the brain is considerable.

MRI images of the brain of a patient with cerebral infarction are captured, and DWI, T2, FLAIR and DTI are measured with regard to the captured MRI images. Images obtained by the measurement are incorporated into the program.

The program performs the steps below to determine a cell administration site.

- A pre-incorporated site that is highly safe at the time of cell administration and has little damage even if bleeding or allergic reaction occurs (generally sites other than the site referred to as the eloquent area in AVM) is indicated as a safe region for cell administration.
- If the patient has a chronic phase of cerebral infarction or a chronic phase of trauma/cerebral hemorrhage, a high signal intensity region in T2/FLAIR is indicated as a cell non-administrable region.
- Regions within 2 cm from the brain surface are indicated as cell non-administrable regions.
- In the T2 image and FLAIR image, the site where edema is strongly present is indicated as a cell non-administrable region.
- If the injury damage in the brain is considerable and motor fibers cannot be visualized even if the precentral gyrus, the crus posterius capsulae internae and the bridge are selected as the ROI or even with the precentral gyrus, the crus posterius capsulae internae, and the bridge alone, the running of nerve fibers is estimated with reference to healthy motor fibers on a contralateral side.
- A region that is with a radius of 1.5 cm centered on the identified damage position, excluding the motor fiber site, and that is a safe region for cell administration, excluding a cell non-administrable region, is indicated as a candidate position for cell administration.

Example 18: Example 1 of Program for Determining a Cell Administration Route In the present example, after one of the candidate positions for cell administration is selected, determination of a cell administration route using the program is performed.

MRI images of the brain of a patient with cerebral infarction are captured, and gadolinium-enhanced T1, T2, FLAIR, and DTI images are incorporated into the program with regard to the captured MRI images.

The program performs the steps below to determine a cell administration route.

- The brain regions are classified as follows according to the distance between the brain surface directly below the skin and the cranial bone.
- Safe (recommended) range: The distance between the brain surface and the cranial bone is less than 5 mm.
- Administrable range: The distance between the brain surface and the cranial bone is 5 mm or more and less than 10 mm.
- Non-administrable range: The distance between the brain surface and the cranial bone is 10 mm or more.
- The region of the skin directly under the eloquent area is indicated as a non-insertable region.
- In the gadolinium-enhanced T1 image, the skin region with a thick vein directly underneath is indicated as a non-insertable region.
- Areas with an artificial object, such as an artificial bone, an artificial dura mater or a titanium plate, are indicated as non-administrable sites.
- In the FLAIR/T2 image, a sulcus region (an area that meets both of: A) a low signal intensity area in the FLAIR image plotting signal intensity; and B) a high signal intensity area in the T2-weighted image plotting signal intensity) is indicated as a non-administrable site.
- Areas of the brain are classified as follows according to the distance between the sulcus and the needle.
- Safe (recommended) range: The distance between the sulcus and the needle is 5 mm or more.
- Administrable range: The distance between the sulcus and the needle is 1 mm or more and less than 5 mm.
- Non-administrable range: The distance between the sulcus and the needle is less than 1 mm (including the case when the needle penetrates the sulcus).
- In the gadolinium-enhanced T1 image, the regions of the brain are classified as follows according to the distance between the needle and thick blood vessels in the brain.

Safe (recommended) range: The distance between the needle and the thick blood vessel in the brain is 5 mm or more.

Administrable range: The distance between the needle and a thick blood vessel in the brain is 1 mm or more and less than 5 mm.

Non-administrable range: The distance between the needle and a thick blood vessel in the brain is less than 1 mm (including the case when the needle penetrates the blood vessel).

Of the linear route connecting the candidate position for cell administration and the recommended insertion region, the distance between the brain surface and the cranial bone is within the safe (recommended) range, the distance between the sulcus and the needle is within the safe (recommended) range, the distance between the needle and the thick blood vessel in the brain is within the safe (recommended) range, and the route that does not pass through the non-administrable site/region is preferentially indicated.

Example 19: Example 2 of Program for Determining a Cell Administration Route

In the present example, after one of the candidate positions for cell administration is selected, determination of a cell administration route using the program is performed.

MRI images of the brain of a patient with cerebral infarction are captured, and gadolinium-enhanced T1, T2, FLAIR, and DTI images are incorporated into the program with regard to the captured MRI images.

The program performs the steps below to determine a cell administration route.

The skin region where the distance between the brain surface directly below the skin and the cranial bone is less than 5 mm and the apex of the gyrus is directly below the skin, is indicated as a recommended insertion region.

The region of the skin directly under the eloquent area is indicated as a non-insertable region.

In the gadolinium-enhanced T1 image, the skin region with a thick vein directly underneath is indicated as a non-insertable region.

Previous skin incision sites are indicated as skin depressions in the MRI image; then, regions of previous incision are indicated as recommended incision regions, regions less than 3 cm from the previous incision are indicated as incisable regions, and regions 3 cm or more away from the previous incision are indicated as non-incisable regions.

Areas with an artificial object, such as an artificial bone, an artificial dura mater or a titanium plate are indicated as non-administrable sites.

In the FLAIR/T2 images, sulcus regions are indicated as non-administrable regions.

In the gadolinium-enhanced T1 image, regions within 1 mm of thick blood vessels in the brain and within blood vessels in the sulci are indicated as non-administrable regions.

Of the linear route connecting the candidate position for cell administration and a region that is a recommended insertion region and that is also a recommended incision region, the distance between the brain surface and the cranial bone is within the safe (recommended) range, the distance between the sulcus and the needle is within the safe (recommended) range, the distance between the needle and the thick blood vessel in the brain is within the safe (recommended) range, and the route that does not pass through the non-administrable site/region is preferentially indicated.

Example 20: Example 1 of System for Preventing Cerebrospinal Fluid Leakage

In the present example, disclosed is a system for preventing cerebrospinal fluid leakage using the time of cauterization and bipolar outputs as indicators.

The present system can be used to determine the degree of cloudiness of the arachnoid membrane in arachnoid membrane cauterization. The present system consists of a camera part that obtains the state of the arachnoid membrane as an image and a determination part that determines the degree of cloudiness of the arachnoid membrane image obtained from the camera part. The image of the arachnoid membrane during cauterization obtained from the camera part is transmitted to the determination part. Upon receiving the image of the arachnoid membrane during cauterization, the determination part compares the image with the image of the arachnoid membrane before cauterization. If the blood vessels found in the pre-cauterization arachnoid membrane image are no longer visible in the arachnoid membrane image during cauterization, the determination part indicates a warning to stop the cauterization.

Example 21: Example 2 of System for Preventing Cerebrospinal Fluid Leakage

In the present example, disclosed is a system for preventing cerebrospinal fluid leakage using the time of cauterization and bipolar outputs as indicators.

Inputting of a bipolar output and the area of a planned cauterization region into the present system estimates the time required for cauterization. The present system issues a warning to stop the cauterization after the cauterization has started and the expected cauterization time has elapsed.

Example 22: Example of Predicting the Probability of Occurrence of Adverse Effects of Cell Therapy Based on Cell Administration Position (1) Target Patients Patients with cerebral infarction are targeted.

(2) MRI Image Capturing

For each patient, MRI images of the brain are captured at the time corresponding to the subacute phase and the chronic phase. The image capturing is performed using an MRI apparatus (3T Achieva TX(Philips Medical Systems)) with default settings (b=0, 1000 s mm-2, TR/TE=5032/85 msec, NEX=1, voxel size=3×3×3 mm3, no. of slices=43, 32 diffusion gradient directions).

(3) MRI Image Analysis

Based on the MRI images captured, points such as the distance to the brain surface, the distance to the damage position in the brain, the distance to the edema region, and whether a site is other than the site referred to as the eloquent area in cerebral arteriovenous malformation (AVM), are evaluated to determine a cell administration position.

(4) Preparation and Administration of Bone Marrow Stem Cells

After registering the case, the patient's bone marrow is collected immediately, and cell culture and preparation of bone marrow stem cells are performed at the Cell Processing Center in the Clinical Research and Medical Innovation Center, Hokkaido University Hospital. The prepared bone marrow stem cells (20 million or 50 million/patient) are administered directly into the patient's brain three to five weeks after the bone marrow collection.

(5) Adverse Effect Evaluation

The patients after administration are evaluated for adverse effects due to cell therapy (adverse effects on motor function, sensory function, language function or vision, blood loss, etc.).

(6) Results

Correlation is found between the probability of occurrence of adverse effects of cell therapy and points such as the distance to the brain surface, the distance to the damage position in the brain, the distance to the edema region, and whether a site is other than the site referred to as the eloquent area in cerebral arteriovenous malformation (AVM); and displaying of these results can help those skilled in the art to make optimal decisions about the administration position to be adopted by themselves.

Example 23: Example of Predicting the Probability of Occurrence of Adverse Effects of Cell Therapy Based on Cell Administration Route (1) Target Patients Patients with cerebral infarction are targeted.

(2) MRI Image Capturing

For each patient, MRI images of the brain are captured at the time corresponding to the subacute phase and the chronic phase. The image capturing is performed using an MRI apparatus (3T Achieva TX(Philips Medical Systems)) with default settings (b=0, 1000 s mm-2, TR/TE=5032/85 msec, NEX=1, voxel size=3×3×3 mm3, no. of slices=43, 32 diffusion gradient directions).

(3) MRI Image Analysis

Based on the MRI images captured, evaluation is made on: the distance between the cranial bone and the brain surface directly below the skin through which an administration needle passes; whether the eloquent area is directly below an insertion point of an administration needle; whether there is a thick vein directly below an insertion point of an administration needle; whether the administration needle passes through an artificial object, such as an artificial bone, an artificial dura mater or a titanium plate; the distance between the sulcus and the administration needle; and the distance between an administration needle and a thick blood vessel in the brain, to determine a cell administration route.

(4) Preparation and Administration of Bone Marrow Stem Cells

After registering the case, the patient's bone marrow is collected immediately, and cell culture and preparation of bone marrow stem cells are performed at the Cell Processing Center in the Clinical Research and Medical Innovation Center, Hokkaido University Hospital. The prepared bone marrow stem cells (20 million or 50 million/patient) are administered directly into the patient's brain three to five weeks after the bone marrow collection.

(5) Adverse Effect Evaluation

The patients after administration are evaluated for adverse effects due to cell therapy (adverse effects on motor function, sensory function, language function or vision, blood loss, etc.).

(6) Results

Correlation is found between the probability of occurrence of adverse effects of cell therapy and points such as the distance between the cranial bone and the brain surface directly below the skin through which an administration needle passes, whether the eloquent area is directly below an insertion point of an administration needle, whether there is a thick vein directly below an insertion point of an administration needle, whether the administration needle passes through an artificial object, such as an artificial bone, an artificial dura mater or a titanium plate, the distance between the sulcus and the administration needle, and the distance between an administration needle and a thick blood vessel in the brain; and displaying of these results can help those skilled in the art to make optimal decisions about the administration position to be adopted by themselves.

Example 24: Example of Predicting the Probability of Occurrence of Adverse Effects of Cell Therapy Based on Cell Administration Position and Cell Administration Route for Administration at the Cell Administration Position (1) Target Patients Patients with cerebral infarction are targeted.

(2) MRI Image Capturing

For each patient, MRI images of the brain are captured at the time corresponding to the subacute phase and the chronic phase. The image capturing is performed using an MRI apparatus (3T Achieva TX(Philips Medical Systems)) with default settings(b=0, 1000 s mm-2, TR/TE=5032/85 msec, NEX=1, voxel size=3×3×3 mm3, no. of slices=43, 32 diffusion gradient directions).

(3) MRI Image Analysis

Based on the MRI images captured, evaluation is made on points such as the distance to the brain surface, the distance to the damage position in the brain, the distance to the edema region, and whether a site is other than the site referred to as the eloquent area in cerebral arteriovenous malformation (AVM), to determine a cell administration position; and evaluation is made on: the distance between the cranial bone and the brain surface directly below the skin through which an administration needle passes; whether the eloquent area is directly below an insertion point of an administration needle; whether there is a thick vein directly below an insertion point of an administration needle; whether the administration needle passes through an artificial object, such as an artificial bone, an artificial dura mater or a titanium plate; the distance between the sulcus and the administration needle; and the distance between an administration needle and a thick blood vessel in the brain, to determine a cell administration route.

(4) Preparation and Administration of Bone Marrow Stem Cells

After registering the case, the patient's bone marrow is collected immediately, and cell culture and preparation of bone marrow stem cells are performed at the Cell Processing Center in the Clinical Research and Medical Innovation Center, Hokkaido University Hospital. The prepared bone marrow stem cells (20 million or 50 million/patient) are administered directly into the patient's brain three to five weeks after the bone marrow collection.

(5) Adverse Effect Evaluation

The patients after administration are evaluated for adverse effects due to cell therapy (adverse effects on motor function, sensory function, language function or vision, blood loss, etc.).

(6) Results

Correlation is found between the probability of occurrence of adverse effects of cell therapy and the points such as the distance to the brain surface, the distance to the damage position in the brain, the distance to the edema region, and whether a site is other than the site referred to as the eloquent area in cerebral arteriovenous malformation (AVM), as well as the points such as the distance between the cranial bone and the brain surface directly below the skin through which an administration needle passes, whether the eloquent area is directly below an insertion point of an administration needle, whether there is a thick vein directly below an insertion point of an administration needle, whether the administration needle passes through an artificial object, such as an artificial bone, an artificial dura mater or a titanium plate, the distance between the sulcus and the administration needle, and the distance between an administration needle and a thick blood vessel in the brain; and displaying of these results can help those skilled in the art to make optimal decisions about the administration position to be adopted by themselves.

(Note)

As described above, the present disclosure is exemplified by the use of its preferred embodiments. However, the scope of the present disclosure should be interpreted solely based on the Claims. It is also understood that any patent, any patent application, and any references cited herein should be incorporated herein by reference in the same manner as the contents are specifically described herein. The present application claims priority to Japanese Patent Application No. 2019-239560 filed on Dec. 27, 2019 with the Japan Patent Office. It is understood that the entire content thereof is incorporated herein by reference.

INDUSTRIAL APPLICABILITY

The present disclosure provides various approaches for successfully guiding cell therapy in the brain, and the present disclosure is applicable in the medical technology and medical device industries.

The invention claimed is:

1. A method for identifying a site of administration of cells in cell therapy for a central nervous system disorder in a subject, the method comprising:
  A) acquiring, by an imaging device, image data on at least part of the brain of the subject;
  B) obtaining information on the brain of the subject by a computer device in communication with the imaging device;
  C) depicting motor fibers by the computer device using the acquired image data and data on the brain of the subject;
  D) identifying, by the computer device, a damage position in which the motor fibers are damaged, which identifies a part where running data on the motor fibers is lower than other sites to identify the lower part as damaged motor fibers;
  E) selecting, by the computer device, a safe region near the damage position as an administration site; and
  F) outputting the selected administration site as a graphic display, wherein:
    (a) the imaging device comprises an MRI, a CT, an ultrasound examination device or an angiography examination device,
    (b) the running data on the motor fibers is represented in a DTI image, and optionally by an FA value (fractional anisotropy value) in the DTI image,
    (c) a decrease in the running data at a site where the running data on the motor fibers is lower than other parts is a decrease of at least 50% or more,
    (d) the safe region includes a position present within a radius of about 1.5 cm from the damage position,
    (e) the safe region is a position present within a radius of about 1.5 cm from the damage position and is selected from a site considered to have no important function on nerve function,
    (f) the administration site is positioned caudally to the brain relative to the damage position,
    (g) the administration site is determined for each damage position,
    (h) one or more of the administration sites exist with respect to the damage position,
    (i) when the running data on the motor fibers is not acquired, a damaged part is determined with reference to healthy motor fibers on a contralateral side, or
    (j) as for the selecting, a DWI image is compared with a T2 image to determine a region damaged by current cerebral infarction, and the region is excluded from the selection, a site that is DWI-negative but has strong edema in the T2 image and a FLAIR image is also excluded from the selection, and motor fibers are visualized in a DTI region, and the region of the visualized motor fibers is excluded from the selection, and wherein optionally in the T2-weighted image and the FLAIR image in the MRI, a site that meets both of:
      i) a high signal intensity area in the FLAIR image plotting signal intensity; and
      ii) a high signal intensity area in the T2-weighted image plotting signal intensity, is identified as edema.

2. The method according to claim 1, wherein:
[1] when tractography is visualized in the DTI image, a site that meets conditions of:
  (a) normal brain tissue that is as close as possible to an area where the tractography is raptured or weakened in the DTI image (usually a white area with DWI in the acute phase of cerebral infarction; high signal intensity in T2/FLAIR in the chronic phase of cerebral infarction; high signal intensity in CT in the acute phase of trauma/cerebral hemorrhage; high signal intensity in T2/FLAIR in the chronic phase of trauma/cerebral hemorrhage); and
  (b) a highly safe region (an area where there is little damage even if bleeding or allergic reaction occurs: a site other than the site generally referred to as an eloquent area* in AVM), and
  (c) optionally, a part that avoids, but is as close as possible to, the high signal intensity area in the T2/FLAIR image, is selected as an administration site, or
[2] when tractography is not visualized in the DTI image,
  (aa) the setting for ROI for visualizing tractography is set solely for each of the precentral gyrus, the crus posterius capsulae internae, and the bridge (usually, nerve fibers that pass through the following three: the precentral gyrus, the crus posterius capsulae internae, and the bridge are often selected), and with the visualized tractography used as a reference, from among them, normally expected motor fibers in humans are selected, or
  (bb) when tractography is not visualized even in the (aa), running of motor fibers is estimated with reference to tractography on the contralateral side, and a site where an injured site indicated as high signal intensity in a DWI image in the acute phase, or an injured site indicated as low signal intensity in a T2/FLAIR image in the chronic phase, overlaps with an estimated passing point of tractography is estimated to be the site where motor fibers are ruptured, to perform [1].

3. A non-transitory recording medium having a program stored thereon that causes a computer to execute a method for identifying a cell administration site in cell therapy for a central nervous system disorder in a subject, the method comprising:
A) acquiring, by an imaging device, image data on at least part of the brain of the subject;
B) obtaining information on the brain of the subject by a computer device in communication with the imaging device;
C) depicting motor fibers by the computer device using the acquired image data and data on the brain of the subject;
D) identifying, by the computer device, a damage position in which the motor fibers are damaged, which identifies a part where running data on the motor fibers is lower than other sites to identify the lower part as damaged motor fibers;
E) selecting, by the computer device, a safe region near the damage position as an administration site; and
F) outputting the selected administration site as a graphic display, wherein:
  (a) the imaging device comprises an MRI, a CT, an ultrasound examination device or an angiography examination device,
  (b) the running data on the motor fibers is represented in a DTI image, and optionally by an FA value (fractional anisotropy value) in the DTI image,
  (c) a decrease in the running data at a site where the running data on the motor fibers is lower than other parts is a decrease of at least 50% or more,
  (d) the safe region includes a position present within a radius of about 1.5 cm from the damage position,
  (e) the safe region is a position present within a radius of about 1.5 cm from the damage position and is selected from a site considered to have no important function on nerve function,
  (f) the administration site is positioned caudally to the brain relative to the damage position,
  (g) the administration site is determined for each damage position,
  (h) one or more of the administration sites exist with respect to the damage position,
  (i) when the running data on the motor fibers is not acquired, a damaged part is determined with reference to healthy motor fibers on a contralateral side, or
  (j) as for the selecting, a DWI image is compared with a T2 image to determine a region damaged by current cerebral infarction, and the region is excluded from the selection, a site that is DWI-negative but has strong edema in the T2 image and a FLAIR image is also excluded from the selection, and motor fibers are visualized in a DTI region, and the region of the visualized motor fibers is excluded from the selection, and wherein optionally in the T2-weighted image and the FLAIR image in the MRI, a site that meets both of:
    i) a high signal intensity area in the FLAIR image plotting signal intensity, and
    ii) a high signal intensity area in the T2-weighted image plotting signal intensity, is identified as edema.

4. The recording medium according to claim 3, wherein:
[1] when tractography is visualized in the DTI image, a site that meets conditions of:
  (a) normal brain tissue that is as close as possible to an area where the tractography is raptured or weakened in the DTI image (usually a white area with DWI in the acute phase of cerebral infarction; high signal intensity in T2/FLAIR in the chronic phase of cerebral infarction; high signal intensity in CT in the acute phase of trauma/cerebral hemorrhage; high signal intensity in T2/FLAIR in the chronic phase of trauma/cerebral hemorrhage); and
  (b) a highly safe region (an area where there is little damage even if bleeding or allergic reaction occurs: a site other than the site generally referred to as an eloquent area* in AVM), and
  (c) optionally, a part that avoids, but is as close as possible to, the high signal intensity area in the T2/FLAIR image, is selected as an administration site, or
[2] when tractography is not visualized in the DTI image,
  (aa) the setting for ROI for visualizing tractography is set solely for each of the precentral gyrus, the crus posterius capsulae internae, and the bridge (usually, nerve fibers that pass through the following three: the precentral gyrus, the crus posterius capsulae internae, and the bridge are often selected), and with the visualized tractography used as a reference, from among them, normally expected motor fibers in humans are selected, or
  (bb) when tractography is not visualized even in the (aa), running of motor fibers is estimated with reference to tractography on the contralateral side, and a site where an injured site indicated as high signal intensity in a DWI image in the acute phase, or an injured site indicated as low signal intensity in a T2/FLAIR image in the chronic phase, overlaps with an estimated passing point of tractography is estimated to be the site where motor fibers are ruptured, to perform [1].

5. A system for identifying a cell administration site in cell therapy for a central nervous system disorder in a subject, the system comprising:
A) an acquiring section for acquiring, by an imaging device, image data on at least part of the brain of the subject;
B) an information obtaining section for obtaining information on the brain of the subject by a computer device in communication with the imaging device;
C) a depicting section for depicting motor fibers by the computer device using the acquired image data and data on the brain of the subject;
D) an identifying section for identifying, by the computer device, a damage position in which the motor fibers are damaged, which identifies a part where running data on the motor fibers is lower than other sites to identify the lower part as damaged motor fibers;
E) a selecting section for selecting, by the computer device, a safe region near the damage position as an administration site; and F) an outputting section for outputting the selected administration site as a graphic display, wherein:
 (a) the imaging device comprises an MRI, a CT, an ultrasound examination device or an angiography examination device,
 (b) the running data on the motor fibers is represented in a DTI image, and optionally by an FA value (fractional anisotropy value) in the DTI image,
 (c) a decrease in the running data at a site where the running data on the motor fibers is lower than other parts is a decrease of at least 50% or more,
 (d) the safe region includes a position present within a radius of about 1.5 cm from the damage position,
 (e) the safe region is a position present within a radius of about 1.5 cm from the damage position and is selected from a site considered to have no important function on nerve function,
 (f) the administration site is positioned caudally to the brain relative to the damage position,
 (g) the administration site is determined for each damage position,
 (h) one or more of the administration sites exist with respect to the damage position,
 (i) when the running data on the motor fibers is not acquired, a damaged part is determined with reference to healthy motor fibers on a contralateral side, or
 (j) as for the selecting, a DWI image is compared with a T2 image to determine a region damaged by current cerebral infarction, and the region is excluded from the selection, a site that is DWI-negative but has strong edema in the T2 image and a FLAIR image is also excluded from the selection, and motor fibers are visualized in a DTI region, and the region of the visualized motor fibers is excluded from the selection, and wherein optionally in the T2-weighted image and the FLAIR image in the MRI, a site that meets both of:
  i) a high signal intensity area in the FLAIR image plotting signal intensity; and
  ii) a high signal intensity area in the T2-weighted image plotting signal intensity, is identified as edema.

6. The system according to claim 5, wherein:
[1] when tractography is visualized in the DTI image, a site that meets conditions of:
 (a) normal brain tissue that is as close as possible to an area where the tractography is raptured or weakened in the DTI image (usually a white area with DWI in the acute phase of cerebral infarction; high signal intensity in T2/FLAIR in the chronic phase of cerebral infarction; high signal intensity in CT in the acute phase of trauma/cerebral hemorrhage; high signal intensity in T2/FLAIR in the chronic phase of trauma/cerebral hemorrhage); and
 (b) a highly safe region (an area where there is little damage even if bleeding or allergic reaction occurs: a site other than the site generally referred to as an eloquent area* in AVM), and
 (c) optionally, a part that avoids, but is as close as possible to, the high signal intensity area in the T2/FLAIR image, is selected as an administration site, or
[2] when tractography is not visualized in the DTI image,
 (aa) the setting for ROI for visualizing tractography is set solely for each of the precentral gyrus, the crus posterius capsulae internae, and the bridge (usually, nerve fibers that pass through the following three: the precentral gyrus, the crus posterius capsulae internae, and the bridge are often selected), and with the visualized tractography used as a reference, from among them, normally expected motor fibers in humans are selected, or
 (bb) when tractography is not visualized even in the (aa), running of motor fibers is estimated with reference to tractography on the contralateral side, and a site where an injured site indicated as high signal intensity in a DWI image in the acute phase, or an injured site indicated as low signal intensity in a T2/FLAIR image in the chronic phase, overlaps with an estimated passing point of tractography is estimated to be the site where motor fibers are ruptured, to perform [1].

* * * * *